United States Patent
Li et al.

(10) Patent No.: US 6,977,256 B2
(45) Date of Patent: Dec. 20, 2005

(54) COMPOUNDS AND COMPOSITIONS AS CATHEPSIN S INHIBITORS

(75) Inventors: Jiayo Li, San Bruno, CA (US); David J. Aldous, Gillette, NJ (US); Sukanthini Thurairatnam, Bedminster, NJ (US)

(73) Assignees: Aventis Pharmaceuticals Inc., Bridgewater, NJ (US); Axys Pharmaceuticals, Inc., South San Francisco, CA (US)

( * ) Notice: Subject to any disclaimer, the term of this patent is extended or adjusted under 35 U.S.C. 154(b) by 7 days.

(21) Appl. No.: 10/294,526

(22) Filed: Nov. 14, 2002

(65) Prior Publication Data

US 2003/0199506 A1 Oct. 23, 2003

Related U.S. Application Data

(60) Provisional application No. 60/332,605, filed on Nov. 14, 2001.

(51) Int. Cl.$^7$ .................. A61K 31/5375; C07D 413/12
(52) U.S. Cl. ................ 514/237.8; 514/231.2; 514/236.2; 514/237.5; 544/106; 544/124; 544/138
(58) Field of Search ................ 544/124, 138, 544/106; 514/236.2, 237.5, 237.8, 231.2

(56) References Cited

U.S. PATENT DOCUMENTS

| | | | |
|---|---|---|---|
| 4,927,809 A | 5/1990 | Stuber et al. | |
| 5,424,325 A | 6/1995 | Ando et al. | |
| 5,486,623 A | 1/1996 | Zimmerman et al. | |
| 5,498,616 A | 3/1996 | Mallano et al. | |
| 5,847,135 A | 12/1998 | Bemis et al. | |
| 5,852,007 A | 12/1998 | Chatterjee et al. | |
| 5,874,424 A | 2/1999 | Batchelor et al. | |
| 5,998,390 A | 12/1999 | Ramamurthy et al. | |
| 6,004,933 A | 12/1999 | Spruce et al. | |
| 6,015,791 A | 1/2000 | Gyorkos et al. | |
| 6,022,861 A | 2/2000 | Scarborough et al. | |
| 6,114,310 A | 9/2000 | Chamberland et al. | |
| 6,124,333 A | 9/2000 | Miller et al. | |
| 6,255,453 B1 | 7/2001 | Gyorkos et al. | |
| 6,353,017 B1 | 3/2002 | Altmann et al. | |
| 6,455,502 B1 | 9/2002 | Bryant et al. | |
| 6,476,026 B1 | 11/2002 | Bryant et al. | |
| 6,492,362 B1 | 12/2002 | Graupe et al. | |
| 6,506,733 B1 | 1/2003 | Buysse | |
| 6,576,630 B1 | 6/2003 | Link et al. | |
| 6,608,057 B2 | 8/2003 | Cywin et al. | |

FOREIGN PATENT DOCUMENTS

| | | |
|---|---|---|
| EP | 0272671 | 6/1988 |
| EP | 0355572 | 2/1990 |
| EP | 0376012 | 7/1990 |
| EP | 0419683 | 4/1991 |
| EP | 0536399 | 4/1993 |
| EP | 0652009 | 10/1995 |
| EP | 0754454 | 1/1997 |
| EP | 0291234 | 11/1998 |
| JP | 42009133 | 5/1967 |
| JP | 63303868 | 12/1988 |
| JP | 06192199 | 7/1994 |
| JP | 2001-011037 | 1/2001 |
| JP | 2001-055366 | 2/2001 |
| WO | WO 98/21188 | 5/1988 |
| WO | WO 95/13069 | 5/1995 |
| WO | WO 95/15309 | 6/1995 |
| WO | WO 95/24382 | 9/1995 |
| WO | WO 96/21655 | 7/1996 |
| WO | WO 96/30353 | 10/1996 |
| WO | WO 96/40647 | 12/1996 |
| WO | WO 96/40744 | 12/1996 |
| WO | WO 96/41638 | 12/1996 |
| WO | WO 97/03679 | 2/1997 |
| WO | WO 98/01133 | 1/1998 |
| WO | WO 98/01428 | 1/1998 |
| WO | WO 98/05336 | 2/1998 |
| WO | WO 98/08802 | 3/1998 |
| WO | WO 98/08867 | 3/1998 |
| WO | WO 98/23588 | 6/1998 |
| WO | WO 98/49190 | 11/1998 |
| WO | WO 99/24460 | 5/1999 |
| WO | WO 00/48992 | 8/2000 |
| WO | WO 00/49007 | 8/2000 |
| WO | WO 00/49008 | 8/2000 |
| WO | WO 00/51998 | 9/2000 |
| WO | WO 00/59881 | 10/2000 |
| WO | WO 00/69855 | 11/2000 |
| WO | WO 01/09110 | 2/2001 |
| WO | WO01/09169 | 2/2001 |
| WO | WO 01/19796 | 3/2001 |

(Continued)

OTHER PUBLICATIONS

U.S. Appl. No. 10/035,783, filed Dec. 24, 2001, Graupe et al.

(Continued)

*Primary Examiner*—Golam M M Shameem
(74) *Attorney, Agent, or Firm*—Synnestvedt & Lechner LLP

(57) ABSTRACT

The present invention relates to novel selective cathepsin S inhibitors, the pharmaceutically acceptable salts and N-oxides thereof, their uses as therapeutic agents and the methods of their making.

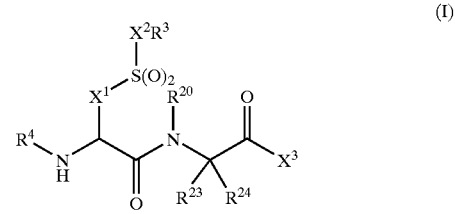

21 Claims, No Drawings

FOREIGN PATENT DOCUMENTS

| WO | WO 01/19808 | 3/2001 |
|----|-------------|--------|
| WO | WO 01/19816 | 3/2001 |
| WO | WO 01/30772 | 5/2001 |
| WO | WO 01/55125 | 8/2001 |
| WO | WO 01/58886 | 8/2001 |
| WO | WO02/20485 | 3/2002 |
| WO | WO02/096892 | 5/2002 |
| WO | WO02/057248 | 7/2002 |
| WO | WO02/057249 | 7/2002 |
| WO | WO02/057270 | 7/2002 |
| WO | WO02/100849 | 12/2002 |

OTHER PUBLICATIONS

U.S. Appl. No. 10/719,080, filed Nov. 21, 2003, Graupe et al.

U.S. Appl. No. 10/787,367, filed Sep. 16, 2002, Graupe et al.

U.S. Appl. No. 10/418,183, filed Oct. 23, 2003, Li et al.

Adams, et al., Potent and Selective Inhibitors of the Proteasom: Dipeptidyl Boronic Acids, Bioorganic & Medicinal Chemistry Letters, 8: 333–338 (1998).

Ashworth, et al., 4–Cyanothiazolidides as very potent, stable inhibitors of dipeptidyl peptidases IV, Bioorganic & Med. Chem. Letters, B, Oxford, 6(22):2745–2748 (1996).

Bergeman, et al., Studies on the reactivity of .alpha.–cyano.alpha–isocyano alkanoates. Versitile synthons for the assembly of imidazoles, Helv.Chim. ACTA, 82(6):909–918 (1999).

Billson, et al., The Design and Synthesis of Inhibitors of the Cysteinyl, Bioorg. Med. Chem. Lett. vol. 8, pp. 993–998, 1998.

Bromme, et al., Potent Inactivation of Cathepsins S and L , Biol. Chem. Hoppe—Seyler. vol. 375, No. 5, pp. 343–347, 1994.

Chatterjee, et al., D–Amino Acid Containing, High–Affinity Inhibitors of Recombinant Human Calpain I, Journal of Medicinal Chemistry, vol. 41, No. 15, p: 2663–2666 (1998).

Cohen, et al., Therapy of relapsing multiple sclerosis. Treatment approaches for nonresponders, Journal of Neuroimmunology, 98: 29–36 (1999).

Dufour, et al., Engineering nitrile hydratase activity into a cysteine protease by a single mutation, Bio.chemistry, US, Am. Chem. Soc., Easton, PA, 34(50):16382–16388 (1995).

Edwards, et al., Design, Synthesis, and Kinetic Evaluation of a Unique Class of Elastase Inhibitors, the Peptidyl a–Ketobenzoxazoles, and the X–ray Crystal Structure of Covalent Complex between Porcine Pancreatic Elastase and Ac–Ala–Pro–Val–2–Benzoxazole, Journal of American Chemical Society, vol. 114, No. 5, p 1854–1863 (1992).

Evoli, et al., abstract only, Drugs, 1996, 52(5), 662–70.

Gour–Salin, et al., Inhibition of papain by peptide nitriles: conversion of the nitrile group into other functionalities via the papain:nitrile thiomidate ester adduct, Can. J. of Chem, CA, National Research Council. Ottawa, 69(8):1288–1297 (1991).

Hallegua, et al., Cyclosporine for lupus membranous nephritis: experience with ten patients and review of the literature, Lupus, 9: 241–251 (2000).

Hanzlik, et al., Reversible covalent binding of peptide nitriles to papain, Biochim. Biophys, Acta, vol. 1035, No. 1, 1990, pp. 62–70.

Harris, et al., Characteristics of a continuous fluorogenic assay for calpain I. Kinetic evaluation of peptide aldehydes, halomethyl ketones and )achalasia) methyl ketones as inhibitors of the enzyme, Chemical Abstracts, 110:7, Bioorg. Med. Chem. Lett, 5(4) 393–398 (1995).

Heitmiller, R.F., abstract only., Semin, Thorac. Cardiovasc. Surg., 1999, 11(1), 41–6.

Katritzky, et al., Benzotriazole–assisted synthesis of alpha.–(acylamino) nitrites and a conceptually novel method for peptide elongation, Chem. Soc., Perkin Trans. 1(7):1853–1857 (1990).

Khamashta, et al., Expert. Opin. Investig. Drugs, 2000, 9(7), 1581–93.

Krantz, et al., Peptidyl (Acyloxy)methyl Ketones and the Quiescent, Biochemistry. vol. 30, pp. 4678–4687 1991.

Levy, E.G., Baillieres Clin. Endocrinol. Metab., 1997, 11(3) 585–595.

Li, et al., Aminoacylpyrrolidine–2–nitriles: Potent and stable inhibitors of dipeptidyl–peptidase IV (CD 26), Archives of Biochem. and Bioph., 323(1)148–154 (1995).

Lipshutz, et al., Chiral induction in originally racemic amino acids via 5–acyl and 5–acyloxyaminooxazoles, Isr, J. Chem. 27(1):49–55 (1986), abstract.

Lipshutz, et al., Heterocycles as masked diamide/dipeptide equivalents. Formation and reactions of substituted 5–(acylamino)oxazoles as intermediates en route to the cyclopeptide alkaloids, . Am. Chem. Soc., 105(26):7703–7713 (1983).

Lipshutz, et al., Oxazolophanes as masked cyclopeptide alkaloid equivalents: cyclic peptide chemistry without peptide couplings, J. Am. Chem. Soc., 112(19):7032–7041 (1990).

Marquis, et al., Potent dipeptidylketone inhibitors of the cysteine protease cathespin, Chemical Abstracts, 7:4 581–588 (1999).

McMath, et al., Direct dialkylation of peptide nitriles: Application of the synthesis of 1–aminocyclopropane–1 carboxylic acid (Acc)–containing dipeptides, Bull. Soc. Chim. Fr. 134(1):105–110 (1997).

Moriya, et al., Synthesis and Hypolipidemic Activities of 5–Thienyl–4–oxazoleacetic Acid Derivatives.sup.1, J. Med. Chem., 29: 333–341 (1986).

Moser, et al., 130 Poly (dipeptamidinium)–Salze: definition und metoden zur praparativen herstellung. poly (dipeptamidinium) salts: definition and methods of preparation, Helvitica Chimica ACTA, CH, Verlag, Basel 69:1224–1262 (1986).

Nippon, K., Patent Abstracts of Japan, Publication No. 63301868, 013(137)(1988), abstract.

North, et al., Synthetic studies towards cyclic peptides. Concise synthesis of thiazoline and thiazole containing amino acids, Tetrahedron, 46(24):8627–8290 (1990).

Ogilvie, et al., Peptidomimetic inhibitors of the human cytomegalovirus protease, Journal of Medicinal Chemistry vol. 40 No. 25 (1997).

Picken, et al., Inhibition of bovine cathespin B by amino acid–derived nitriles, Biochemical Society Transactions, vol. 18, No. 2, p:316 (1990).

Pliura, et al., Comparative behavior of colpain and cathespin B , Biochem. J. vol. 288, pp. 759–762, 1992.

Polman, et al., Drug treatment of multiple sclerosis, BMJ, 321: 19–26 (2000).

Riese, et al., Essential Role for Cathesin S in MHC Class II–Associated Invariant Chain Processing and Peptide Loading, Immunity, 4: 357–366 (Apr. 1996).

Smith, et al., New Inhibitors of Cysteine Proteinase, J. Am. Chem. Soc. vol. 110, No. 13, pp. 4429–4431, 1988.

Suave, et al., Carboxylmodified amino acids and peptides, I An efficient method for the synthesis of monofuctionalized enamines and monofuntionalized methyl ketone derivatives fom thioamides via episulfides and thioiminium salts, Tetrahedron Lett, 29:19 2295–2298 (1988).

Suzue, S., Hepatic agents. I. Synthesis of aminocyl (and hydroxyacyl) aminoacetonitriles, Chem. and Pharm. Bull. (Tokyo) (1968), 16(8), 1417–32.

Suzue, et al., Studies on Heptic Agents , Chem. Pharm. Bull. vol. 16, No. 8, pp. 1417–1432, Aug. 1968.

Suzuki, et al., Synthesis of 2–Aryl–4(3–thienyl)imidazole Derivatives with Antinflammatory Properties .sup.1), Chem. Pharm. Bull, 34(8):3111–3120 (1996).

Tao, et al., Inhibition of Calpain By Peptidyl Heterocycles, Bioorganic & Medicinal Chemnistry Letters, 6:24 3009–3112 (1996).

Thompson, et al., Carboxyl–modified amino acids and peptides as protease inhibitors, J. Med. Chem., 29(1):104–111 (1986).

Tsutsumi, et al., Synthesis and Structure–Activity Relationships of Peptidyl a–Keto Heterocycles as Novel Inhibitors of Prolyl Endopeptidase, Journal of Medicinal Chemistry, vol. 37, No. 21, pp. 3492–3502 (1994).

Vargha, E., Peptide derivatives. VI. N–protected di– and tripeptide nitriles, Stud. Univ. Babes–Bolyai, Ser. Chem., 13(2):31–5 (English abstract of article in Romanian) (1968).

Varghese, The structure and resonance Raman spectra—structure correlations for methyloxycarbonyl–L–phenylalanyl–L–alanine ethyl dithioester, Can. J. Chem., 64(8):1668–1673 (1996).

Yamada, et al., Studies of unusual amino acids and their peptides.IX. The synthetic study of bottomycins B1 and B2, Bul. Chem. Soc., Jpn. 51(3):878–83 (1978), abstract.

, Derwent Abstract of Japanese Patent Application 06–192199, (Jul. 12, 1994).

U.S. Appl. No. 09/927,188, filed Aug. 10, 2001, Cai et al.
U.S. Appl. No. 09/927,324, filed Aug. 10, 2001, Butler et al.
U.S. Appl. No. 09/928,122, filed Aug. 10, 2001,Breitenbucher et al.
U.S. Appl. No. 09/946,214, filed Sep. 5, 2001, Gu et al.
U.S. Appl. No. 10/042,565, filed Nov. 16, 2001, Quibell et al.
U.S. Appl. No. 10/148,612, filed Aug. 21, 2002, Ohmoto et al.
U.S. Appl. No. 10/148,613, filed Aug. 28, 2002, Ohmoto et al.
U.S. Appl. No. 10/181,713, filed Jul. 22, 2002, Ohmoto et al.
U.S. Appl. No. 10/181,799, filed Jul. 23, 2002, Ohmoto et al.
U.S. Appl. No. 10/231,425, filed Aug. 28, 2002, Buxton et al.
U.S. Appl. No. 10/275,583, filed Nov. 7, 2002, Cowen et al.
U.S. Appl. No. 10/256,512, filed Sep. 27, 2002, Bekkali et al.
U.S. Appl. No. 10/258,053, filed Oct. 17, 2002, Cummings et al.
U.S. Appl. No. 10/279,424, filed Oct. 24, 2002, Bekkali et al.
U.S. Appl. No. 10/466,385 filed Jan. 8, 2004, Quibell et al.

Chapman, et al., Emerging Roles for Cysteine Proteases in Human Biology, Ann. Rev. Physiol.; 1997; 59; pp. 63–88.

Dranoff, et al., Cathespin S Required for Normal MHC Class II Peptide Loading and Germinal Center Development, Immunity; 1999; 10; pp. 197–206.

Fenwick, et al., Diastereoselective Synthesis, Activity and Chiral Stability of Cyclic Alkoxyketone Inhibitors Cathespin K., Bioorg. Med. Chemm. Lett.; 2001; 11(2); pp. 199–202.

Fenwick, et al., Solid–phase Synthesis of Cyclic Alkoxyketones, Inhibitors of the Cysteine Protease Cathespin K., Bioorg. Med. Chem. Lett.; 2001; 11(2); pp. 195–198.

Greenspan, et al., Identification of Dipeptidyl Nitriles as Potent and Selective Inhibitors of cathespin B Through Structure–based Drug Design, J. Med. Chem.; 2001; 44; pp. 4524–4534.

Lowe, et al., Kinetic Specificity in Papain–catalyzed Hydrolyses, Biochem. J.; 1971; 124(1); pp. 107–115.

Maciewicz, et al., A comparison of Four Cathespins (B,L,N and S) with Collagenolytic Activity From Rabbit Spieen, Biochem J.; 1998; 256; pp. 433–440.

Marquis, et al., Azeanone–based Inhibitors of Human and Rat Cathespin K., J. Med. Chem.; 2000; 44(9); pp. 1380–1395.

Nakagawa, et al., Imparied Invariant Chain Degradation and Antigen Presentation and.Diminished Collagen–induced Arthritis in Cathespin S–null Mice, Immunity; 1999; 10; pp. 207–217.

Otto, et al., Cysteine Protease and their Inhibitors, Chem. Rev.; 1997; 97; pp. 133–171.

Shi, et al., Molecular Cloning and Expression of Human Alveolar Macrophage Cathespin S, an Elastinolytic Cysteine Protease, J. Biol. Chem.; 1992; 267; pp. 7258–7262.

Singh, et al., beta–lactams as Enzyme Inhibitors., IDrugs; 2000; 3(5); pp. 512–517.

Villadangos, et al., Cathespin S Activity Regulates Antigen Presentation and Immunity, J. Clin. Invest; 1998; 101(10); pp. 2351–2363.

COMPOUNDS AND COMPOSITIONS AS CATHEPSIN S INHIBITORS

This Application is based on and claims priority from U.S. Provisional Application No. 60/332,605 filed on Nov. 14, 2001, which is incorporated herein by reference.

THE INVENTION

This application relates to compounds and compositions for treating diseases associated with cysteine protease activity, particularly diseases associated with activity of cathepsin S.

DESCRIPTION OF THE FIELD

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increase expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. An increase in cathepsin S activity contributes to the pathology and/or symptomatology of a number of diseases. Accordingly, molecules that inhibit the activity of cathepsin S protease are useful as therapeutic agents in the treatment of such diseases.

SUMMARY OF THE INVENTION

This Application relates to compounds of Formula (I):

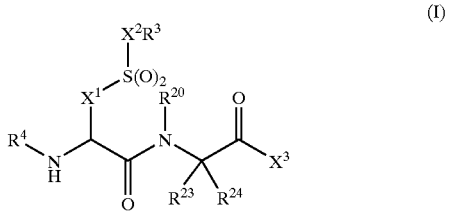

(I)

wherein:

$X^1$ and $X^2$ are both methylene or $X^1$ is ethylene and $X^2$ is methylene or a bond;

$R^3$ is —$CR^5$=$CHR^6$, —$CR^5(CR^6{}_3)_2$, —$CR^7$=$NR^8$, or ($C_{3-12}$)cycloalkyl, wherein $R^5$ and $R^6$ are independently hydrogen or ($C_{1-4}$)alkyl or $R^5$ and $R^6$ together with the atoms to which $R^5$ and $R^6$ are attached form ($C_{3-12}$)cycloalkyl, hetero($C_{3-12}$)cycloalkyl, ($C_{6-12}$)aryl, hetero($C_{5-12}$)aryl, ($C_{9-12}$)bicycloaryl or hetero($C_{8-12}$)bicycloaryl and $R^7$ and $R^8$ together with the atoms to which $R^7$ and $R^8$ are attached form hetero($C_{3-12}$)cycloalkyl, hetero($C_{5-12}$)aryl or hetero($C_{8-12}$)bicycloaryl, wherein $R^3$ optionally is substituted by 1 to 5 radicals independently selected from a group consisting of ($C_{1-4}$)alkyl, cyano, halo, halo-substituted $C_{1-4}$)alkyl, nitro, —$X^4NR^9R^9$, —$X^4OR^9$, —$X^4SR^9$, —$X^4C(O)NR^9R^9$, —$X^4C(O)OR^9$, —$X^4S(O)R^{10}$, —$X^4S(O)_2R^{10}$ and —$X^4C(O)R^{10}$, wherein $X^4$ is a bond or ($C_{1-2}$)alkylene, $R^9$ at each occurrence independently is hydrogen, ($C_{1-3}$)alkyl or halo-substituted ($C_{1-3}$)alkyl and $R^{10}$ is ($C_{1-3}$)alkyl or halo-substituted ($C_{1-3}$)alkyl; and $R^4$ is —$C(O)X^5R^{11}$ or —$S(O)_2X^5R^{11}$, wherein $X^5$ is a bond, —O— or —$NR^{12}$—, wherein $R^{12}$ is hydrogen or ($C_{1-6}$)alkyl, and $R^{11}$ is (i) ($C_{1-6}$)alkyl optionally substituted by —$OR^{13}$, —$SR^{13}$, —$S(O)R^{13}$, —$S(O)_2R^{13}$, —$C(O)R^{13}$, —$C(O)OR^{13}$, —$C(O)NR^{13}R^{14}$, —$NR^{13}R^4$, —$NR^{14}C(O)R^{13}$, —$NR^{14}C(O)OR^{13}$, —$NR^{14}C(O)NR^{13}R^{14}$ or —$NR^{14}C(NR^{14})NR^{13}R^{14}$, wherein $R^{13}$ is ($C_{3-12}$)cycloalkyl($C_{0-3}$)alkyl, hetero($C_{5-12}$)cycloalkyl($C_{0-3}$)alkyl, ($C_{6-12}$)aryl($C_{0-3}$)alkyl, hetero($C_{5-12}$)aryl($C_{0-3}$)alkyl, ($C_{9-12}$)bicycloaryl($C_{0-3}$)alkyl or hetero($C_{8-12}$)bicycloaryl($C_{0-3}$)alkyl and $R^{14}$ at each occurrence independently is hydrogen or ($C_{1-6}$)alkyl, or (ii) ($C_{3-12}$)cycloalkyl($C_{0-3}$)alkyl, hetero($C_{5-12}$)cycloalkyl($C_{0-3}$)alkyl, ($C_{6-12}$)aryl($C_{0-3}$)alkyl, hetero($C_{5-12}$)aryl($C_{0-3}$)alkyl, ($C_{9-12}$)bicycloaryl($C_{0-3}$)alkyl or hetero($C_{8-12}$)bicycloaryl($C_{0-3}$)alkyl or (iii) ($C_{3-6}$)cycloalkyl($C_{0-3}$)alkyl, hetero($C_{5-6}$)cycloalkyl($C_{0-3}$)alkyl, phenyl($C_{0-3}$)alkyl or hetero($C_{5-6}$)aryl($C_{0-3}$)alkyl substituted by —$X^6OR^{15}$, —$X^6SR^{15}$, —$X^6S(O)R^{15}$, —$X^6S(O)_2R^{15}$, —$X^6C(O)R^{15}$, —$X^6C(O)OR^{15}$, —$X^6C(O)NR^{15}R^{16}$, —$X^6NR^{15}R^{16}$, —$X^6NR^{16}C(O)R^{15}$, —$X^6NR^{16}C(O)OR^{15}$, —$X^6NR^{16}C(O)NR^{15}R^{16}$, —$X^6NR^{16}C(O)OR^{16}$, —$X^6NR^{16}C(NR^{16})NR^{15}R^{16}$, wherein $X^6$ is a bond or methylene, $R^{15}$ is ($C_{3-6}$)cycloalkyl($C_{0-3}$)alkyl, hetero($C_{5-6}$)cycloalkyl($C_{0-3}$)alkyl, phenyl($C_{0-3}$)alkyl or hetero($C_{5-6}$)aryl($C_{0-3}$)alkyl and $R^{16}$ is hydrogen or ($C_{1-6}$)alkyl; wherein $R^4$ optionally further contains 1 to 5 substituents which when occurring within an alicyclic or aromatic ring system are radicals independently selected from a group consisting of ($C_{1-6}$)alkyl, ($C_{1-6}$)alkylidene, cyano, halo, nitro, halo-substituted ($C_{1-3}$)alkyl, —$X^6NR^{17}R^{17}$, —$X^6NR^{17}C(O)OR^{17}$, —$X^6NR^{17}C(O)NR^{17}R^{17}$, —$X^6NR^{17}C(NR^{17})NR^{17}R^{17}$, —$X^6OR^{17}$, —$X^6SR^{17}$, —$X^6C(O)OR^{17}$, —$X^6C(O)NR^{17}R^{17}$, —$X^6S(O)_2NR^{17}R^{17}$, —$X^6P(O)(OR^{18})OR^{17}$, —$X^6OP(O)(OR^{18})OR^{17}$, —$X^6NR^{17}C(O)R^{18}$, —$X^6S(O)R^{18}$, —$X^6S(O)_2R^{18}$ and —$X^6C(O)R^{18}$ and when occurring within an aliphatic moiety are radicals independently selected from a group consisting of cyano, halo, nitro, —$NR^{17}R^{17}$, —$NR^{17}C(O)OR^{17}$, —$NR^{17}C(O)NR^{17}R^{17}$, —$NR^{17}C(NR^{17})NR^{17}R^{17}$, —$OR^{17}$, —$SR^{17}$, —$C(O)OR^{17}$, —$C(O)NR^{17}R^{17}$, —$S(O)_2NR^{17}R^{17}$, —$P(O)(OR^{17})OR^{17}$, —$OP(O)(OR^{17})OR^{17}$, —$NR^{17}C(O)R^{18}$, —$S(O)R^{18}$, —$S(O)_2R^{18}$ and —$C(O)R^{18}$, wherein $X^6$ is a bond or ($C_{1-6}$)alkylene, $R^{17}$ at each occurrence independently is hydrogen, ($C_{1-6}$)alkyl or halo-substituted ($C_{1-3}$)alkyl and $R^{18}$ is ($C_{1-6}$)alkyl or halo-substituted ($C_{1-3}$)alkyl;

$R^{20}$ is selected from the group consisting of hydrogen, ($C_{1-6}$)alkyl, ($C_{3-12}$)cycloalkyl($C_{0-6}$)alkyl, hetero($C_{5-12}$)cycloalkyl($C_{0-6}$)alkyl, ($C_{6-12}$)aryl($C_{0-6}$)alkyl or hetero($C_{5-12}$)aryl($C_{0-6}$)alkyl;

$R^{23}$ is selected from hydrogen, ($C_{1-6}$)alkyl, alkoxy($C_{1-3}$)alkyl, halo($C_{1-3}$)alkyl, ($C_{3-12}$)cycloalkyl($C_{0-6}$)alkyl, hetero($C_{5-12}$)cycloalkyl($C_{0-6}$)alkyl, ($C_{6-12}$)aryl($C_{0-6}$)alkyl and hetero($C_{5-12}$)aryl($C_{0-6}$)alkyl optionally substituted with amino, —$NHC(O)R^{15}$ or —$R^{15}$ wherein $R^{15}$ is as described above; and $R^{24}$ is selected from hydrogen or ($C_{1-6}$)alkyl; or $R^{23}$ and $R^{24}$ taken together with the carbon atom to which both $R^{23}$ and $R^{24}$ are attached form ($C_{3-8}$)cycloalkylene or ($C_{3-8}$)heterocycloalkylene;

$X^3$ is selected from group (a), (b) or (c);

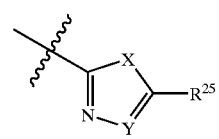

(a)

(b)

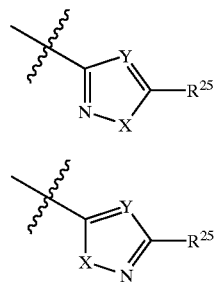

(c)

wherein X is O and Y is N;
$R^{25}$ is selected from hydrogen, $(C_{1-6})$alkyl, $(C_{3-12})$cycloalkyl$(C_{0-6})$alkyl, hetero$(C_{3-12})$cycloalkyl$(C_{0-6})$alkyl, $(C_{6-12})$aryl$(C_{0-6})$alkyl, hetero$(C_{5-13})$aryl$(C_{0-6})$alkyl, —$X^4$NHR$^{15}$, —$X^4$S(O)$_2$R$^{26}$ or —$X^4$C(O)R$^{17}$NR$^{17}$C(O)R$^{17}$ wherein $R^{15}$, $R^{17}$ and $X^4$ are as described above;
$R^{26}$ is selected from the group consisting of hydrogen, $(C_{1-6})$alkyl, $(C_{3-12})$cycloalkyl$(C_{0-6})$alkyl, hetero$(C_{5-12})$cycloalkyl$(C_{0-6})$alkyl, $(C_{6-12})$aryl$(C_{0-6})$alkyl, hetero$(C_{5-12})$aryl$(C_{0-6})$alkyl, $(C_{9-12})$bicycloaryl$(C_{0-3})$alkyl and hetero$(C_{8-12})$-bicycloaryl$(C_{0-3})$alkyl;
wherein $R^{25}$ optionally further contains 1 to 5 substituents which when occurring within an alicyclic or aromatic ring system are radicals independently selected from a group consisting of $(C_{1-6})$alkyl, $(C_{1-6})$alkylidene, cyano, halo, nitro, halo-substituted $(C_{1-3})$alkyl, —$X^6$NR$^{17}$R$^{17}$, —$X^6$NR$^{17}$C(O)OR$^{17}$, —$X^6$NR$^{17}$C(O)NR$^{17}$R$^{17}$, —$X^6$NR$^{17}$C(NR$^{17}$)NR$^{17}$R$^{17}$, —$X^6$OR$^{17}$, —$X^6$C(O)R$^{17}$, —$X^6$OR$^{15}$, —$X^6$SR$^{17}$, —$X^6$C(O)OR$^{17}$, —$X^6$C(O)NR$^{17}$R$^{17}$, —$X^6$S(O)$_2$NR$^{17}$R$^{17}$, —$X^6$P(O)(OR$^8$)OR$^{17}$, —$X^6$OP(O)(OR$^8$)OR$^{17}$, —$X^6$NR$^{17}$C(O)R$^{18}$, —$X^6$S(O)R$^{18}$, —$X^6$S(O)$_2$R$^{18}$ and —$X^6$C(O)R$^{18}$ and when occurring within an aliphatic moiety are radicals independently selected from a group consisting of cyano, halo, nitro, —NR$^{17}$R$^{17}$, —NR$^{17}$C(O)OR$^{17}$, —NR$^{17}$C(O)NR$^{17}$R$^{17}$, —NR$^{17}$C(NR$^{17}$)NR$^{17}$R$^{17}$, —OR$^{17}$, —SR$^{17}$, —C(O)OR$^{17}$, —C(O)NR$^{17}$R$^{17}$, —S(O)$_2$NR$^{17}$R$^{17}$, —P(O)(OR$^{17}$)OR$^{17}$, —OP(O)(OR$^{17}$)OR$^{17}$, —NR$^{17}$C(O)R$^{18}$, —S(O)R$^{18}$, —S(O)$_2$R$^{18}$ and —C(O)R$^{18}$, wherein $R^{15}$, $R^{17}$, $R^{18}$ and $X^6$ are as described above.

A second aspect of the invention is a pharmaceutical composition that contains a compound of Formula (I) or their N-oxide derivatives, individual isomers or mixture of isomers thereof, or pharmaceutically acceptable salts thereof, in admixture with one or more suitable excipients.

A third aspect of the invention is a method for treating a disease in an animal in which inhibition of cathepsin S can prevent, inhibit or ameliorate the pathology and/or symptomatology of the disease, which method comprises administering to the animal a therapeutically effective amount of compound of Formula (I) or a N-oxide derivative, individual isomer or mixture of isomers thereof; or a pharmaceutically acceptable salt thereof.

A fourth aspect of the invention is the processes for preparing compounds of Formula (I) and the N-oxide derivatives, prodrug derivatives, protected derivatives, individual isomers and mixtures of isomers thereof; and the pharmaceutically acceptable salts thereof.

DETAILED DESCRIPTION OF THE INVENTION

Definitions:
Unless otherwise stated, the following terms used in the specification and claims are defined for the purposes of this Application and have the following meanings.

"Alicyclic" means a moiety characterized by arrangement of the carbon atoms in closed non-aromatic ring structures having properties resembling those of aliphatics and may be saturated or partially unsaturated with two or more double or triple bonds.

"Aliphatic" means a moiety characterized by a straight or branched chain arrangement of the constituent carbon atoms and may be saturated or partially unsaturated with two or more double or triple bonds.

"Alkoxy" means an alkyl-O-group in which the alkyl group is as described herein. Exemplary alkoxy groups include methoxy and ethoxy.

"Alkyl" represented by itself means a straight or branched, saturated or unsaturated, aliphatic radical having the number of carbon atoms indicated (e.g., $(C_{1-6})$alkyl includes methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl) means a straight or branched, saturated or unsaturated aliphatic divalent radical having the number of atoms indicated or when no atoms are indicated means a bond (e.g., $(C_{6-10})$aryl$(C_{0-3})$alkyl includes phenyl, benzyl, phenethyl, 1-phenylethyl 3-phenylpropyl, and the like).

"Alkylene", unless indicated otherwise, means a straight or branched, saturated or unsaturated, aliphatic, divalent radical having the number of carbon atoms indicated (e.g., $(C_{1-6})$alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—) 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like).

"Alkylidene" means a straight or branched saturated or unsaturated, aliphatic, divalent radical having the number of carbon atoms indicated (e.g. $(C_{1-6})$alkylidene includes methylene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like).

"Amino" means the radical —NH$_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2.

"Aryl" means a monocyclic or fused bicyclic ring assembly containing the total number of ring carbon atoms indicated, wherein each ring is comprised of 6 ring carbon atoms and is aromatic or when fused with a second ring forms an aromatic ring assembly. For example, optionally substituted $(C_{6-10})$aryl as used in this Application includes, but is not limited to, biphenyl-2-yl, 2-bromophenyl, 2-bromocarbonylphenyl, 2-bromo-5-fluorophenyl, 4-tert-butylphenyl, 4-carbamoylphenyl, 4-carboxy-2-nitrophenyl, 2-chlorophenyl, 4-chlorophenyl, 3-chlorocarbonylphenyl, 4-chlorocarbonylphenyl, 2-chloro-4-fluorophenyl, 2-chloro-6-fluorophenyl, 4-chloro-2-nitrophenyl, 6-chloro-2-nitrophenyl, 2,6-dibromophenyl, 2,3-dichlorophenyl, 2,5-dichlorophenyl, 3,4-dichlorophenyl, 2-difluoromethoxyphenyl, 3,5-dimethylphenyl, 2-ethoxycarbonylphenyl, 2-fluorophenyl, 2-iodophenyl, 4-isopropylphenyl, 2-methoxyphenyl, 4-methoxyphenyl, 2-methylphenyl, 3-methylphenyl, 4-methylphenyl, 5-methyl-2-nitrophenyl, 4-methylsulfonylphenyl, naphth-2-yl, 2-nitrophenyl, 3-nitrophenyl, 4-nitrophenyl, 2,3,4,5,6-pentafluorophenyl, phenyl, 2-trifluoromethoxyphenyl, 3-trifluoromethoxyphenyl, 4-trifluoromethoxyphenyl, 2-trifluoromethylphenyl, 3-trifluoromethylphenyl, 4-trifluoromethylphenyl, 2-trifluoromethylsulfanylphenyl, 4-trifluoromethylsulfanylphenyl, and the like. Optionally substituted ($C_{6-10}$)aryl as used in this Application includes 3-acetylphenyl, 3-tert-butoxycarbonylaminomethylphenyl, biphenyl-4-yl, 3-hydroxyphenyl, 4-hydroxyphenyl, 3-methoxyphenyl, naphth-2-yl, 3-phenoxyphenyl, phenyl, and the like.

"Bicycloaryl" means a bicyclic ring assembly containing the number of ring carbon atoms indicated, wherein the rings are linked by a single bond or fused and at least one of the rings comprising the assembly is aromatic, and any carbocyclic ketone, thioketone or iminoketone derivative thereof (e.g., ($C_{9-10}$)bicycloaryl includes cyclohexylphenyl, 1,2-dihydronaphthyl, 2,4-dioxo-1,2,3,4-tetrahydronaphthyl, indanyl, indenyl, 1,2,3,4-tetrahydronaphthyl, and the like).

"Carbamoyl" means the radical —C(O)NH$_2$. Unless indicated otherwise, the compounds of the invention containing carbamoyl moieties include protected derivatives thereof. Suitable protecting groups for carbamoyl moieties include acetyl, tert-butoxycarbonyl, benzyloxycarbonyl, and the like and both the unprotected and protected derivatives fall within the scope of the invention.

"Carbocyclic ketone derivative" means a derivative containing the moiety —C(O)—.

"Carboxy" means the radical —C(O)OH. Unless indicated otherwise, the compounds of the invention containing carboxy moieties include protected derivatives thereof. Suitable protecting groups for carboxy moieties include benzyl, tert-butyl, and the like.

"Cycloalkyl" means a saturated or partially unsaturated, monocyclic, fused bicyclic or bridged polycyclic ring assembly containing the number of ring carbon atoms indicated, and any carbocyclic ketone, thioketone or iminoketone derivative thereof (e.g., ($C_{3-10}$)cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like).

"Cycloalkylene" means a divalent saturated or partially unsaturated, monocyclic ring or bridged polycyclic ring assembly containing the number of ring carbon atoms indicated, and any carbocyclic ketone, thioketone or iminoketone derivative thereof.

"Disease" specifically includes any unhealthy condition of an animal or part thereof and includes an unhealthy condition that may be caused by, or incident to, medical or veterinary therapy applied to that animal, i.e., the "side effects" of such therapy.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g. halo-substituted ($C_{1-3}$)alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroaryl" means aryl, as defined in this Application, provided that one or more of the ring carbon atoms indicated are replaced by a heteroatom moiety selected from —N═, —NR—, —N$^+$(O$^-$)═, —O— or —S—, wherein R is hydrogen, ($C_{1-6}$)alkyl, a protecting group or represents the free valence which serves as the point of attachment to a ring nitrogen, and each ring is comprised of 5 or 6 ring atoms. For example, optionally substituted hetero($C_{5-13}$)aryl as used in this Application includes, but is not limited to, 4-amino-2-hydroxypyrimidin-5-yl, benzothiazol-2-yl, 1H-benzoimidazol-2-yl, 2-bromopyrid-5-yl, 5-bromopyrid-2-yl, 4-carbamoylthiazol-2-yl, 3-carboxypyrid-4-yl, 5-carboxy-2,6-dimethylpyrid-3-yl, dibenzofuranyl, 3,5-dimethylisoxazol-4-yl, 5-ethoxy-2,6-dimethylpyrid-3-yl, 5-fluoro-6-hydroxypyrimidin-4-yl, fur-2-yl, fur-3-yl, 5-hydroxy-4,6-dimethylpyrid-3-yl, 8-hydroxy-5,7-dimethylquinolin-2-yl, 5-hydroxymethylisoxazol-3-yl, 3-hydroxy-6-methylpyrid-2-yl, 3-hydroxypyrid-2-yl, 1H-imidazol-2-yl, 1H-imidazol-4-yl, 1H-indol-3-yl, isothiazol-4-yl, isoxazol-4-yl, 2-methylfur-3-yl, 5-methylfur-2-yl, 1-methyl-1H-imidazol-2-yl, 5-methyl-3H-imidazol-4-yl, 5-methylisoxazol-3-yl, pyrazinyl, 5-methyl-2H-pyrazol-3-yl, 3-methylpyrid-2-yl, 4-methylpyrid-2-yl, 5-methylpyrid-2-yl, 6-methylpyrid-2-yl, 2-methylpyrid-3-yl, 2-methylthiazol-4-yl, 5-nitropyrid-2-yl, 2H-pyrazol-3-yl, 3H-pyrazol-4-yl, pyridazin-3-yl, pyrid-2-yl, pyrid-3-yl, pyrid-4-yl, 5-pyrid-3-yl-2H-[1,2,4] triazol-3-yl, pyrimidin-4-yl, pyrimidin-5-yl, 1H-pyrrol-3-yl, quinolin-2-yl, 1H-tetrazol-5-yl, thiazol-2-yl, thiazol-5-yl, thien-2-yl, thien-3-yl, 2H-[1,2,4]triazol-3-yl, 3H-[1,2,3] triazol-4-yl, 5-trifluoromethylpyrid-2-yl, and the like. Suitable protecting groups include tert-butoxycarbonyl, benzyloxycarbonyl, benzyl, 4-methoxybenzyl, 2-nitrobenzyl, and the like. Optionally substituted hetero ($C_{5-10}$)aryl as used in this Application to define R$^4$ includes benzofur-2-yl, fur-2-yl, fur-3-yl, pyrid-3-yl, pyrid-4-yl, quinol-2-yl, quinol-3-yl, thien-2-yl, thien-3-yl, and the like.

"Heteroatom moiety" includes —N═, —NR—, —N$^+$(O$^-$)═, —O—, —S— or —S(O)$_2$—, wherein R is hydrogen, ($C_{1-6}$)alkyl or a protecting group.

"Heterobicycloaryl" means bicycloaryl, as defined in this Application, provided that one or more of the ring carbon atoms indicated are replaced by a heteroatom moiety selected from —N═, —NR—, —O— or —S—, wherein R is hydrogen, ($C_{1-6}$)alkyl, a protecting group or represents the free valence which serves as the point of attachment to a ring nitrogen, and any carbocyclic ketone, thioketone or iminoketone derivative thereof. For example, optionally substituted hetero($C_{8-10}$)bicycloaryl as used in this Application includes, but is not limited to, 2-amino-4-oxo-3,4-dihydropteridin-6-yl, and the like. In general, the term heterobicycloaryl as used in this Application includes, for example, benzo[1,3]dioxol-5-yl, 3,4-dihydro-2H-[1,8] naphthyridinyl, 3,4-dihydro-2H-quinolinyl, 2,4-dioxo-3,4-dihydro-2H-quinazolinyl, 1,2,3,4,5,6-hexahydro[2,2'] bipyridinylyl, 3-oxo-2,3-dihydrobenzo[1,4]oxazinyl, 5,6,7, 8-tetrahydroquinolinyl, and the like.

"Heterocycloalkyl" means cycloalkyl, as defined in this Application, provided that one or more of the ring carbon atoms indicated are replaced by a heteroatom moiety selected from —N═, —NR—, —O— or —S—, wherein R is hydrogen, ($C_{1-6}$)alkyl, a protecting group or represents the free valence which serves as the point of attachment to a ring nitrogen, and any carbocyclic ketone, thioketone or iminoketone derivative thereof (e.g., the term hetero($C_{5-10}$) cycloalkyl includes imidazolidinyl, morpholinyl, piperazinyl, piperidyl, pyrrolidinyl, pyrrolinyl, quinuclidinyl, and the like). Suitable protecting groups include tert-butoxycarbonyl, benzyloxycarbonyl, benzyl, 4-methoxybenzyl, 2-nitrobenzyl, and the like. Both the unprotected and protected derivatives fall within the scope of the invention.

"Heterocycloalkylene" means cycloalkylene, as defined in this Application, provided that one or more of the ring member carbon atoms indicated, is replaced by heteroatom moiety selected from —N=, —NR—, —O—, —S— or —S(O)$_2$—, wherein R is hydrogen, (C$_{1-6}$)alkyl or a protecting group.

"Hydroxy" means the radical —OH. Unless indicated otherwise, the compounds of the invention containing hydroxy radicals include protected derivatives thereof. Suitable protecting groups for hydroxy moieties include benzyl and the like.

"Iminoketone derivative" means a derivative containing the moiety —C(NR)—, wherein R is hydrogen or (C$_{1-6}$) alkyl.

"Isomers" mean compounds of Formula (I) having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute, configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula (I) are meant to be encompassed all possible stereoisomers. Thus, for example, the name morpholine-4-carboxylic acid {2-phenylmethanesulfonyl-1-[1-(5-phenyl-[1,3,4] oxadiazole-2-carbonyl)-pentylcarbamoyl]-ethyl}-amide is meant to include morpholine-4-carboxylic acid {S-2-phenylmethanesulfonyl-1-[1-(5-phenyl-[1,3,4]oxadiazole-2-carbonyl)-pentylcarbamoyl]-ethyl}-amide and morpholine-4-carboxylic acid {R-2-phenylmethanesulfonyl-1-[1-(5-phenyl-[1,3,4]oxadiazole-2-carbonyl)-pentylcarbamoyl]-ethyl}-amide and any mixture, racemic or otherwise, thereof.

"Ketone derivative" means a derivative containing the moiety —C(O)—. For example, for 2-acetoxy-azetidin-3-yl, the "carbocyclic ketone derivative" would be 2-acetoxy-4-oxo-azetidin-3-yl.

"Nitro" means the radical —NO$_2$.

"Optional" or "optionally" means that the subsequently described event or circumstance may or may not occur, and that the description includes instances where the event or circumstance occurs and instances in which it does not. For example, the phrase "wherein within $R^3$ and $R^4$ any alicyclic or aromatic ring system may be substituted further by 1–5 radicals . . . " means that $R^3$ and $R^4$ may or may not be substituted in order to fall within the scope of the invention.

"Oxoalkyl" means alkyl, as defined above, wherein one of the number of carbon atoms indicated is replaced by an oxygen group (—O—), e.g., oxo(C$_{2-6}$)alkyl includes methoxymethyl, etc.

"N-oxide derivatives" means derivatives of compounds of Formula (I) in which nitrogens are in an oxidized state (i.e. O—N) and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula (I) which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanotlamine, diethanolamine, triethanolamine, tromethamine, N-methylglucamine and the like.

"Prodrug" means a compound that is convertible in vivo by metabolic means (e.g. by hydrolysis) to a compound of Formula I. For example an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. Suitable esters of compounds of Formula (I) containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulphonates, ethanesulphonates, benzenesulfonate, p-toluenesulphonates, cyclohexylsulphamates and quinates. Suitable esters of compounds of Formula (I) containing a carboxy group, are for example those described by F. J. Leinweber, Drug Metab. Res., 1987, 18, page 379. An especially useful class of esters of compounds of Formula (I) containing a hydroxy group, may be formed from acid moieties selected from those described by Bundgaard et al., J. Med. Chem., 1989, 32, page 2503–2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of Formula (I) in which a reactive site or sites are blocked with protecting groups. Protected derivatives of compounds of Formula (I) are useful in the preparation of compounds of Formula (I) or in themselves may be active cathepsin S inhibitors. A comprehensive list of suitable protecting groups can be found in T. W. Greene, *Protecting Groups in Organic Synthesis*, 3rd edition, John Wiley & Sons, Inc. 1999.

"Therapeutically effective amount" means that amount which, when administered to an animal for treating a disease, is sufficient to effect such treatment for the disease.

"Thioketone derivative" means a derivative containing the moiety —C(S)—.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

Nomenclature:

The compounds of Formula (I) and the intermediates and starting materials used in their preparation are named in accordance with IUPAC rules of nomenclature in which the characteristic groups have decreasing priority for citation as the principle group as follows: acids, esters, amides, etc. Alternatively, the compounds are named by AutoNom 4.0 (Beilstein Information Systems, Inc.). For example, a compound of Formula (I) in which $R^3$ is phenyl, $R^4$ is morpholine-4-carbonyl, $R^{20}$ is hydrogen, $R^{23}$ is hydrogen, $R^{24}$ is n-butyl, $X^1$ is methylene, $X^2$ is methylene and $X^3$ is 5-pyridin-3-yl-[1,3,4]oxadiazol-2-yl; that is, a compound having the following structure:

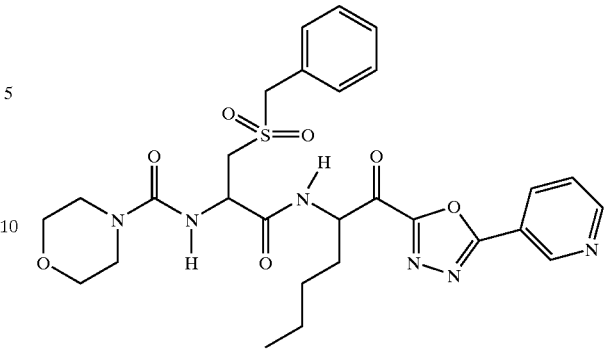

is named morpholine-4-carboxylic acid {2-phenylmethanesulfonyl-1-[1-(5-pyridin-3-yl-[1,3,4]oxadiazole-2-carbonyl)-pentylcarbamoyl]-ethyl}-amide.

With reference to formula (I) above, the following are particular and preferred groupings:

$X^1$ may particularly represent methylene when $X^2$ is methylene.

$X^1$ may also particularly represent ethylene when $X^2$ is a bond.

$X^3$ may particularly represent

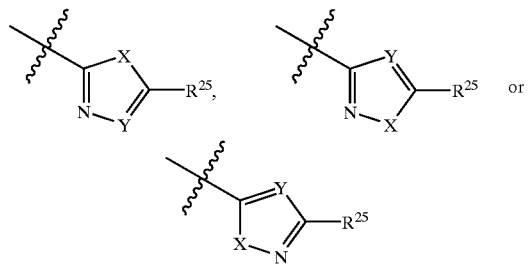

wherein X is O, Y is N and $R^{25}$ is selected from hydrogen, halo($C_{1-3}$)alkyl, ($C_{1-6}$)alkyl, ($C_{3-12}$)cycloalkyl($C_{0-6}$)alkyl, ($C_{6-12}$)aryl($C_{0-6}$)alkyl or hetero($C_{5-13}$)aryl($C_{0-6}$)alkyl, wherein $R^{25}$ optionally further contains 1 to 5 substituents which when occurring within an alicyclic or aromatic ring system are radicals independently selected from a group consisting of ($C_{1-6}$)alkyl or halo-substituted ($C_{1-3}$)alkyl.

$R^3$ may particularly represent —$CR^5$=$CHR^6$, —$CR^5(CR^6{}_3)_2$, —$CR^7$=$NR^8$, or ($C_{3-12}$)cycloalkyl, wherein $R^5$ and $R^6$ is independently hydrogen or ($C_{1-4}$)alkyl or $R^5$ and $R^6$ together with the atoms to which $R^5$ and $R^6$ are attached form ($C_{3-12}$)cycloalkyl, ($C_{6-12}$)aryl, hetero($C_{5-12}$)aryl or ($C_{9-12}$)bicycloaryl and $R^7$ and $R^8$ together with the atoms to which $R^7$ and $R^8$ are attached form hetero($C_{5-12}$)aryl, wherein $R^3$ optionally is substituted by 1 to 5 radicals independently selected from a group consisting of ($C_{1-4}$)alkyl, cyano, halo, halo-substituted ($C_{1-4}$)alkyl, —$X^4OR^9$ and —$X^4C(O)OR^9$, in which $X^4$ is a bond or ($C_{1-2}$)alkylene, $R^9$ at each occurrence independently is ($C_{1-3}$)alkyl or halo-substituted ($C_{1-3}$)alkyl.

$R^4$ may particularly represent —$C(O)X^5R^{11}$ or —$S(O)_2X^5R^{11}$, wherein $X^5$ is a bond, —O— or —$NR^{12}$—, wherein $R^{12}$ is hydrogen or ($C_{1-6}$)alkyl, and $R^{11}$ is (i) ($C_{1-6}$)alkyl or (ii) hetero($C_{5-12}$)cycloalkyl($C_{0-3}$)alkyl, ($C_{6-12}$)aryl($C_{0-3}$)alkyl, hetero($C_{5-12}$)aryl($C_{0-3}$)alkyl, ($C_{9-12}$)bicycloaryl($C_{0-3}$)alkyl or hetero($C_{8-12}$)bicycloaryl($C_{0-3}$)alkyl or (iii) hetero ($C_{5-6}$)cycloalkyl($C_{0-3}$)alkyl or phenyl($C_{0-3}$)alkyl substituted by —$X^6OR^{15}$, —$X^6C(O)R^{15}$ or —$X^6NR^{16}C(O)OR^{16}$, wherein $X^6$ is a bond or methylene, $R^{15}$ is phenyl($C_{0-3}$)alkyl or hetero($C_{5-6}$)aryl($C_{0-3}$)alkyl and $R^{16}$ is hydrogen or ($C_{1-6}$)alkyl; wherein $R^4$ optionally further contains 1 to 5 substituents which when occurring within an alicyclic or aromatic ring system are radicals independently selected from a group consisting of ($C_{1-6}$)alkyl, halo, —$X^6NR^{17}R^{17}$, —$X^6OR^{17}$, —$X^6C(O)OR^{17}$, —$X^6NC(O)R^{16}$ and —$X^6C(O)R^{18}$, $R^{17}$ at each occurrence independently is hydrogen, ($C_{1-6}$)alkyl or halo-substituted ($C_{1-3}$)alkyl and $R^{18}$ is ($C_{1-6}$)alkyl or halo-substituted ($C_{1-3}$)alkyl.

$R^{20}$ may particularly represent hydrogen and ($C_{1-6}$)alkyl.

$R^{23}$ may particularly represent ($C_{1-6}$)alkyl or ($C_{6-12}$)aryl ($C_{0-6}$)alkyl.

$R^{24}$ may particularly represent hydrogen or ($C_{1-6}$)alkyl.

$X^3$ more preferably is selected from the group consisting of

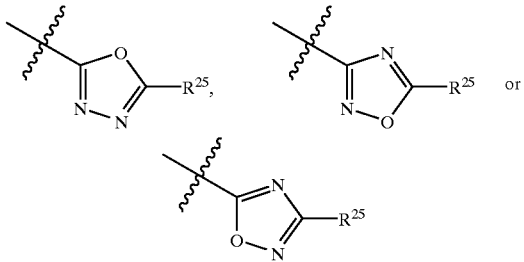

wherein $R^{25}$ is selected from tert-butyl, cyclopropyl, ethyl, phenyl, pyrazinyl, pyridazinyl, pyridinyl, thienyl or trifluoromethyl.

$R^3$ more preferably is selected from the group consisting of phenyl, pyridin-2-yl, pyridin-3-yl, pyridin-4-yl, vinyl, 2-difluoromethoxyphenyl, 1-oxy-pyridin-2-yl, 4-methoxyphenyl, 4-methylphenyl, 2-methylphenyl, 4-chlorophenyl, 3,5-dimethylphenyl, 4-trifluoromethylphenyl, 4-trifluoromethoxyphenyl, 2-bromophenyl, naphthalen-2-yl, 3,4-dichlorophenyl, 3-methylphenyl, 3-trifluoromethylphenyl, 3-trifluoromethoxyphenyl, 2,3,4,5,6-pentafluoro-phenyl, 2-fluorophenyl, 2-chlorophenyl, 2-cyano-phenyl, 2-trifluoromethylphenyl, 4-tert-butyl-phenyl, 3-chlorophenyl, 4-bromophenyl, 2-fluoro-3-chloro-phenyl, 2-fluoro-3-methyl-phenyl, 3-fluorophenyl, 2,5-difluorophenyl, 3-bromophenyl, 2,5-dichlorophenyl, 2,6-difluorophenyl, 3-cyano-phenyl, 4-cyano-phenyl, 2-trifluoromethoxyphenyl, 2,3-difluorophenyl, biphenyl, 2-bromo-5-fluoro-phenyl, 4-fluorophenyl, 3,4-difluorophenyl, 2,4-difluorophenyl, 2,4,6-trifluorophenyl, 2,4,5-trifluorophenyl, 2,3,4-trifluorophenyl, 2-chloro-5-trifluoromethylphenyl, 2,4-bis-trifluoromethylphenyl, 2,5,6-trifluorophenyl, 2-fluoro-3-trifluoromethylphenyl, 2-fluoro-4-trifluoromethylphenyl, 2-fluoro-5-trifluoromethylphenyl, 2,3,5-trifluorophenyl, 2-fluoro-5-trifluoromethylphenyl, 5-fluoro-2-trifluoromethylphenyl, 4-fluoro-3-trifluoromethylphenyl, 2-methoxyphenyl, 3,5-bis-trifluoromethylphenyl, 4-difluoromethoxyphenyl, 3-difluoromethoxyphenyl, 2,6-dichlorophenyl, 4-carboxyphenyl, cyclohexyl, cyclopropyl, isopropyl, thiophen-2-yl, 5-chloro-thiophen-2-yl and 3,5-dimethyl-isoxazol-4-yl. Most preferred $R^3$ groups include cyclopropyl, isopropyl and phenyl.

$R^4$ more preferably is selected from the group consisting of benzoyl, morpholine-4-carbonyl, acetyl, furan-3-carbonyl, 2-methoxy-benzoyl, 3-methoxy-benzoyl, naphthalene-2-carbonyl, benzo[1,3]dioxole-5-carbonyl, 3-pyridin-3-yl-acryloyl, benzofuran-2-carbonyl, furan-2-carbonyl, tert-butoxy-carbonyl, biphenyl-4-carbonyl, quinoline-2-carbonyl, quinoline-3-carbonyl, 3-acetyl-benzoyl, 4-phenoxy-benzoyl, 3-hydroxy-benzoyl, 4-hydroxy-benzoyl, pyridine-3-carbonyl, 3-(tert-butoxycarbonylamino-methyl)-benzoyl, 4-carbonyl-piperazine-1-carboxylic acid tert-butyl ester, 4-carbonyl-piperazine-1-carboxylic acid ethyl ester, 4-(furan-2-carbonyl)-piperazine-1-carbonyl, pyridine-4-carbonyl, 1-oxy-pyridine-4-carbonyl, 1-oxy-pyridine-3-carbonyl, thiophene-2-carbonyl, thiophene-3-carbonyl, 4-benzoyl-benzoyl, 5-methyl-thiophene-2-carbonyl, 3-chloro-thiophene-2-carbonyl, 3-bromo-thiophene-2-carbonyl, 4-chloro-benzoyl, 3-flouro-4-methoxy-benzoyl, 4-methoxy-benzoyl, 4-triflouromethoxy-benzoyl, 3,4-diflouro-benzoyl, 4-fluoro-benzoyl, 3,4-dimethoxy-benzoyl, 3-methyl-benzoyl, 4-bromo-benzoyl, 4-triflouromethyl-benzoyl, 3-benzoyl-benzoyl, cyclopentane-carbonyl, benzo[b]thiophene-2-carbonyl, 3-chloro-benzo[b]thiophene-2-carbonyl, benzenesulfonyl, naphthalene-2-sulfonyl, 5-methyl-thiophene-2-sulfonyl, thiophene-2-sulfonyl, formamyl-methyl ester, 4-methyl-pentanoyl, formamyl-isobutyl ester, formamyl-monoallyl ester, formamyl-isopropyl ester, N,N-dimethyl-formamyl, N-isopropyl-formamyl, N-pyridin-4-yl-formamyl, N-pyridin-3-yl-formamyl, 3-phenyl-acryloyl, 1H-indole-5-carbonyl, pyridine-2-carbonyl, pyrazine-2-carbonyl, 3-hydroxy-pyridine-2-carbonyl, 2-amino-pyridine-3-carbonyl, 2-hydroxy-pyridine-3-carbonyl, 6-amino-pyridine-3-carbonyl, 6-hydroxy-pyridine-3-carbonyl, pyridazine-4-carbonyl, 3-phenoxy-benzoyl and 1-oxo-1,3-dihydro-isoindole-2-carbonyl. $R^4$ is most preferably morpholine-4-carbonyl.

It is to be understood that this invention covers all appropriate combinations of the particular and preferred groupings referred to herein unless otherwise stated.

A particular preferred group of compounds of the invention are compounds of Formula (Ia):

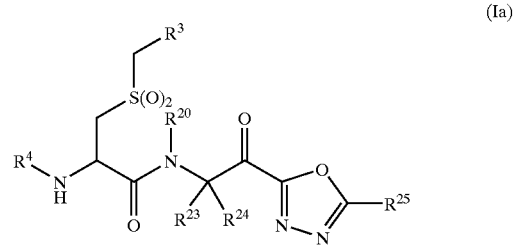

(Ia)

wherein $R^3$, $R^4$, $R^{20}$, $R^{23}$, $R^{24}$ and $R^{25}$ are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of Formula (Ia) and their N-oxides and their prodrugs, and their protected derivatives, individual isomers and mixtures of isomers thereof.

Compounds of Formula (Ia) in which $R^3$ is —$CR^5$=$CHR^6$ wherein $R^5$ and $R^6$ together with the atoms to which $R^5$ and $R^6$ are attached form ($C_{6-12}$)aryl, optionally substituted by 1 to 5 radicals independently selected from a group consisting of ($C_{1-4}$)alkyl, cyano, halo, halo-substituted ($C_{1-4}$)alkyl, —$X^4OR^9$ and —$X^4C(O)OR^9$, in which $X^4$ is a bond or ($C_{1-2}$)alkylene, $R^9$ at each occurrence independently is ($C_{1-3}$)alkyl or halo-substituted ($C_{1-3}$)alkyl, are preferred. Compounds of Formula (Ia) in which $R^3$ represents phenyl or 2-difluoromethoxyphenyl are especially preferred.

Compounds of Formula (Ia) in which $R^3$ is —$CR^5(CR^6_3)_2$ wherein $R^5$ is hydrogen and $R^6$ is ($C_{1-4}$)alkyl are also preferred. Compounds of Formula (Ia) in which $R^3$ represents —$CH(CH_3)_2$ are especially preferred.

Compounds of Formula (Ia) in which $R^3$ is $(C_{3-12})$ cycloalkyl are also preferred.

Compounds of Formula (Ia) in which $R^3$ represents cyclopropyl are especially preferred.

Compounds of Formula (Ia) in which $R^4$ is —$C(O)X^5R^{11}$ wherein $X^5$ is a bond and $R^{11}$ is hetero($C_{5-12}$)cycloalkyl($C_{0-3}$)alkyl, particularly hetero($C_{5-12}$)cycloalkyl, are preferred.

Compounds of Formula (Ia) in which $R^4$ represents

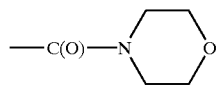

are especially preferred.

Compounds of Formula (Ia) in which $R^{20}$ is hydrogen are preferred.

Compounds of Formula (Ia) in which $R^{23}$ is $(C_{1-6})$alkyl [e.g. ethyl or butyl] are preferred.

Compounds of Formula (Ia) in which $R^{24}$ is hydrogen are preferred.

Compounds of Formula (Ia) in which $R^{25}$ is tert-butyl, cyclopropyl, ethyl, phenyl, pyridin-3-yl, pyridin-4-yl, thien-3-yl or trifluoromethyl are preferred.

A preferred group of compounds of the invention are compounds of Formula (Ia) in which: $R^3$ is —$CR^5$=$CHR^6$ [e.g. phenyl or 2-difluoromethoxyphenyl], —$CR^5(CR^6{}_3)_2$ or $(C_{3-12})$cycloalkyl [e.g. —$CH(CH_3)_2$ or cyclopropyl]; $R^4$ is —$C(O)X^5R^{11}$ [e.g.

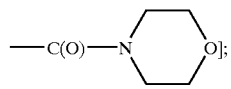

$R^{20}$ is hydrogen; $R^{23}$ is $(C_{1-6})$alkyl [e.g. ethyl or butyl]; $R^{24}$ is hydrogen; and $R^{25}$ is tert-butyl, cyclopropyl, ethyl, phenyl, pyridin-3-yl, pyridin-4-yl, thien-3-yl or trifluoromethyl, and their corresponding N-oxides, and their prodrugs, and their protected derivatives, individual isomers and mixtures of isomers thereof; and the pharmaceutically acceptable salts and solvates (e.g. hydrates) of such compounds of Formula (Ia) and their N-oxides and their prodrugs, and their protected derivatives, individual isomers and mixtures of isomers thereof.

A further particular preferred group of compounds of the invention are compounds of Formula (Ib):

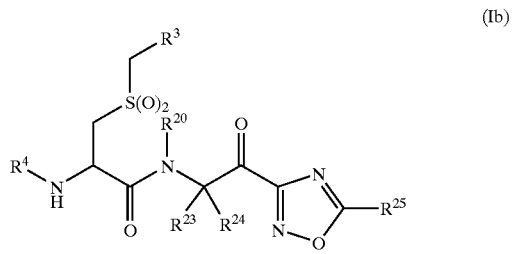

(Ib)

wherein $R^3$, $R^4$, $R^{20}$, $R^{23}$, $R^{24}$ and $R^{25}$ are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of Formula (Ib) and their N-oxides and their prodrugs, and their protected derivatives, individual isomers and mixtures of isomers thereof.

Compounds of Formula (Ib) in which $R^3$ is —$CR^5$=$CHR^6$ wherein $R^5$ and $R^6$ together with the atoms to which $R^5$ and $R^6$ are attached form $(C_{6-12})$aryl, optionally substituted by 1 to 5 radicals independently selected from a group consisting of $(C_{1-4})$alkyl, cyano, halo, halo-substituted $(C_{1-4})$alkyl, —$X^4OR^9$ and —$X^4C(O)OR^9$, wherein $X^4$ is a bond or $(C_{1-2})$alkylene, $R^9$ at each occurrence independently is $(C_{1-3})$alkyl or halo-substituted $(C_{1-3})$alkyl, are preferred. Compounds of Formula (Ib) in which $R^3$ represents phenyl or 2-difluoromethoxyphenyl are especially preferred.

Compounds of Formula (Ib) in which $R^3$ is —$CR^5(CR^6{}_3)_2$ wherein $R^5$ is hydrogen and $R^6$ is $(C_{1-4})$alkyl are also preferred. Compounds of Formula (Ib) in which $R^3$ represents —$CH(CH_3)_2$ are especially preferred.

Compounds of Formula (Ib) in which $R^3$ is $(C_{3-12})$ cycloalkyl are also preferred.

Compounds of Formula (Ib) in which $R^3$ represents cyclopropyl are especially preferred.

Compounds of Formula (Ib) in which $R^4$ is —$C(O)X^5R^{11}$ wherein $X^5$ is a bond and $R^{11}$ is hetero($C_{5-12}$)cycloalkyl($C_{0-3}$)alkyl, particularly hetero($C_{5-12}$)cycloalkyl, are preferred.

Compounds of Formula (Ib) in which $R^4$ represents

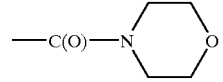

are especially preferred.

Compounds of Formula (Ib) in which $R^{20}$ is hydrogen are preferred.

Compounds of Formula (Ib) in which $R^{23}$ is $(C_{1-6})$alkyl [e.g. ethyl or butyl] are preferred.

Compounds of Formula (Ib) in which $R^{24}$ is hydrogen are preferred.

Compounds of Formula (Ib) in which $R^{25}$ is tert-butyl, cyclopropyl, ethyl, phenyl, pyridin-3-yl, pyridin-4-yl, thien-3-yl or trifluoromethyl are preferred.

A preferred group of compounds of the invention are compounds of Formula (Ib) in which: $R^3$ is —$CR^5$=$CHR^6$ [e.g. phenyl or 2-difluoromethoxyphenyl], —$CR^5(CR^6{}_3)_2$ or $(C_{3-12})$cycloalkyl [e.g. —$CH(CH_3)_2$ or cyclopropyl]; $R^4$ is —$C(O)X^5R^{11}$ [e.g.

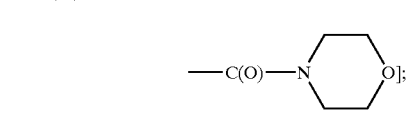

$R^{20}$ is hydrogen; $R^{23}$ is $(C_{1-6})$alkyl [e.g. ethyl or butyl]; $R^{24}$ is hydrogen; and $R^{25}$ is tert-butyl, cyclopropyl, ethyl, phenyl, pyridin-3-yl, pyridin-4-yl, thien-3-yl or trifluoromethyl, and their corresponding N-oxides, and their prodrugs, and their protected derivatives, individual isomers and mixtures of isomers thereof; and the pharmaceutically acceptable salts and solvates (e.g. hydrates) of such compounds of Formula (Ib) and their N-oxides and their prodrugs, and their protected derivatives, individual isomers and mixtures of isomers thereof.

A particular preferred group of compounds of the invention are compounds of Formula (Ic):

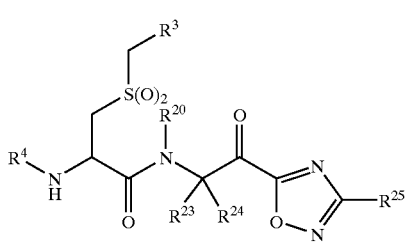
(Ic)

wherein R³, R⁴, R²⁰, R²³ R²⁴ and R²⁵ are as hereinbefore described, and their corresponding N-oxides, and their prodrugs, and their protected derivatives, individual isomers and mixtures of isomers thereof; and the pharmaceutically acceptable salts and solvates (e.g. hydrates) of such compounds of Formula (Ic) and their N-oxides and their prodrugs, and their protected derivatives, individual isomers and mixtures of isomers thereof.

Compounds of Formula (Ic) in which R³ is —CR⁵=CHR⁶ wherein R⁵ and R⁶ together with the atoms to which R⁵ and R⁶ are attached form $(C_{6-12})$aryl, optionally substituted by 1 to 5 radicals independently selected from a group consisting of $(C_{1-4})$alkyl, cyano, halo, halo-substituted $(C_{1-4})$alkyl, —X⁴OR⁹ and —X⁴C(O)OR⁹, wherein X⁴ is a bond or $(C_{1-2})$alkylene, R⁹ at each occurrence independently is $(C_{1-3})$alkyl or halo-substituted $(C_{1-3})$alkyl, are preferred. Compounds of Formula (Ic) in which R³ represents phenyl or 2-difluoromethoxyphenyl are especially preferred.

Compounds of Formula (Ic) in which R³ is —CR⁵(CR⁶₃)₂ wherein R⁵ is hydrogen and R⁶ is $(C_{1-4})$alkyl are also preferred. Compounds of Formula (Ic) in which R³ represents —CH(CH₃)₂ are especially preferred.

Compounds of Formula (Ic) in which R³ is —CR⁵(CR⁶₃)₂ wherein R⁵ and R⁶ together with the atoms to which R⁵ and R⁶ are attached form $(C_{3-12})$cycloalkyl are also preferred.

Compounds of Formula (Ic) in which R³ represents cyclopropyl are especially preferred.

Compounds of Formula (Ic) in which R⁴ is —C(O)X⁵R¹¹ wherein X⁵ is a bond and R¹¹ is hetero$(C_{5-12})$cycloalkyl$(C_{0-3})$alkyl, particularly hetero$(C_{5-12})$cycloalkyl, are preferred.

Compounds of Formula (Ic) in which R⁴ represents

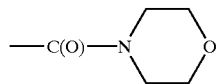

are especially preferred.

Compounds of Formula (Ic) in which R²⁰ is hydrogen are preferred.

Compounds of Formula (Ic) in which R²³ is $(C_{1-6})$alkyl [e.g. ethyl or butyl]are preferred.

Compounds of Formula (Ic) in which R²⁴ is hydrogen are preferred.

Compounds of Formula (Ic) in which R²⁵ is tert-butyl, cyclopropyl, ethyl, phenyl, pyridin-3-yl, pyridin-4-yl, thien-3-yl or trifluoromethyl are preferred.

A preferred group of compounds of the invention are compounds of Formula (Ic) in which: R³ is —CR⁵=CHR⁶ [e.g. phenyl or 2-difluoromethoxyphenyl], —CR⁵(CR⁶₃)₂ or $(C_{3-12})$cycloalkyl [e.g. —CH(CH₃)₂ or cyclopropyl]; R⁴ is —C(O)X⁵R¹¹ [e.g.

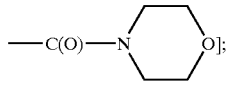

R²⁰ is hydrogen; R²³ is $(C_{1-6})$alkyl [e.g. ethyl orbutyl]; R²⁴ is hydrogen; and R²⁵ is tert-butyl, cyclopropyl, ethyl, phenyl, pyridin-3-yl, pyridin-4-yl, thien-3-yl or trifluoromethyl, and their corresponding N-oxides, and their prodrugs, and their protected derivatives, individual isomers and mixtures of isomers thereof; and the pharmaceutically acceptable salts and solvates (e.g. hydrates) of such compounds of Formula (Ic) and their N-oxides and their prodrugs, and their protected derivatives, individual isomers and mixtures of isomers thereof.

Particular compounds of the invention may prepared by joining carbon atom (C*) of one of the fragments (A1 to A36 or A40 to A71) or the sulfur atom (S*) of one of the fragments (A37 to A39 or A72) shown in Table 1 to the nitrogen atom (*N) of one of the fragments (B1 to B84) shown in Table 2, and joining the methine carbon atom (CH*) of one of the fragments (B1 to B84) shown in Table 2 to the acyl carbon atom (C*) of one of the fragments (C1 to C40) depicted in Table 3.

TABLE 1

| A1 | ![benzoyl] |
| A2 | ![morpholine carbonyl] |
| A3 | ![acetyl] |
| A4 | ![furan-3-carbonyl] |
| A5 | ![3-methoxybenzoyl] |
| A6 | ![2-methoxybenzoyl] |

TABLE 1-continued
| | | |
|---|---|---|
| A7 | 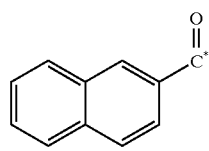 | |
| A8 | 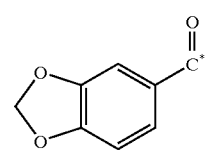 | |
| A9 | 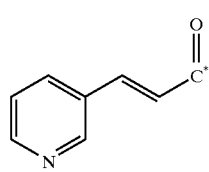 | |
| A10 | 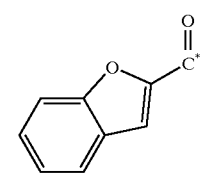 | |
| A11 | 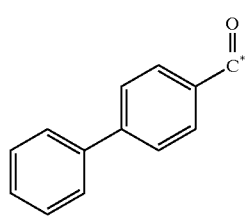 | |
| A12 | 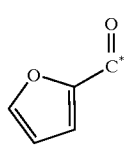 | |
| A13 | 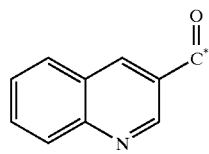 | |
| A14 | 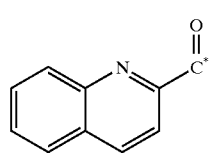 | |
| A15 | 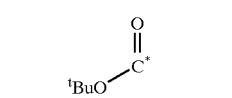 | |
| A16 | 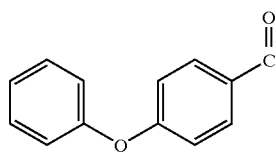 | |
TABLE 1-continued
| | | |
|---|---|---|
| A17 | 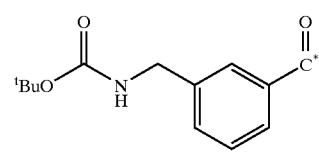 | |
| A18 | 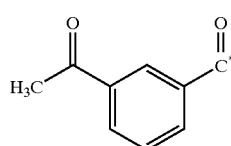 | |
| A19 | 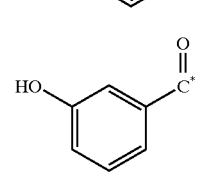 | |
| A20 | 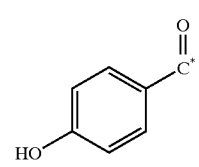 | |
| A21 | 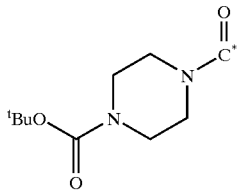 | |
| A22 | 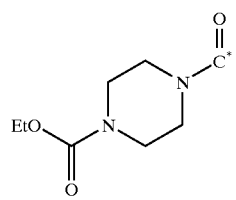 | |
| A23 | 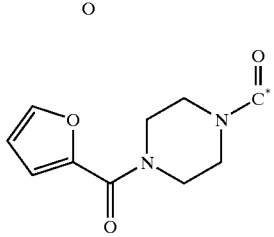 | |
| A24 | 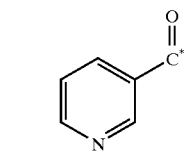 | |
| A25 | 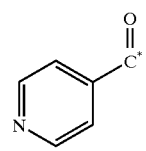 | |

TABLE 1-continued
| | |
|---|---|
| A26 | 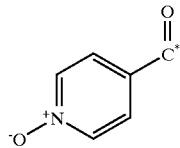 |
| A27 | 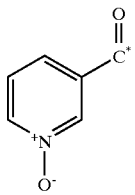 |
| A28 | 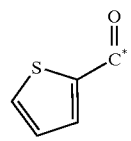 |
| A29 | 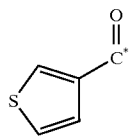 |
| A30 | 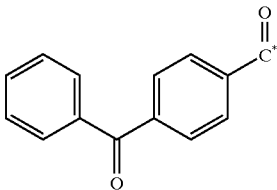 |
| A31 | 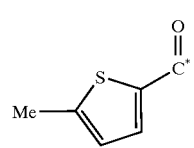 |
| A32 | 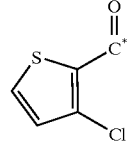 |
| A33 |  |
| A34 | 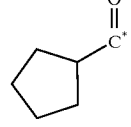 |
TABLE 1-continued
| | |
|---|---|
| A35 | 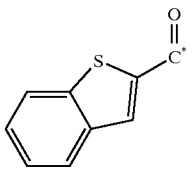 |
| A36 | 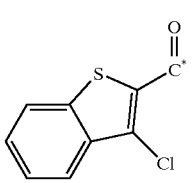 |
| A37 | 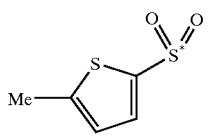 |
| A38 | 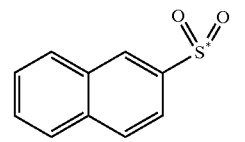 |
| A39 | 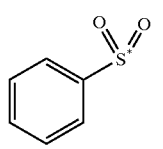 |
| A40 | 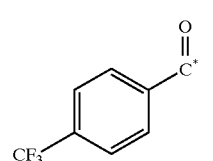 |
| A41 | 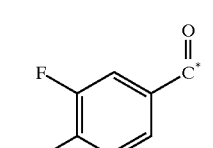 |
| A42 | 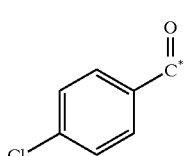 |
| A43 | 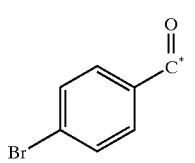 |

TABLE 1-continued
| | |
|---|---|
| A44 | 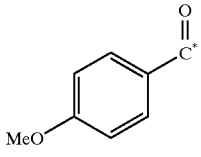 |
| A45 | 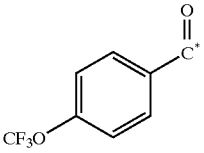 |
| A46 | 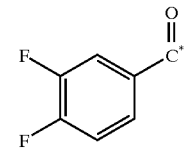 |
| A47 | 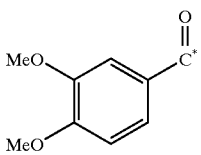 |
| A48 | 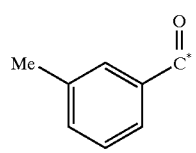 |
| A49 | 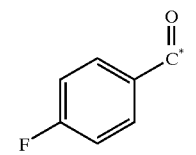 |
| A50 | 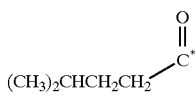 |
| A51 | 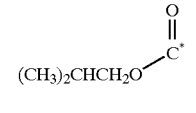 |
| A52 | 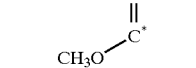 |
| A53 | 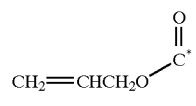 |
| A54 | 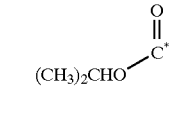 |
| A55 | 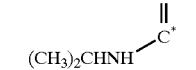 |
TABLE 1-continued
| | |
|---|---|
| A56 | 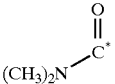 |
| A57 | 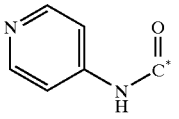 |
| A58 | 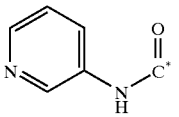 |
| A59 | 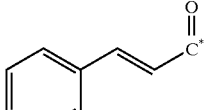 |
| A60 | 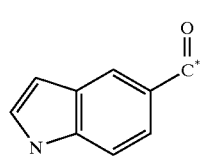 |
| A61 | 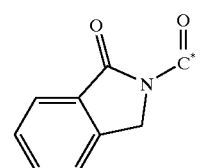 |
| A62 | 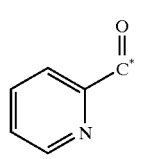 |
| A63 | 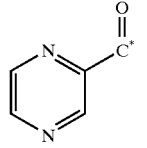 |
| A64 | 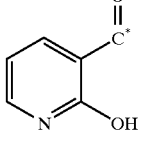 |
| A65 | 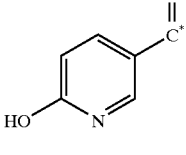 |

TABLE 1-continued
A66 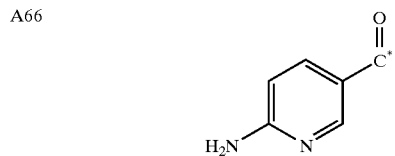
A67 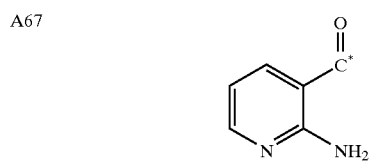
A68 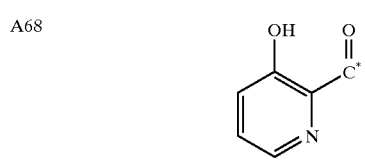
A69 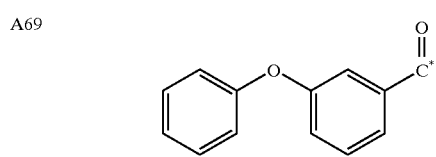
A70 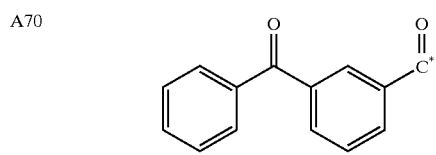
A71 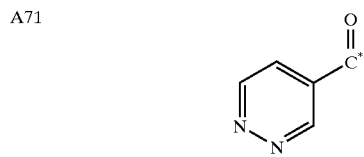
A72 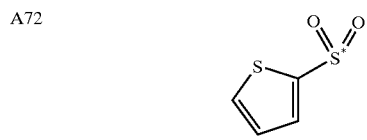
TABLE 2
B1 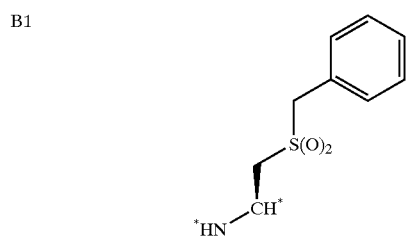
TABLE 2-continued
B2 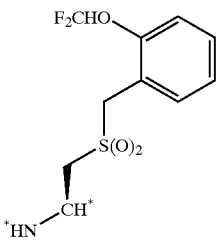
B3 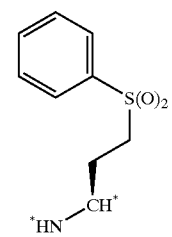
B4 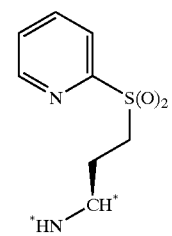
B5 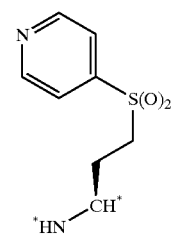
B6 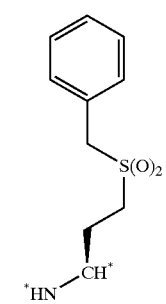
B7 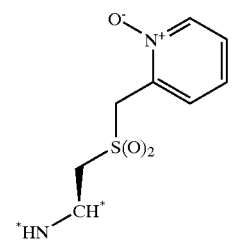

TABLE 2-continued
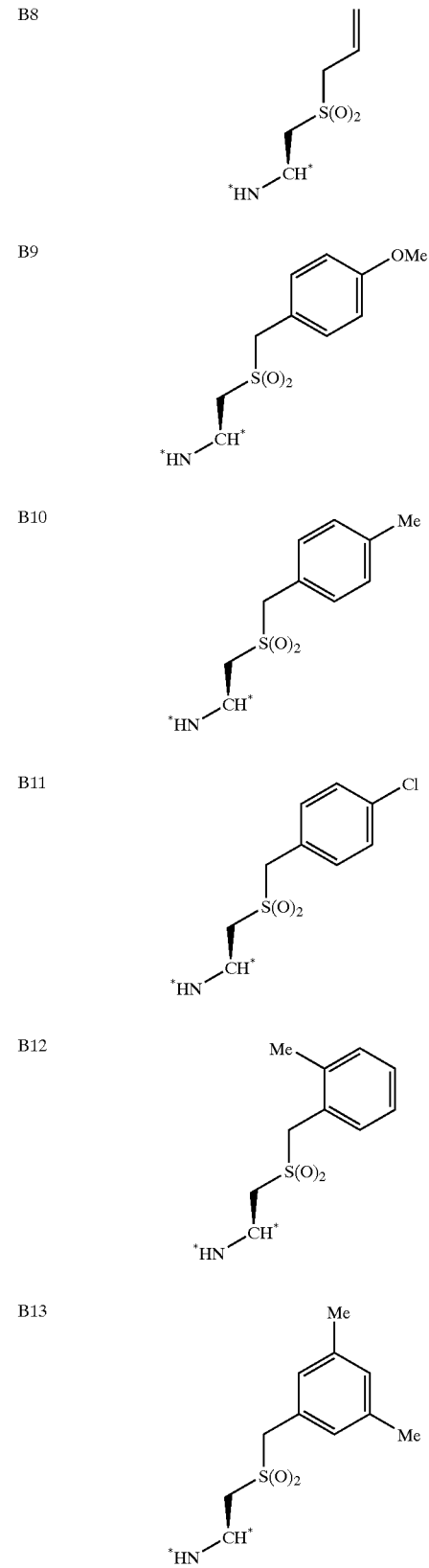
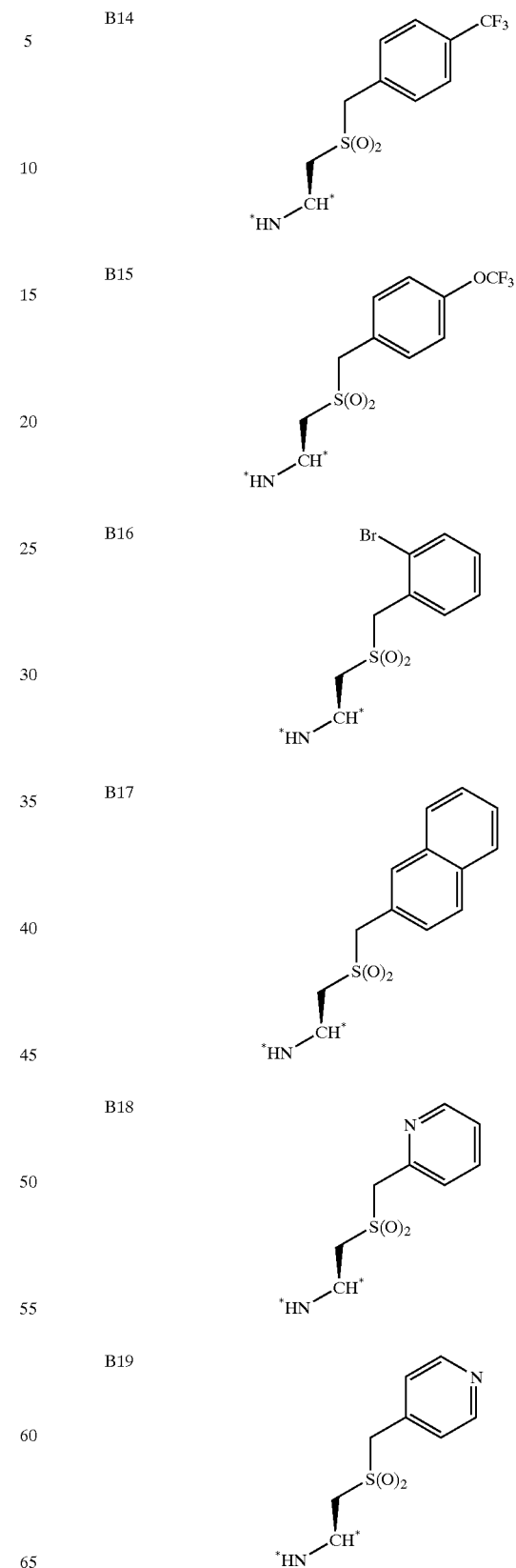

TABLE 2-continued
| B20 | 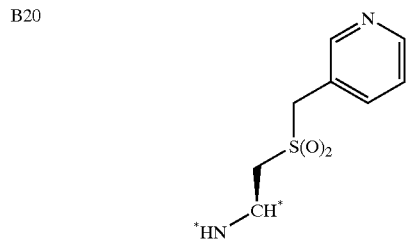 |
| B21 | 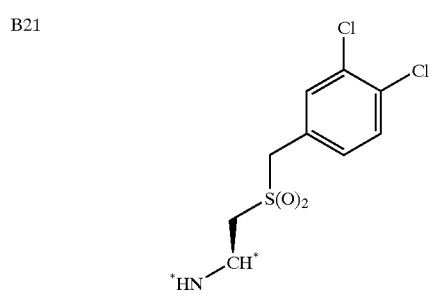 |
| B22 | 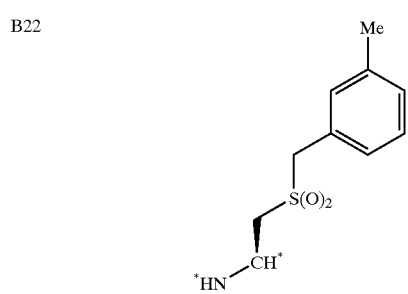 |
| B23 | 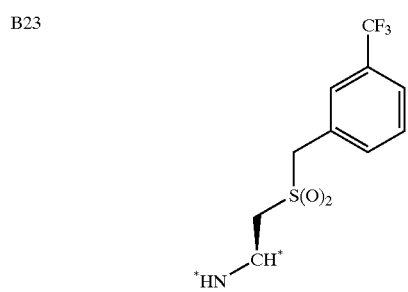 |
| B24 | 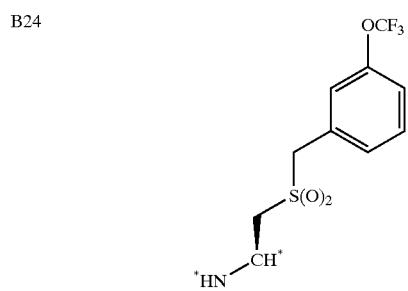 |
| B25 | 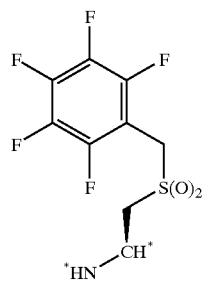 |
| B26 | 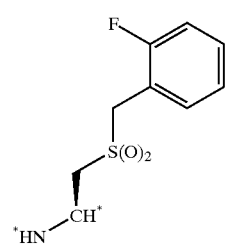 |
| B27 | 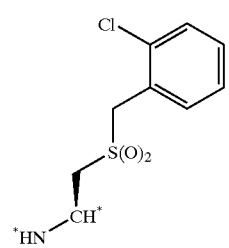 |
| B28 | 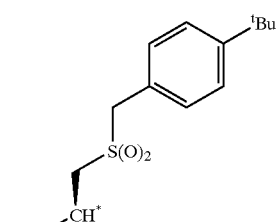 |
| B29 | 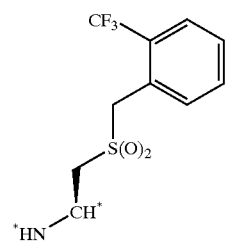 |
| B30 | 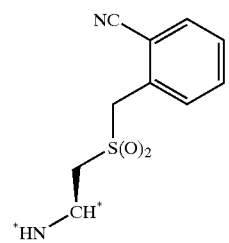 |

TABLE 2-continued
| | |
|---|---|
| B31 | 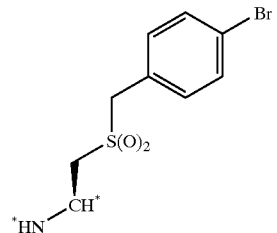 |
| B32 | 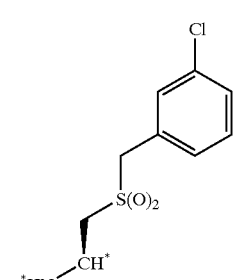 |
| B33 | 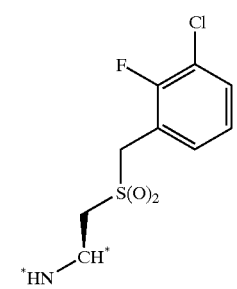 |
| B34 | 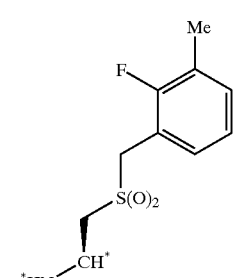 |
| B35 | 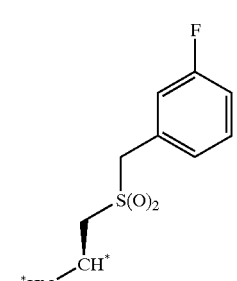 |
TABLE 2-continued
| | |
|---|---|
| B36 | 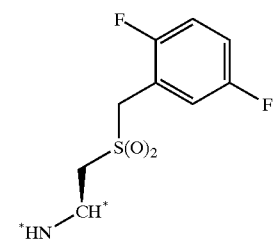 |
| B37 | 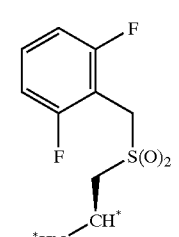 |
| B38 | 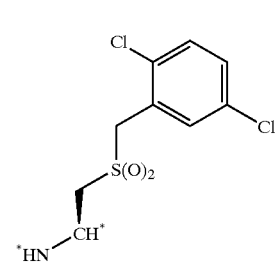 |
| B39 | 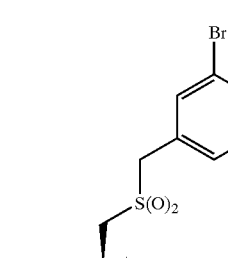 |
| B40 | 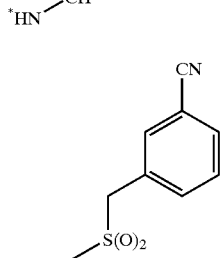 |
| B41 | 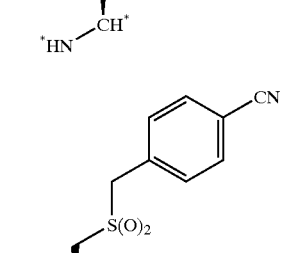 |

TABLE 2-continued

| | | |
|---|---|---|
| B42 | 2-(trifluoromethoxy)benzyl-CH2-S(O)2-CH(*)-NH(*) | |
| B43 | 2,3-difluorobenzyl-CH2-S(O)2-CH(*)-NH(*) | |
| B44 | 2-phenylbenzyl-CH2-S(O)2-CH(*)-NH(*) | |
| B45 | 2-bromo-5-fluorobenzyl-CH2-S(O)2-CH(*)-NH(*) | |
| B46 | 4-fluorobenzyl-CH2-S(O)2-CH(*)-NH(*) | |
| B47 | 3,4-difluorobenzyl-CH2-S(O)2-CH(*)-NH(*) | |
| B48 | 2,4-difluorobenzyl-CH2-S(O)2-CH(*)-NH(*) | |
| B49 | 2,4,6-trifluorobenzyl-CH2-S(O)2-CH(*)-NH(*) | |
| B50 | 2,4,5-trifluorobenzyl-CH2-S(O)2-CH(*)-NH(*) | |
| B51 | 2,3,4-trifluorobenzyl-CH2-S(O)2-CH(*)-NH(*) | |
| B52 | 2-chloro-5-(trifluoromethyl)benzyl-CH2-S(O)2-CH(*)-NH(*) | |
| B53 | 2,4-bis(trifluoromethyl)benzyl-CH2-S(O)2-CH(*)-NH(*) | |

TABLE 2-continued
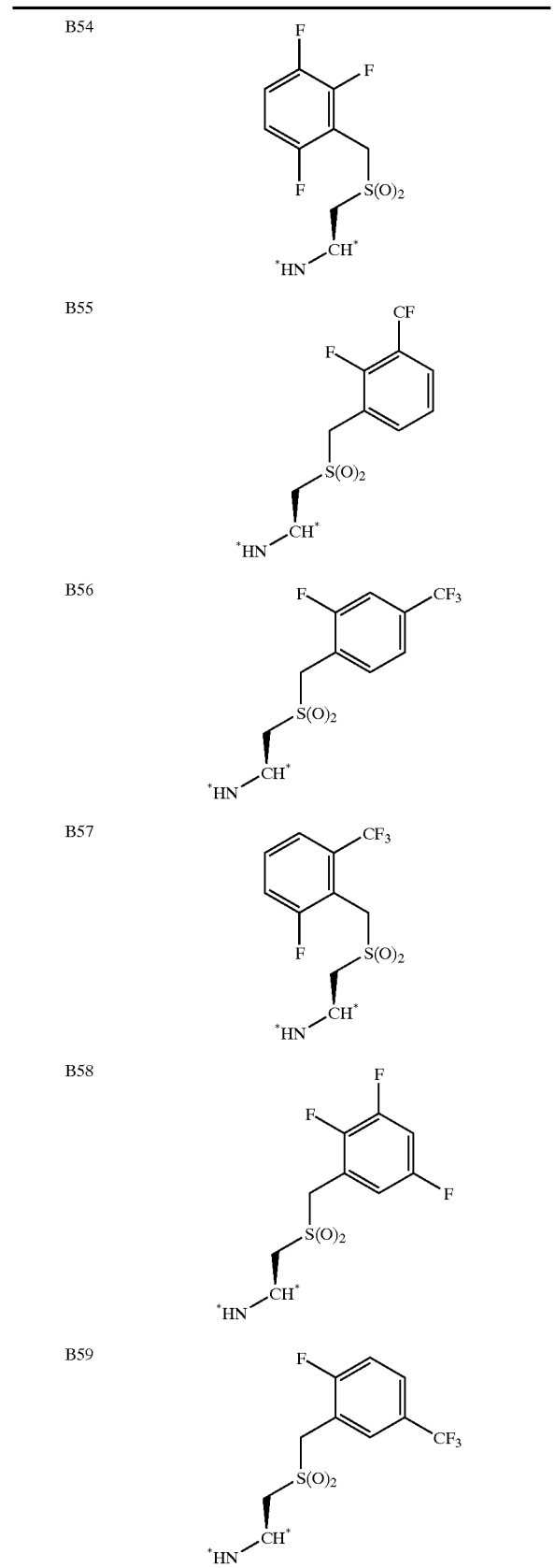
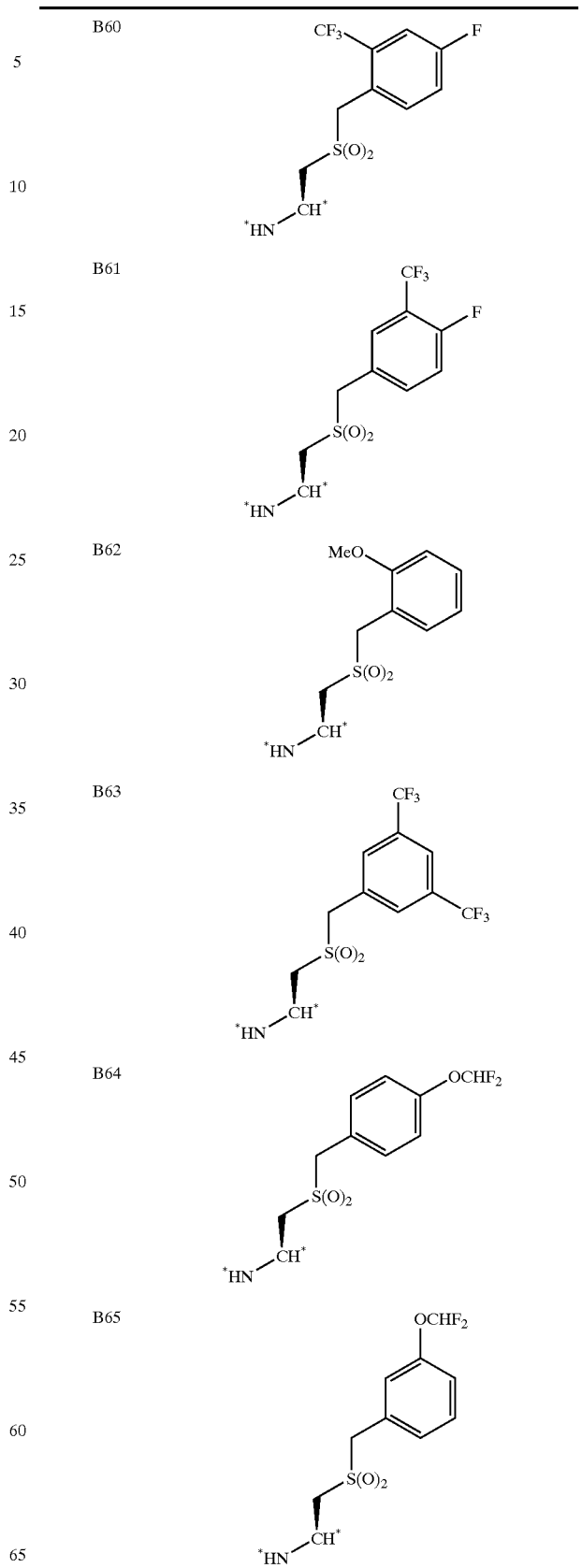

TABLE 2-continued

| | |
|---|---|
| B66 | 2,6-dichlorobenzyl-CH2-S(O)2-CH2-CH*(NH*) |
| B67 | 4-(CO2H)benzyl-CH2-S(O)2-CH2-CH*(NH*) |
| B68 | (3-Me,5-Me-isoxazol-4-yl)-CH2-S(O)2-CH2-CH*(NH*) |
| B69 | (5-Cl-thien-2-yl)-CH2-S(O)2-CH2-CH*(NH*) |
| B70 | 4-(OCHF2)phenyl-S(O)2-CH2-CH2-CH*(NH*) |
| B71 | 2-(OCHF2)phenyl-S(O)2-CH2-CH2-CH*(NH*) |
| B72 | 3-(OCHF2)phenyl-S(O)2-CH2-CH2-CH*(NH*) |
| B73 | 4-(OCF3)phenyl-S(O)2-CH2-CH2-CH*(NH*) |
| B74 | 2-(OCF2H)phenyl-S(O)2-CH2-CH2-CH*(NH*) |
| B75 | 3-(OCF2H)phenyl-S(O)2-CH2-CH2-CH*(NH*) |
| B76 | thien-2-yl-S(O)2-CH2-CH2-CH*(NH*) |
| B77 | phenyl-S(O)2-CH2-CH2-CH*(NH*) |

TABLE 2-continued
| | |
|---|---|
| B78 | 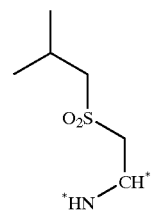 |
| B79 | 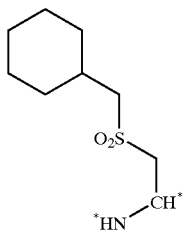 |
| B80 | 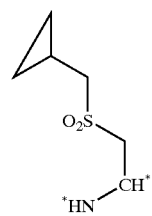 |
| B81 | 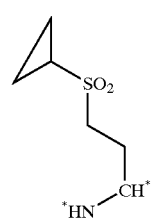 |
| B82 | 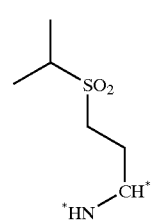 |
| B83 | 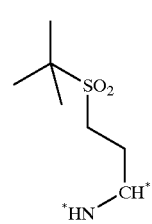 |
| B84 | 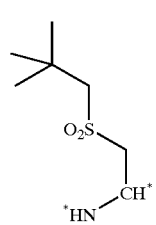 |
TABLE 3
| | |
|---|---|
| C1 | 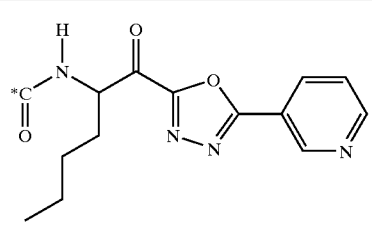 |
| C2 | 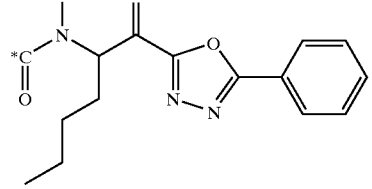 |
| C3 | 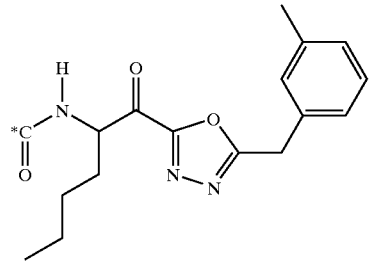 |
| C4 | 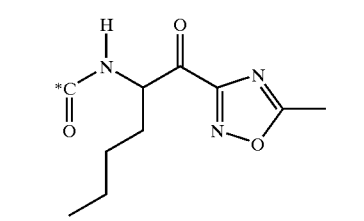 |
| C5 | 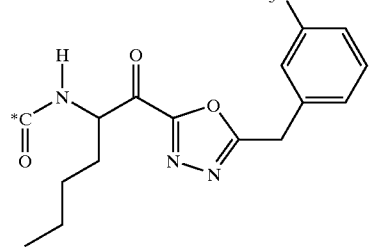 |
| C6 | 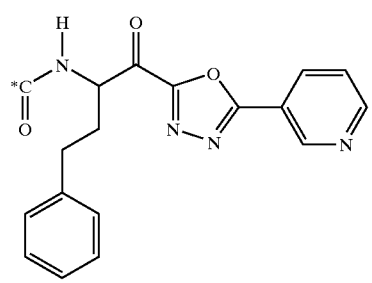 |

TABLE 3-continued
| | |
|---|---|
| C7 | 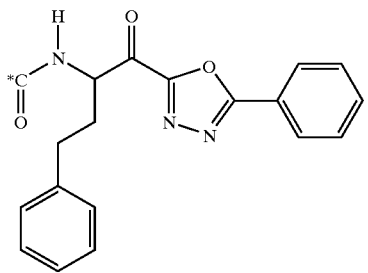 |
| C8 | 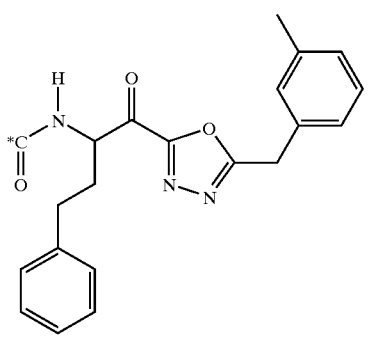 |
| C9 | 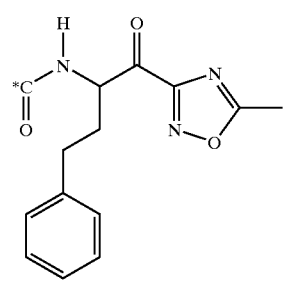 |
| C10 | 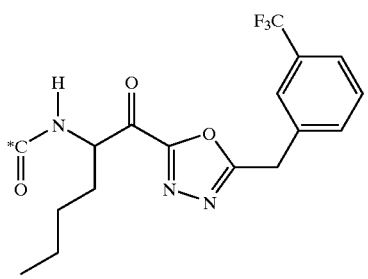 |
| C11 | 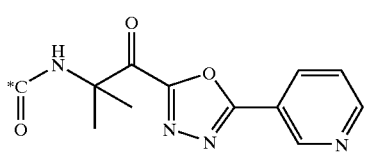 |
| C12 | 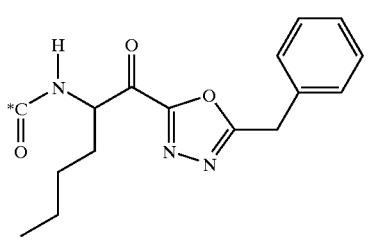 |
| C13 | 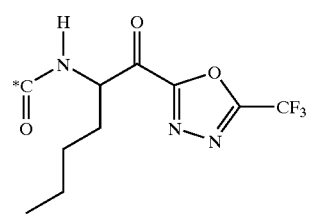 |
| C14 | 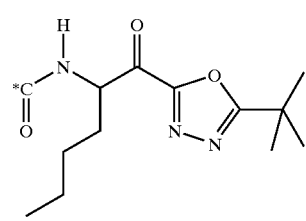 |
| C15 | 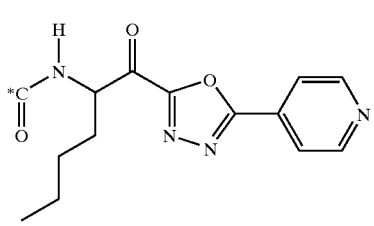 |
| C16 | 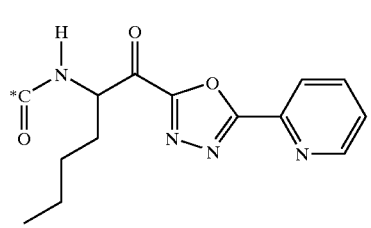 |
| C17 | 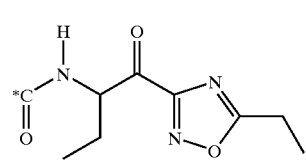 |
| C18 | 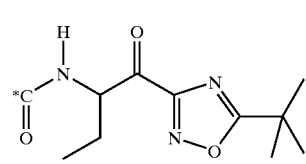 |
| C19 | 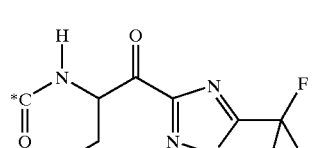 |
| C20 | 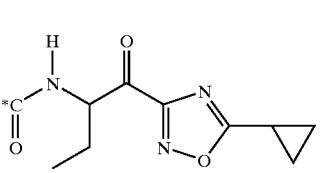 |

TABLE 3-continued

| | |
|---|---|
| C21 | (structure: oxadiazole with 4-pyridyl) |
| C22 | (structure: oxadiazole with 3-pyridyl) |
| C23 | (structure: oxadiazole with 2-pyridyl) |
| C24 | (structure: oxadiazole with phenyl) |
| C25 | (structure: oxadiazole with 3-thienyl) |
| C26 | (structure: oxadiazole with 2-thienyl) |
| C27 | (structure: oxadiazole with morpholinyl) |
| C28 | (structure: oxadiazole with tetrahydropyranyl) |
| C29 | (structure: oxadiazole with pyrazinyl) |
| C30 | (structure: 1,2,4-oxadiazole with pyrazinyl) |
| C31 | (structure: 1,2,4-oxadiazole with CF3) |
| C32 | (structure: 1,2,4-oxadiazole with cyclopropyl) |
| C33 | (structure: 1,2,4-oxadiazole with 4-pyridyl) |
| C34 | (structure: 1,2,4-oxadiazole with 3-pyridyl) |
| C35 | (structure: 1,2,4-oxadiazole with 2-pyridyl) |

TABLE 3-continued

| | |
|---|---|
| C36 | 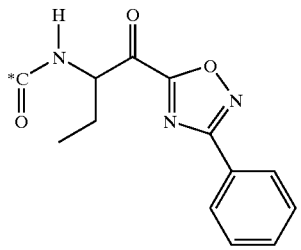 |
| C37 | 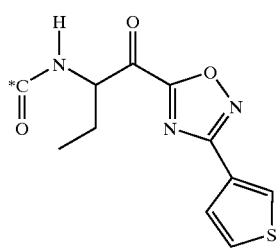 |
| C38 | 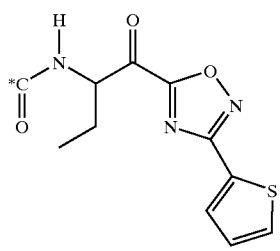 |
| C39 | 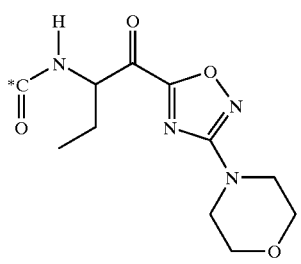 |
| C40 | 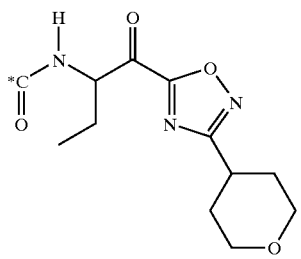 |

Thus, for example, the combination A2-B1-C2, that is, the combination of group A2 in Table 1 and B1 in Table 2 and C2 in Table 3, represents a compound of the invention, namely morpholine-4-carboxylic acid {2-phenylmethanesulfonyl-1-[1-(5-phenyl-[1,3,4]oxadiazol-2-carbonyl)-pentylcarbamoyl]-ethyl}-amide:

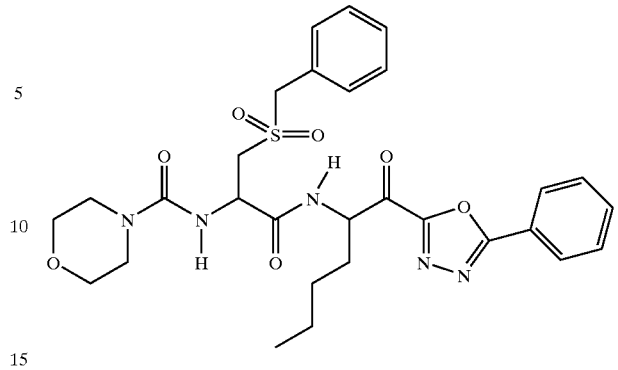

Further particular compounds of the present invention include:

morpholine-4-carboxylic acid {2-(2-difluoromethoxyphenylmethanesulfonyl)-1-[1,1-dimethyl-2-oxo-2-(5-pyridin-3-yl-[1,3,4]oxadiazol-2-yl)-ethylcarbamoyl]-ethyl}-amide;

morpholine-4-carboxylic acid {2-phenylmethanesulfonyl-1-[1-(5-phenyl-[1,3,4]oxadiazole-2-carbonyl)-pentylcarbamoyl]-ethyl}-amide (Compound 1; A2, B1, C2);

morpholine-4-carboxylic acid {2-(2-difluoromethoxyphenylmethanesulfonyl)-1-[1-(5-pyridin-3-yl-[1,3,4]oxadiazole-2-carbonyl)-pentylcarbamoyl]-ethyl}-amide (Compound 2; A2, B2, C1);

morpholine-4-carboxylic acid [1-[1-(3-cyclopropyl-1,2,4-oxadiazole-5-carbonyl)-propylcarbamoyl]-2-(2-methyl-propane-1-sulfonyl)-ethyl]-amide;

morpholine-4-carboxylic acid {2-(2-methyl-propane-1-sulfonyl)-1-[1-(3-thiophen-2-yl-1,2,4-oxadiazole-5-carbonyl)-propylcarbamoyl]-ethyl}-amide;

morpholine-4-carboxylic acid [1-[1-(3-tert-butyl-1,2,4-oxadiazole-5-carbonyl)-propylcarbamoyl]-2-(2-methyl-propane-1-sulfonyl)-ethyl]-amide;

morpholine-4-carboxylic acid {2-cyclopropylmethanesulfonyl-1-[1-(5-phenyl-1,2,4-oxadiazole-3-carbonyl)-propylcarbamoyl]-ethyl}-amide;

morpholine-4-carboxylic acid {(R)-2-cyclopropylmethanesulfonyl-1-[(S)-1-(5-trifluoromethyl-1,2,4-oxadiazole-3-carbonyl)-propylcarbamoyl]-ethyl}-amide;

morpholine-4-carboxylic acid [(1-[(1-(5-ethyl-1,2,4-oxadiazole-3-carbonyl)-propylcarbamoyl]-2-(2-methyl-propane-1-sulfonyl)-ethyl]-amide;

{(R)-2-(2-methyl-propane-1-sulfonyl)-1-[(S)-1-(5-thiophen-3-yl-1,2,4-oxadiazole-3-carbonyl)-propylcarbamoyl]-ethyl}-amide;

morpholine-4-carboxylic acid {(R)-1-[(S)-1-(3-tert-butyl-1,2,4-oxadiazole-5-carbonyl)-propylcarbamoyl]-2-cyclopropylmethanesulfonyl-ethyl}-amide;

morpholine-4-carboxylic acid {(R)-2-(2-methyl-propane-1-sulfonyl)-1-[(S)-1-(5-trifluoromethyl-1,2,4-oxadiazole-3-carbonyl)-propylcarbamoyl]-ethyl}-amide;

morpholine-4-carboxylic acid {(R)-1-[(S)-1-(5-tert-butyl-1,2,4-oxadiazole-3-carbonyl)-propylcarbamoyl]-2-phenylmethanesulfonyl-ethyl}-amide;

morpholine-4-carboxylic acid {(R)-1-[(S)-1-(5-tert-butyl-1,2,4-oxadiazole-3-carbonyl)-propylcarbamoyl]-2-phenylmethanesulfonyl-ethyl}-amide;

morpholine-4-carboxylic acid {2-cyclopropylmethanesulfonyl-1-[1-(3-cyclopropyl-1,2,4-oxadiazole-5-carbonyl)-propylcarbamoyl]-ethyl}-amide;

morpholine-4-carboxylic acid {2-cyclopropylmethanesulfonyl-1-[1-(3-ethyl-1,2,4-oxadiazole-5-carbonyl)-propylcarbamoyl]-ethyl}-amide;
morpholine-4-carboxylic acid {2-cyclopropylmethanesulfonyl-1-[1-(3-phenyl-1,2,4-oxadiazole-5-carbonyl)-propylcarbamoyl]-ethyl}-amide;
morpholine-4-carboxylic acid {2-(2-methyl-propane-1-sulfonyl)-1-[1-(3-phenyl-1,2,4-oxadiazole-5-carbonyl)-propylcarbamoyl]-ethyl}-amide;
morpholine-4-carboxylic acid [1-[1-(3-ethyl-1,2,4-oxadiazole-5-carbonyl)-propylcarbamoyl]-2-(2-methyl-propane-1-sulfonyl)-ethyl]-amide;
morpholine-4-carboxylic acid {2-phenylmethanesulfonyl-1-[1-(3-phenyl-[1,2,4]oxadiazole-5-carbonyl)-propylcarbamoyl]-ethyl}-amide;
morpholine-4-carboxylic acid {1-[1-(3-ethyl-[1,2,4]oxadiazole-5-carbonyl)-propylcarbamoyl]-2-phenylmethanesulfonyl-ethyl}-amide;
morpholine-4-carboxylic acid {1-[1-(5-ethyl-[1,3,4]oxadiazole-2-carbonyl)-propylcarbamoyl]-2-phenylmethanesulfonyl-ethyl}-amide;
morpholine-4-carboxylic acid {1-[1-(5-tert-butyl-[1,3,4]oxadiazole-2-carbonyl)-propylcarbamoyl]-2-phenylmethanesulfonyl-ethyl}-amide;
morpholine-4-carboxylic acid {2-(2-difluoromethoxy-phenylmethanesulfonyl)-1-[1,1-dimethyl-2-oxo-2-(5-pyridin-3-yl-[1,3,4]oxadiazol-2-yl)-ethylcarbamoyl]-ethyl}-amide;
and their corresponding N-oxides, and their prodrugs, and their protected derivatives, individual isomers and mixtures of isomers thereof; and the pharmaceutically acceptable salts and solvates (e.g. hydrates), and their N-oxides and their prodrugs, and their protected derivatives, individual isomers and mixtures of isomers thereof.

Pharmacology and Utility:

The compounds of the invention are selective inhibitors of cathepsin S and, as such, are useful for treating diseases in which cathepsin S activity contributes to the pathology and/or symptomatology of the disease. For example, the compounds of the invention are useful in treating autoimmune disorders, including, but not limited to, juvenile onset diabetes, multiple sclerosis, pemphigus vulgaris, Graves' disease, myasthenia gravis, systemic lupus erythemotasus, rheumatoid arthritis and Hashimoto's thyroiditis, allergic disorders, including, but not limited to, asthma, and allogeneic immune responses, including, but not limited to, organ transplants or tissue grafts.

Cathepsin S also is implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of cathepsin S are of use in treatment of systemic amyloidosis.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease-induced hydrolysis of a peptide-based substrate. Details of assays for measuring protease inhibitory activity are set forth in Examples 25–28, infra.

Administration and Pharmaceutical Compositions:

In general, compounds of Formula (I) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (I) may range from about 1 micrograms per kilogram body weight ($\mu$g/kg) per day to about 60 milligram per kilogram body weight (mg/kg) per day, typically from about 1 $\mu$g/kg/day to about 20 mg/kg/day. Therefore, a therapeutically effective amount for an 80 kg human patient may range from about 80 $\mu$g/day to about 4.8 g/day, typically from about 80 $\mu$g/day to about 1.6 g/day. In general, one of ordinary skill in the art, acting in reliance upon personal knowledge and the disclosure of this Application, will be able to ascertain a therapeutically effective amount of a compound of Formula (I) for treating a given disease.

The compounds of Formula (I) can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula (I) in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula (I) in the composition may vary widely depending upon the type of formulation, size of a unit dosage, kind of excipients and other factors known to those of skill in the art of pharmaceutical sciences. In general, a composition of a compound of Formula (I) for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula (I) are described in Example 29, infra.

Chemistry:

Processes for Making Compounds of Formula (I):

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Compounds of Formula (I), in which $X^3$ is a group of formula (a) (as defined in the Summary of the Invention), i.e. compounds of Formula (V), can be prepared by proceeding as in the following Reaction Scheme 1:

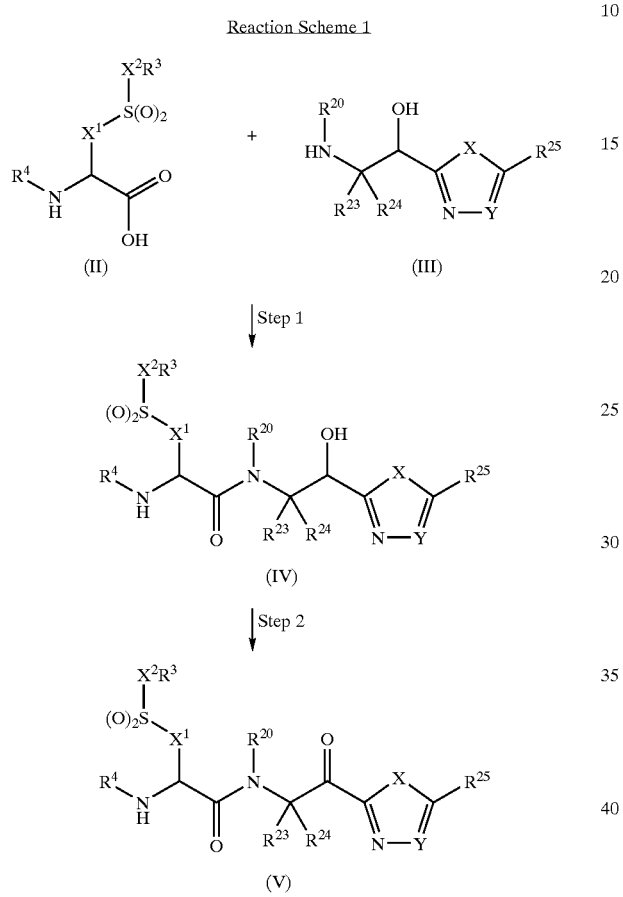

in which each X, $X^1$, $X^2$, Y, $R^3$, $R^4$, $R^{20}$, $R^{23}$, $R^{24}$ and $R^{25}$ are as defined for Formula (I) in the Summary of the Invention. Thus, in step 1, an acid of formula (II) may be condensed with an amino compound of formula (E) to give a β-hydroxy amide of formula (IV). The condensation reaction can be effected with an appropriate coupling agent (e.g., benzotriazol-1-yloxytrispyrrolidinophosphonium hexafluorophosphate (PyBOP®), 1-(3-dimethylaminopropyl)-3-ethylcarbodiimide hydrochloride (EDCI), O-benzotriazol-1-yl-N,N,N',N'-tetramethyluronium hexafluorophosphate (HBTU), 1,3-dicyclohexylcarbodiimide (DCC), or the like) and optionally an appropriate catalyst (e.g., 1-hydroxybenzotriazole (HOBt), 1-hydroxy-7-azabenzotriazole (HOAt), O-(7-azabenzotrizol-1-yl)-1,1,3,3, tetra-methyluroniumhexafluorophosphate (HATU), or the like) and non-nucleophilic base (e.g., triethylamine, N-methylmorpholine, and the like, or any suitable combination thereof) at ambient temperature and requires 5 to 10 hours to complete. The β-hydroxy amide of formula (IV) may then be oxidized, in step 2, to give a compound of formula (V). The oxidation reaction may conveniently be carried out using Dess-Martin periodinane in an inert solvent, such as dichloromethane, and at a temperature from about 0° C. to about room temperature.

Compounds of Formula (I), where $X^3$ is a group of formula (b) (as defined in the Summary of the Invention), can be prepared by proceeding as in Reaction Scheme 2 but using an amino compound of formula (VI). Compounds of Formula (I), where $X^3$ is a compound of formula (c) (as defined in the Summary of the Invention), can be prepared by proceeding as in Reaction Scheme 2 but using an amino compound of formula (VII),

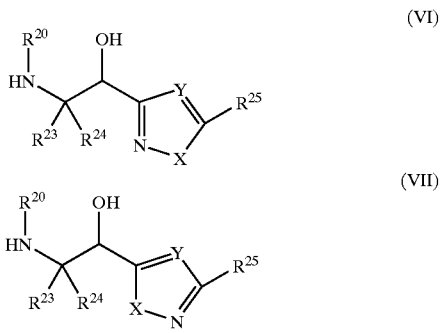

in which each X, Y, $R^{20}$, $R^{23}$, $R^{24}$ and $R^{25}$ are as defined for formula (I) in the Summary of the Invention.

Detailed descriptions for the synthesis of a compound of Formula (I) by the processes in Reaction Scheme 1 are set forth in the Examples 1 to 20, infra.

Additional Processes for Preparing Compounds of Formula (I):

A compound of Formula (I) can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula (I) can be prepared by reacting the free acid form of the compound with a pharmaceutically acceptable inorganic or organic base. Inorganic and organic acids and bases suitable for the preparation of the pharmaceutically acceptable salts of compounds of Formula (I) are set forth in the definitions section of this Application. Alternatively, the salt forms of the compounds of Formula (I) can be prepared using salts of the starting materials or intermediates.

The free acid or free base forms of the compounds of Formula (I) can be prepared from the corresponding base addition salt or acid addition salt form. For example, a compound of Formula (I) in an acid addition salt form can be converted to the corresponding free base by treating with a suitable base (e.g., ammonium hydroxide solution, sodium hydroxide, and the like). A compound of Formula (I) in a base addition salt form can be converted to the corresponding free acid by treating with a suitable acid (e.g., hydrochloric acid, etc).

The N-oxides of compounds of Formula (I) can be prepared by methods known to those of ordinary skill in the art. For example, N-oxides can be prepared by treating an unoxidized form of the compound of Formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula (I) can be prepared from the N-oxide of an appropriate starting material.

Compounds of Formula (I) in unoxidized form can be prepared from N-oxides of compounds of Formula (I) by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds of Formula (I) can be prepared by methods known to those of ordinary skill in the art (e.g., for further details see Saulnier et al.(1994), *Bioorganic and Medicinal Chemistry Letters*, Vol. 4, p. 1985). For example, appropriate prodrugs can be prepared by reacting a non-derivatized compound of Formula (I) with a suitable carbamylating agent (e.g., 1,1-acyloxyalkylcarbonochloridate, para-nitrophenyl carbonate, or the like).

Protected derivatives of the compounds of Formula (I) can be made by means known to those of ordinary skill in the art. A detailed description of the techniques applicable to the creation of protecting groups and their removal can be found in T. W. Greene, *Protecting Groups in Organic Synthesis*, 3$^{rd}$ edition, John Wiley & Sons, Inc. 1999.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxin, tetrahydrofuran or methanol. Compounds of Formula (I) can be prepared as their individual stereoisomers by reacting a racemic mixture of the compound with an optically active resolving agent to form a pair of diastercoisomeric compounds, separating the diastereomers and recovering the optically pure enantiomer. While resolution of enantiomers can be carried out using covalent diasteromeric derivatives of compounds of Formula (I), dissociable complexes are preferred (e.g., crystalline diastercoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

In summary, the compounds of Formula (I) are made by a process which comprises:

(A) reacting a compound of Formula (II):

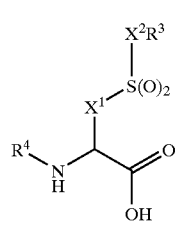

(II)

with a compound of the Formula (III):

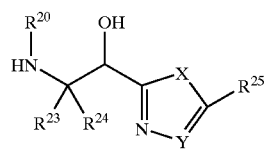

(III)

followed by oxidation of the resulting β-hydroxy amide (IV):

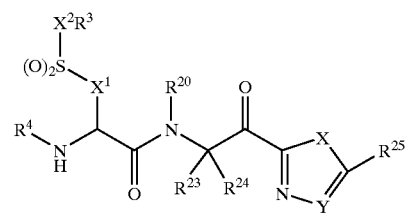

(IV)

in which X, Y, X$^1$, X$^2$, R$^3$, R$^4$, R$^{20}$, R$^{23}$, R$^{24}$ and R$^{25}$ are as defined in the Summary of the Invention for Formula (I); or (B) reacting a compound of Formula (II) with a compound of the formula (VI):

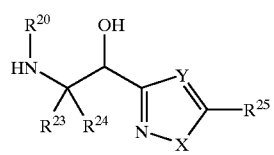

(VI)

followed by oxidation of the resulting β-hydroxy amide (VIII):

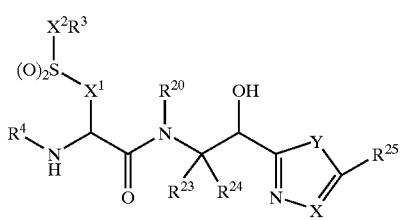

(VIII)

in which X, Y, R$^{20}$, R$^{23}$, R$^{24}$ and R$^{25}$ are as defined in the Summary of the Invention for Formula (I); or (C) reacting a compound of Formula (II) with a compound of the formula (VII):

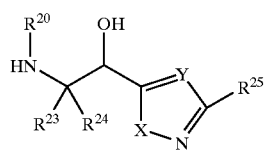

(VII)

followed by oxidation of the resulting β-hydroxy amide (IX):

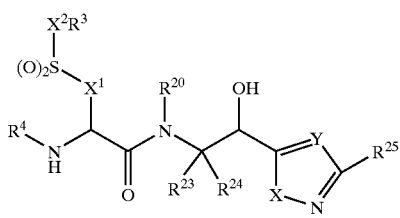

(IX)

in which X, Y, $R^{20}$, $R^{23}$, $R^{24}$ and $R^{25}$ are as defined in the Summary of the Invention for Formula (I); and (D) optionally converting a compound of Formula (I) into a pharmaceutically acceptable salt;
(E) optionally converting a salt form of a compound of Formula (I) to non-salt form;
(F) optionally converting an unoxidized form of a compound of Formula (I) into a pharmaceutically acceptable N-oxide;
(G) optionally converting an N-oxide form of a compound of Formula (I) its unoxidized form;
(H) optionally resolving an individual isomer of a compound of Formula (I) from a mixture of isomers;
(I) optionally converting a non-derivatized compound of Formula (I) into a pharmaceutical prodrug derivative; and
(J) optionally converting a prodrug derivative of a compound of Formula (I) to its non-derivatized form.

Intermediates of formula (II), wherein $X^1$ is methylene, $X^2$ is methylene and $R^3$ and $R^4$ are as hereinbefore defined, may be prepared by: (i) alkylation of cysteine with an alkyl bromide of formula $R^3CH_2Br$ [the reaction may conveniently be carried out in the presence of an alkali metal hydroxide, such sodium hydroxide, in ethanol and at a temperature up to about 40° C.]; (ii) reaction with a compound of formula $R^4$—Cl (e.g. morpholine carbonyl chloride) in the presence of a suitable base, such as triethylamine, in an inert solvent, such as acetonitrile, and at room temperature; (iii) oxidation, for example with $H_2WO_4$ and hydrogen peroxide, in a suitable solvent, such as isopropyl alcohol, and at a temperature at about 15–20° C.

Intermediates of formula (III), wherein X, Y, $R^{20}$, $R^{23}$, $R^{24}$ and $R^{25}$ are as hereinbefore defined, may be prepared by: (i) treatment of compounds of formula (X) [wherein X, Y and $R^{25}$ are as hereinbefore defined] with butyl lithium in an inert solvent, such as tetrahydrofuran, at a temperature at about −78° C.; (ii) treatment of the resulting anion with magnesium bromide dietherate at a temperature at about −78° C.; (iii) reaction of the resulting Grignard with an aldehyde of formula (XI) [wherein $R^{20}$, $R^{23}$ and $R^{24}$ are as hereinbefore defined at a temperature at about −45° C.

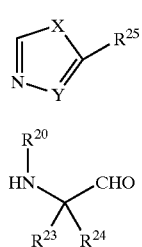

(X)

(XI)

The preparation of intermediates of formula (III) may be conveniently carried out with the NH of compounds of formula (XI) protected, with for example a Boc group.

Compounds of formula (X), wherein X, Y and $R^{25}$ are as hereinbefore defined, may be prepared by reaction of hydrazones of formula (XII)

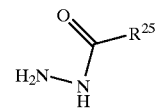

(XII)

wherein $R^{25}$ is as hereinbefore defined, with triethylorthoformate, in the presence of an acid catalyst, such as para-toluenesulfonic acid, and at a temperature up to about 125° C.

Intermediates of formula (VI), wherein X, Y, $R^{20}$, $R^{23}$, $R^{24}$ and $R^{25}$ are as hereinbefore defined, may be prepared as in the following reaction scheme 2:

Reaction Scheme 2

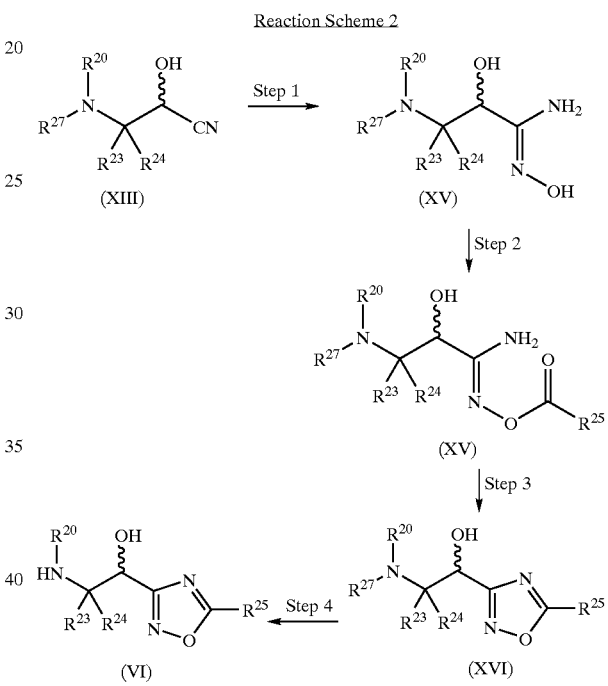

Thus, in step 1, α-hydroxy nitriles of formula (XIII) [wherein $R^{20}$, $R^{23}$, $R^{24}$ and $R^{25}$ are as hereinbefore defined and $R^{27}$ is a suitable protecting group, such as tert-butyloxycarbonyl, may be reacted with hydroxylamine in the presence of an alkali metal alkoxide, such as sodium methoxide, in methanol and at 0° C. The resulting compounds of formula (XIV) [wherein $R^{20}$, $R^{23}$, $R^{24}$, $R^{25}$ and $R^{27}$ are as hereinbefore defined] may then be coupled, in step 2, with acids of formula $R^{25}$—$CO_2H$ [wherein $R^{25}$ is as hereinbefore defined] in the presence of an appropriate coupling agent [e.g. 1-(3-dimethylaminopropyl)-3-ethylcarbodiimide hydrochloride (EDCI)] and optionally an appropriate catalyst [e.g. 1-hydroxybenzotriazole (HOBt)] and a non-nucleophilic base [e.g. triethylamine] at about room temperature. The resulting compounds of formula (XV) [wherein $R^{20}$, $R^{23}$, $R^{24}$, $R^{25}$ and $R^{27}$ are as hereinbefore defined] may then be cyclised, in step 3, by heating in an inert solvent, such as diglyme, at a temperature from about 150° C. to about 200° C. in a microwave reactor. The cyclised compounds of formula (XVI) [wherein $R^{20}$, $R^{23}$, $R^{24}$, $R^{25}$ and $R^{27}$ are as hereinbefore defined] may then be deprotected, in step 4, to give intermediates of formula (VI)

[for example when $R^{27}$ is tert-butyloxycarbonyl the deprotection is conveniently carried out by treatment with trifluoroacetic acid at room temperature].

Intermediates of formula (VII), wherein X, Y, $R^{20}$, $R^{23}$, $R^{24}$ and $R^{25}$ are as hereinbefore defined, may be prepared as in the following reaction scheme 3:

Reaction Scheme 3

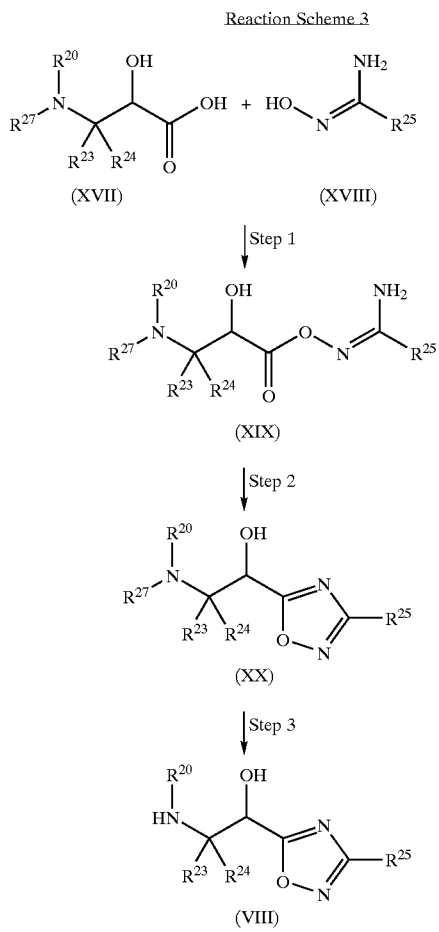

Thus, in step 1, α-hydroxy acids of formula (XVII) [wherein $R^{20}$, $R^{23}$, $R^{24}$ and $R^{27}$ are as hereinbefore defined] may be reacted with N-hydroxy-amidines of formula (XVIII) [wherein $R^{25}$ is as hereinbefore defined] in the presence of a suitable coupling agent, such as N-cyclohexylcarbodiimide-N'-methyl polystyrene, in an inert solvent, such as dichloromethane and at a temperature at about 0° C. The resulting compounds of formula (XIX) [wherein $R^{20}$, $R^{23}$, $R^{24}$, $R^{25}$ and $R^{27}$ are as hereinbefore defined] are then cyclised, in step 2, by heating in a microwave reactor in an inert solvent, such as tetrahydrofuran, at a temperature at about 180° C. The resulting oxadiazoles of formula (XX) [wherein $R^{20}$, $R^{23}$, $R^{24}$, $R^{25}$ and $R^{27}$ are as hereinbefore defined] may then be deprotected, in step 4, to give intermediates of formula (VI) [for example when $R^{27}$ is tert-butyloxycarbonyl the deprotection is conveniently carried out by treatment with Silicycle triamine-3 in an inert solvent, such as dichloromethane, and at room temperature].

EXAMPLES

The present invention is further exemplified, but not limited by, the following examples that illustrate the preparation of compounds of Formula (I) (Examples) and intermediates (References) according to the invention.

Reference 1

2-Amino-1-(5-phenyl-[1,3,4]oxadiazol-2-yl)-1-hexanol

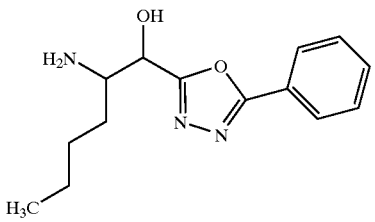

A mixture of the benzoylhydrazide (22.5 g, 165 mmol), triethylorthoformate (150 ml) and p-toluenesulfonic acid (300 mg) was heated at 120° C. for 12 hours. Excess triethylorthoformate was removed under vacuum and the residue was subjected to silica gel column chromatography to produce 2-phenyl-[1,3,4]oxadiazole (14.5 g); $H^1$ NMR [$(CD_3)_2SO$]: δ 9.34 (1H, s), 8.05–7.98 (2H, m), 7.68–7.55 (3H, m); MS: 147.4 (M+1)

To a stirred solution of 2-phenyl-[1,3,4]oxadiazole (1.46 g, 10 mmol) in THF (40 ml) was added n-BuLi (1.6M solution in 6.2 ml of hexane) drop-wise under $N_2$ at −78° C. After 1 hour, $MgBr.Et_2O$ (1.29 g, 5 mmol) was added and the reaction mixture was allowed to warm to −45° C. for 1 hour before being treated with 2-Boc-Nlu-aldehyde (1.07 g, 5 mmol) in THF (20 ml). The reaction mixture was stirred for 1 hour, quenched with saturated $NH_4Cl$, and extracted with ethyl acetate. The organic layer was washed with brine, dried with $MgSO_4$ and concentrated. The residue was subjected to silica gel column chromatography to yield 2-(2-Boc-amino-1-hydroxyhexyl)-5-phenyl-[1,3,4]oxadiazole (800 mg); MS: 360.2 (M−1), 362.6 (M+1), 364.6 (M=23).

2-(2-Boc-amino-1-hydroxyhexyl)-5-phenyl-[1,3,4] oxadiazole (130 mg, 0.36 mmol) and $MeCl_2$ (5 ml) were mixed and TFA (1 ml) was added at room temperature. After stirring for 1 hour, the solvent and excess TFA were removed under vacuum to produce 2-amino-1-(5-phenyl-[1,3,4] oxadiazol-2-yl)-1-hexanol.

Reference 2

2-Amino-1-(5-pyridin-3-yl-[1,3,4]oxadiazol-2-yl)-hexan-1-ol

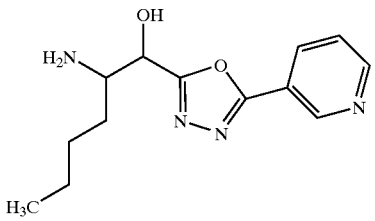

To a stirred solution of 2-(3-pyridyl)-[1,3,4]oxadiazole (500 mg, 3.4 mmol), in THF (20 ml) was added n-BuLi (1.6M solution in 2.1 ml of hexane) drop-wise under $N_2$ at −78° C. After 1 hour, $MgBr.Et_2O$ (808.6 g, 3.4 mmol) was added and the reaction mixture was allowed to warm to −45° C. for 1 hour before being treated with 2-Boc-Nlu-aldehyde (511 g, 2.38 mmol) in THF (10 ml). The reaction mixture was stirred for 1 hour, quenched with saturated $NH_4Cl$, and extracted with ethyl acetate. The organic layer was washed with brine, dried with MgSO$_4$ and concentrated. The residue was subjected to silica gel column chromatography to yield 2-(2-Boc-amino-1-hydroxyhexyl)-5-(3-pyridyl)-[1,3,4] oxadiazole (200 mg); MS: 361.4 (M−1), 363.2 (M+1).

2-(2-Boc-amino-1-hydroxyhexyl)-5-(3-pyridyl)-[1,3,4] oxadiazole (100 mg, 0.27 mmol) and MeCl$_2$ (5 ml) were mixed and TFA (1 ml) was added at room temperature. After stirring for 1 hour, the solvent and excess TFA were removed under vacuum to produce 2-amino-1-(5-pyridin-3-yl-[1,3,4] oxadiazol-2-yl)-hexan-1-ol.

Reference 3

2-Amino-1-(5-(4-pyridyl)-[1,3,4]oxadiazol-2-yl)-1-hexanol

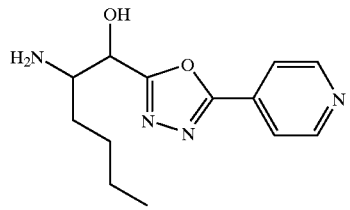

A mixture of the isonicotinic hydrazide (13.7 g, 100 mmol), triethylorthoformate (60 ml) and p-toluenesulfonic acid (30 mg) was heated at 130° C. for 12 hours. Excess triethylorthoformate was removed under vacuum. The residue was crystallized from ethyl acetate to give 2-(4-pyridyl)-[1,3,4]oxadiazole (14.8 g); H$^1$ NMR [(CD$_3$)$_2$SO]: δ 9.46 (1H, s), 8.8 (2H, dd), 7.9 (2H, dd).

To a stirred solution of 2-(4-pyridyl)-[1,3,4]oxadiazole (2.94 g, 20 mmol) in THF (80 ml) was added n-BuLi (1.6M solution in 12.5 ml of hexane) drop-wise under N$_2$ at −78° C. After 1 hour, MgBr.Et$_2$O (5.16 g, 20 mmol) was added and the reaction mixture was allowed to warm to −45° C. for 1 hour before being treated with 2-Boc-Nlu-aldehyde (2.58 g, 12 mmol) in THF (20 ml). The reaction mixture was stirred for 1 hour, quenched with saturated NH$_4$Cl, and extracted with ethyl acetate. The organic layer was washed with brine, dried with MgSO$_4$ and concentrated. The residue was subjected to silica gel column chromatography to yield 2-(2-Boc-amino-1-hydroxyhexyl)-5-(4-pyridyl)-1,3,4-oxadiazole (950 mg); MS: 361.4 (M−1), 363.4 (M+1).

2-(2-Boc-amino-1-hydroxyhexyl)-5-(4-pyridyl)-1,3,4-oxadiazole (950 mg, 2.62 mmol) and MeCl$_2$ (5 ml) were mixed and TFA (1 ml) was added at room temperature. After stirring for 1 hour, the solvent and excess TFA were removed under vacuum to produce 2-amino-1-(5-(4-pyridyl)-[1,3,4] oxadiazol-2-yl)-1-hexanol TFA salt (1 g); MS: 263.0 (M+1).

Reference 4

3-Cyploroalmethanesulfonyl-2-[(morpholine-4-carbonyl)-amino]-propionic acid

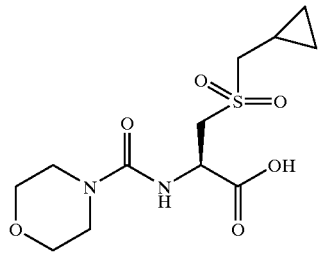

Step 1

To a suspension of L-cysteine (100 g) in ethanol (850 mL) under nitrogen was added over 40 min a solution of sodium hydroxide (2.0 eq., 64.6 g) in ethanol (650 mL) (the sodium hydroxide solution was maintained below 40° C. during its preparation, 3 hours for complete dissolution). After the addition, cyclopropylmethyl bromide (1.1 eq., 122.5 g) was added over 20 minutes while maintaining the temperature at 25–30° C. with a cold bath. The resulting white slurry was stirred for another 18 hours and then quenched by adding 2N HCl (0.73 eq., 300 mL) over 20 minutes. The thick suspension was concentrated (100 mbars, 52° C. bath) to about 400 mL (1.5L ethanol/water distilled) and then water (750 mL) was added. The pH (9.6) was adjusted to pH 6.5 with 2N HCl and the mixture was stirred at 4° C. for 2 hours and then filtered. The cake was washed five times with water (100 mL) and then dried in vacuum to afford S-cyclopropylmethyl-L-cysteine (128.2 g, 88.6% yield).

Step 2

Triethylamine (2.2 eq., 176 mL) was added over 15 minutes to a suspension of S-cyclopropylmethyl-L-cysteine (100 g) in acetonitrile (1.5L) and water (150 mL) under nitrogen. Morpholine carbonyl chloride (1.15 eq., 100 g) was added to the suspension over 4 hours at room temperature. The resulting solution was stirred for another 18 hours at room temperature and the mixture was concentrated to about 400 mL (100 mbars, 50° C. bath). The mixture was diluted with water (250 mL) and the pH (5.3) was adjusted to 12.5 by adding 2N sodium hydroxide (2.1 eq., 616 mL). The aqueous mixture was washed three times with dichloromethane (500 mL). Additional dichloromethane (500 mL) was added and the pH was adjusted to pH 2.0–2.5 by adding 2N HCl (1.0 eq, 285 mL). The aqueous layer was extracted twice with dichloromethane (100 mL). The combined acidic extracts were washed with water (100 mL) and concentrated to about 400 mL. The mixture was then distilled under vacuum (P<=300 mbar, temp <=50° C.) while maintaining the volume constant by adding isopropyl alcohol (400 mL). The mixture was then cooled to 15–20° C. and H$_2$WO$_4$ (0.02 eq., 2.9 g) was added followed by 30% hydrogen peroxide solution (2.2 eq., 130 mL). The mixture was stirred overnight at room temperature then cooled to 0–5° C. and a solution of Na$_2$S$_2$O$_3$ (0.2 eq., 21.6 g) in water (100 mL) added. The mixture was extracted with ethyl acetate (1.6L), then twice with a mixture of ethyl acetate and isopropyl alcohol (500 mL, 7/3, v/v). The combined organic layers were dried over Na$_2$SO$_4$ (300 g) and then concentrated to about 250 mL. Residual isopropyl alcohol was distilled under vacuum, keeping the volume constant by adding ethyl acetate (250 mL). The resulting slurry was stirred at room temperature for another hour and then filtered. The solid was washed twice with ethyl acetate (50 mL) and then dried in vacuum to afford the cyclopropyl sulfone (182.6 g, 64.8% yield). The filtrate was concentrated in vacuum, more product was isolated from ethyl acetate (150 mL), washed twice with ethyl acetate (50 mL) and then dried to afford another 27.2 g of acid (14.9%). $^1$H NMR (DMSO-d6): 12.9 (bs, 1H), 7.16 (d, 1H), 4.5 (m, 1H), 3.6–3.42 (m, 5H), 3.35–3.2 (m, 5H), 3.15–3.0 (m, 2H), 1.0 (m, 1H), 0.6 (m, 2H), 0.3 (m, 2H).

MS: 321 (MH$^+$).

Reference 5

3-(2-Methyl-propane-1-sulfonyl)-2-[(morpholine-4-carbonyl)-amino]-propionic acid

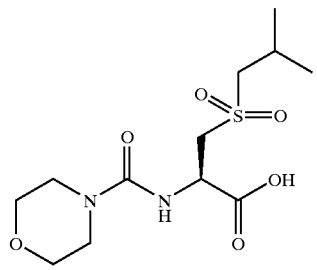

By proceeding in a similar manner to Reference Example 4 above but using isobutyl bromide instead of cyclopropylmethyl bromide, and 10 N sodium hydroxide solution instead of ethanolic sodium hydroxide, in Step 1 there was prepared 3-(2-methyl-propane-1-sulfonyl)-2-[(morpholine-4-carbonyl)-amino]-propionic acid. $^1$H NMR (CDCl$_3$): 10.0 (bs, 1H), 6.1 (d, 1H), 4.8 (m, 1H), 3.75–3.6 (m, 6H), 3.5–3.3 (m, 4H), 3–2.85 (d, 2H), 2.35 (m, 1H), 1.1 (d, 6H). MS: 323 (MH$^+$).

Reference 6

(S)-2-Amino-1-(3-tert-butyl-[1,2,4]oxadiazol-5-yl)-butan-1-ol

A solution of (S)-3-tert-butoxycarbonylamino-2-hydroxy-pentanoic acid (1.63 g, 7 mmol) and N-hydroxy-2,2-dimethyl-propionamidine (0.9 g, 7.75 mmol) in dichloromethane (40 mL) was stirred at 0° C. N-cyclohexylcarbodiimide-N'-methyl polystyrene (1.92 mmol/g, 5.1 g, 9.8 mmol) was added in portions. The reaction mixture was stirred under nitrogen for one hour. The reaction mixture was filtered, the resin washed with dichloromethane and the filtrate evaporated under vacuum to dryness. The residue was dissolved in THF (20 mL), the solution split into five equal parts, which were filled into microwave reactor vials and heated in a microwave reactor at 180° C. for three minutes. The reactors were cooled to room temperature, the solutions combined and the THF evaporated under vacuum. The residue was subjected to flash chromatography (eluting with a gradient from 5% to 65% ethyl acetate in heptane) to give a colorless oil [LC/MS m/z=336 (M+Na$^+$), 214 (M+H$^+$-Boc)].

The colorless oil was dissolved in dichloromethane (45 mL) and trifluoroacetic acid (5 mL) was added. After two hours the reaction was evaporated under vacuum to dryness. The residue was re dissolved in 50 mL of dichloromethane. Silicycle triamine-3 (4.19 g, 16.45 mmol) was added and the mixture stirred at room temperature overnight. The mixture was filtered and washed with dichloromethane. The filtrate was concentrated under vacuum to give (S)-2-amino-1-(3-tert-butyl-[1,2,4]oxadiazol-5-yl)-butan-1-ol (675 mg, 45% overall) as a white solid. Obtained as mixture of diastereomers.

$^1$H NMR (CDCl$_3$, 300 MHz): [4.87 (d, J=4.5 Hz) 4.69 (d, J=3.5 Hz), 1H], [3.18 (ddd, J=8 Hz, 5.5 Hz, 4 Hz) 3.09 (ddd, J=9 Hz, 2×4.5 Hz), 1H], 1.71–1.21 (m, 2H), 1.40 (s, 9H), [1.04 (t, J=7.5 Hz) 1.00 (t, J=7.5 Hz), 3H].

[LC/MS m/z=214 (M+H)]

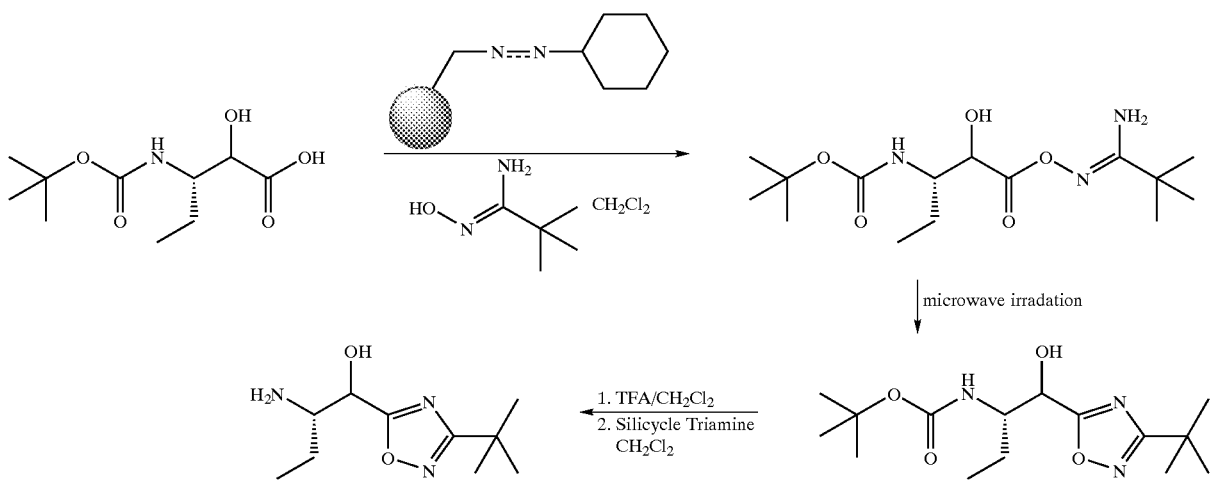

Reference 7

(S)-2-Amino-1-(3-thiophen-2-yl-[1,2,4]oxadiazol-5-yl)-butan-1-ol

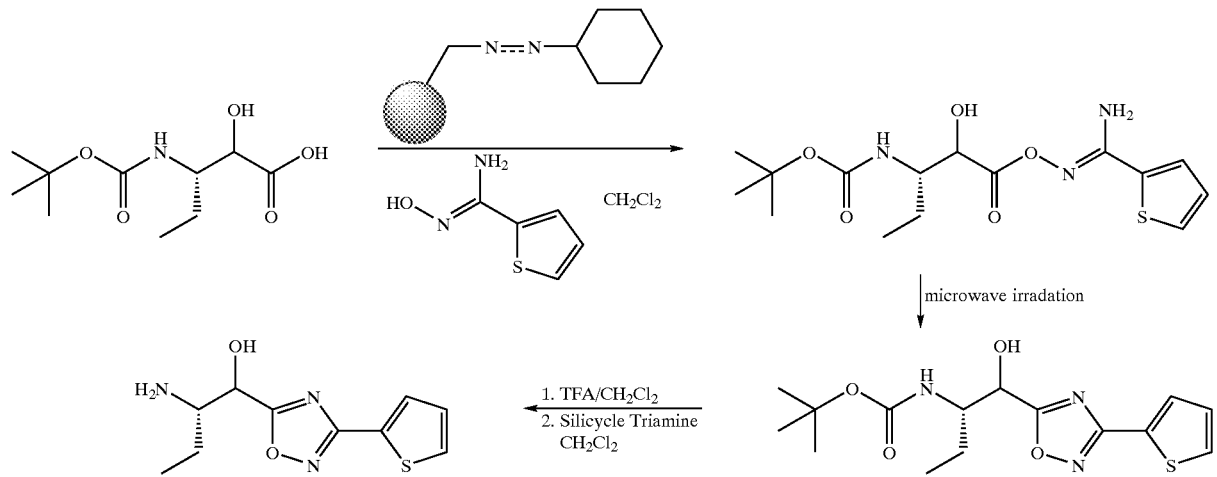

A solution of (S)-3-tert-Butoxycarbonylamino-2-hydroxy-pentanoic acid (2 g, 8.6 mmol) and N-Hydroxy-thiophene-2-carboxamidine (1.35 g, 9.5 mmol) in dichloromethane (40 mL) was stirred at 0° C. N-cyclohexylcarbodiimide-N'-methyl polystyrene (1.90 mmol/g, 6.05 g, 11.5 mmol) was added in portions. The reaction mixture was stirred under nitrogen for four hours at 0° C. and then for 15 hours at room temperature. The reaction mixture was filtered, the resin washed with dichloromethane and the filtrate evaporated under vacuum to dryness. The residue was dissolved in tetrahydrofuran (20 mL), the solution split into five equal parts, which were filled into microwave reactor vials and heated in a microwave reactor at 180° C. for four minutes. The reactors were cooled to room temperature, the solutions combined and the THF evaporated under vacuum. The residue was purified via flash chromatography (eluted with a gradient from 5% to 60% ethyl acetate in heptane) to give a colorless oil. [LC/MS m/z=362 (M+Na$^+$), 240 (M+H$^+$-Boc)].

The colorless oil was dissolved in dichloromethane (45 mL) and trifluoroacetic acid (5 mL) was added. After two hours the reaction mixture was evaporated under vacuum to dryness. The residue was re dissolved in 50 mL of dichloromethane. Silicycle triamine-3 (3.47 g, 13.65 mmol) was added and the mixture stirred at room temperature overnight. The mixture was filtered and washed with dichloromethane. The filtrate was concentrated under vacuum to give (S)-2-Amino-1-(3-thiophen-2-yl-[1,2,4]oxadiazol-5-yl)-butan-1-ol, a mixture of diastereomers, (560 mg, 27% overall) as off-white solid. $^1$H NMR (CDCl$_3$, 300 MHz): [7.84 (d, J=1 Hz) 7.82 (d, J=1 Hz), 1H], [7.53 (dd, J=5 Hz, 1 Hz) 7.52 m, 1H], [7.18 (d, J=5 Hz) 7.17 (d, J=5 Hz), 1H], [4.94 (d, J=5 Hz) 4.76 (d, J=4 Hz), 1H], [3.26 (ddd, J=8 Hz, 5.5 Hz, 3.5 Hz) 3.13 (ddd, J=9 Hz, 2×4.5 Hz), 1H], 1.79–1.21 (m, 2H), [1.07 (t, J=7.5 Hz) 1.04 (t, J=7.5 Hz), 3H]. LC/MS m/z=240 (M+H).

Reference 8

{(S)-1-[(5-tert-Butyl-1,2,4-oxadiazol-3-yl)-hydroxy-methyl]-propyl}-carbamic acid tert butyl ester

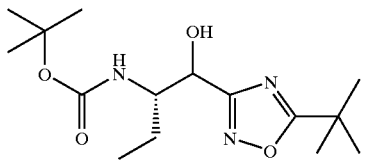

A suspension of {(S)-1-[Hydroxy-(N-hydroxycarbamimidoyl)-methyl]-propyl}-carbamic acid tert-butyl ester (3.24 g, 13.12 mmol) in toluene (25 ml ) was treated with trimethyl acetic anhydride (2.93 ml, 14.44 mmol) and 1-ethyl-3-methyl-1H-imidazolium hexafluorophosphate (0.38 g, 1.48 mmol) and the mixture heated at 200° C. in a microwave (Smith Creator, S00219) for 20 minutes. Solvent evaporated under reduced pressure. The residue was subjected to flash chromatography eluting with a mixture of ethyl acetate and heptane to give {(S)-1-[(5-tert-Butyl-1,2,4-oxadiazol-3-yl)-hydroxy-methyl]-propyl}-carbamic acid tert butyl ester as a brown oil (2.73 g) (mixture of diastereoisomers).

$^1$H NMR (CDCl$_3$): 4.92–4.69 (m, 2H), 4.05–3.85 (m, 1H), 1.73–1.48 (m, 2H), 1.45 & 1.44 (2×s, 9H), 1.43 & 1.39 (2×s, 9H), 0.99 & 0.96 (2×t, J=7.5 Hz, 3H). MS: 314 (MH$^+$).

Reference 9

(S)-2-Amino-1-(5-tert-butyl-1,2,4-oxadiazol-3-yl)-butan-1-ol

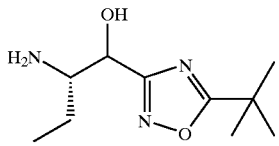

A solution of {(S)-1-[(5-tert-Butyl-1,2,4-oxadiazol-3-yl)-hydroxy-methyl]-propyl}-carbamic acid tert butyl ester (2.11 g, 6.72 mmol) in methylene chloride (20 ml) was treated with trifluoroacetic acid (5.18 ml, 67.25 mmol) and stirred at room temperature for 3 hours. The solvent was evaporated under reduced pressure. The residue was dissolved in methylene chloride (100 ml) and treated with PS-trisamine from Argonaut Technologies (5.38 g, 20.18 mmol, 3.75 mmol/g loading) and the reaction stirred at room temperature for 4 h, filtered and the filtrate evaporated to give (S)-2-amino-1-(5-tert-butyl-1,2,4-oxadiazol-3-yl)-butan-1-ol as an orange oil (975 mg) (mixture of diastereoisomers). $^1$H NMR (CDCl$_3$): 4.73 & 4.58 (2×d, J=5 Hz, 1H), 3.12–3.00 (m, 1H), 2.64–2.31 (bs, 3H), 1.69–1.44 (m, 2H), 1.43 (s, 9H), 0.99 & 0.97 (2×t, J=7.5 Hz, 3H). MS: 214 (MH$^+$).

Reference 10

(S)-2-Amino-1-(3-cyclopropyl-1,2,4-oxadiazol-5-yl)-butan-1-ol

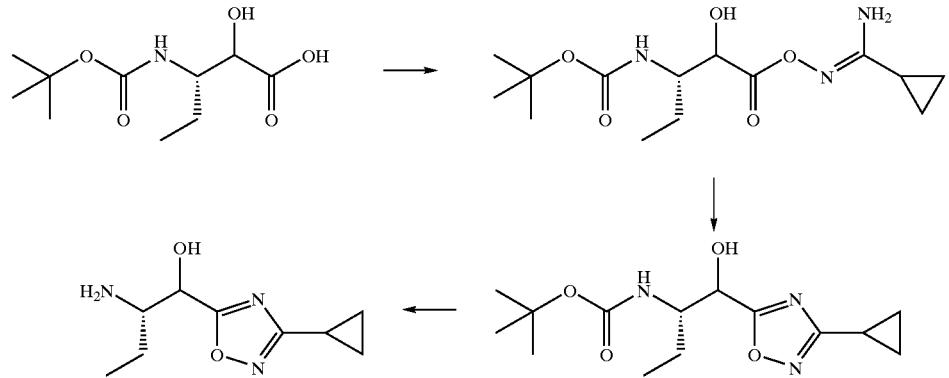

A solution of (S)-3-tert-Butoxycarbonylamino-2-hydroxy-pentanoic acid (2.00 g, 8.57 mmol) and N-hydroxy-cyclopropanecarboxamidine (1.03 g, 10.29 mmol) in dichloromethane (20 mL) was stirred at 0° C. and 1.25 equivalents of N-cyclohexylcarbodiimide-N'-methyl polystyrene (1.70 mmol/g, 6.30 g, 10.72 mmol) was added in portions. The reaction mixture stirred under nitrogen for three hours while warming to 15° C. The reaction mixture was filtered, the resin washed with dichloromethane and the filtrate evaporated under vacuum to dryness. [LC/MS m/z=338 (M+H+Na)].

The residue was dissolved in tetrahydrofuran (20 mL) and heated in a microwave reactor (Smith Creator) at 160° C. for three minutes, cooled to room temperature and evaporated under vacuum to dryness. [LC/MS m/z=320 (M+H+Na)].

The residue was dissolved in dichloromethane (50 mL) and stirred at room temperature as a 50 mL solution of 50% trifluoroacetic acid in dichloromethane was added dropwise. After three hours the reaction was evaporated under vacuum to dryness and dissolved in 50 mL of dichloromethane again. Three equivalents of Silicycle triamine-3 was added and the mixture stirred at room temperature overnight. The mixture was filtered and washed with dichloromethane. Evaporate under vacuum to give 1.04 g (61% overall). [LC/MS m/z=198 (M+H)]

Reference 11

(S)-2-Amino-1-(3-phenyl-1,2,4-oxadiazol-5-yl)-butan-1-ol

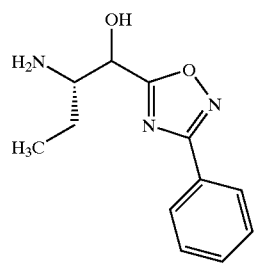

A solution of (S)-3-tert-Butoxycarbonylamino-2-hydroxy-pentanoic acid (2.00 g, 8.57 mmol) and N-hydroxy-benzamidine (1.3 g, 9.5 mmol) in dichloromethane (40 mL) was stirred at 0° C. N-cyclohexylcarbodiimide-N'-methyl polystyrene (1.90 mmol/g, 6 g, 11.4 mmol) was added in portions. The reaction mixture was stirred under nitrogen for one hour. The reaction mixture was filtered, the resin washed with dichloromethane and the filtrate evaporated under vacuum to dryness. [LC/MS m/z=352 (M+H$^+$), 296(M+H$^+$-isobutene)]. The residue was dissolved in tetrahydrofuran (20 mL) and heated in a microwave reactor (Smith Creator) at 180° C. for three minutes, cooled to room temperature and evaporated under vacuum to dryness. The residue was purified via flash chromatography (eluted with a gradient from 5% to 65% ethyl acetate in heptane) to give the product as a white solid [LC/MS m/z=356 (M+Na$^+$), 234 (M+H$^+$-Boc)].

It was dissolved in dichloromethane (45 mL) and trifluoroacetic acid (5 mL) was added. After two hours the reaction was evaporated under vacuum to dryness. The residue was redissolved in 50 mL of dichloromethane. Silicycle triamine-3 (9.9 g, 39 mmol) was added and the mixture stirred at room temperature overnight. The mixture was filtered and washed with dichloromethane. The filtrate was concentrated under vacuum to give 775 mg (38% overall) product as a white solid. [LC/MS m/z=234 (M+H)]. $^1$HNMR (CDCl$_3$) 8.12–8.06 (m, 2H), 7.54–7.45 (m, 3H), 4.93 & 4.75 (2×d, J=5 Hz & 3.5 Hz, 1H), 3.25 & 3.11 (2×m, 1H), 1.78–1.42 (2×m, 2H), 1.04 & 1.01 (2×t, J=7.5 Hz, 3H).

Reference 12

(S)-2-Amino-1-(5-phenyl-[1,2,4]oxadiazol-3-yl)-butan-1-ol

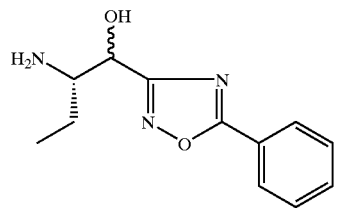

Synthesized as described in the following reaction scheme:

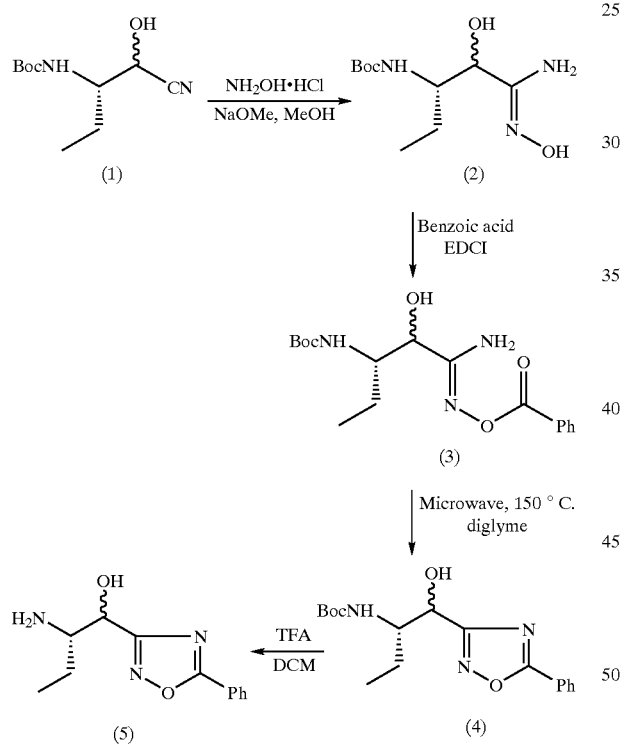

{(S)-1-[Hydroxy-(N-hydroxycarbamimidoyl)-methyl]-propyl}-carbamic acid tert-butyl ester (2)

A solution of (2-cyano-1-ethyl-2-hydroxy-ethyl)-carbamic acid tert-butyl ester (9.53 g, 44 mmol) in methanol (80 ml) was cooled to 0° C. and treated successively with hydroxylamine hydrochloride (3.05 g, 44 mmol) in methanol (80 ml) and 25% sodium methoxide solution in methanol (10.2 ml). After stirring at 0° C. for 5 minutes the reaction mixture stirred at room temperature for 5 hours and then evaporated. The residue was partitioned between ethyl acetate and water. The organic layer was separated, dried (MgSO$_4$) and then evaporated under reduced pressure. The residual yellow oil was subjected to mplc, eluting with a mixture of ethyl acetate and heptane to give {(S)-1-[hydroxy-(N-hydroxycarbamimidoyl)-methyl]-propyl}-carbamic acid tert-butyl ester (3.5 g) as white solid. MS: M(H$^+$) 248.

{1-[Hydroxy-(N-benzoyloxycarbamimidoyl)-methyl]-propyl}-carbamic acid tert-butyl ester (3)

A solution of {1-[hydroxy-(N-hydroxycarbamimidoyl)-methyl]-propyl}-carbamic acid tert-butyl ester (2) (2.5 g, 10 mmol) in dichloromethyl (125 ml) was treated with benzoic acid (1.36 g, 11 mmol), EDCI (2.14 g, 11 mmol), HOBT (1.37 g, 10 mmol) and triethylamine (1.35 mL, 11 mmol) and stirred at room temperature overnight. The reaction mixture was washed with saturated sodium bicarbonate solution, then water, then dried over Na$_2$SO$_4$ and then evaporated under reduced pressure. The residue was subjected to mplc eluting with 1% triethylamine in 2:3 v/v ethyl acetate and heptane mixture to give {1-[hydroxy-(N-benzoyloxycarbamimidoyl)-methyl]-propyl}-carbamic acid tert-butyl ester (850 mg) as a yellow solid. MS: MH$^+$352.

2-Amino-1-(5-phenyl-[1,2,4]oxadiazol-3-yl)-butan-1-ol (5)

A solution of (3) (1.5 g, 4.3 mmol) in diglyme was heated at 150° C. in a microwave reactor (Smith Creator, S00219) for 40 minutes. Solvent evaporated under vacuum in Genevac Evaporator at 80° C. for 3 hours to give a brown solid. This was taken in dichloromethane (40 ml) and treated with trifluoroacetic acid at room temperature for 2 hours. Solvent evaporated to dryness under reduced pressure, crude taken in water, washed with DCM, aqueous layer basified with 1M NaOH solution and extracted with dichloromethane. Organic layer dried over Na$_2$SO$_4$ and evaporated under reduced pressure to give 2-amino-1-(5-phenyl-[1,2,4] oxadiazol-3-yl)-butan-1-ol (300 mg) as a pale brown solid. $^1$HNMR (CDCl$_3$) 8.14–8.10 (m, 2H), 7.59–7.47 (m, 3H), 4.83 & 4.65 (d, J=5 Hz, 1H), 3.18–3.05 (2m, 1H), 1.71–1.20 (m, 2H), 1.05–0.97 (2×t, J=7.2 Hz, 3H).

Reference 13

(S)-2-Amino-1-(5-trifluoromethyl-1,2,4-oxadiazol-3-yl)-butan-1-ol; compound with trifluoro-acetic acid

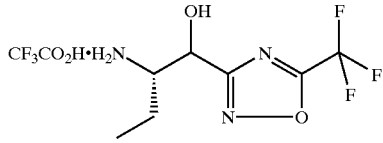

A solution of {(S)-1-[hydroxy-(N-hydroxycarbamimidoyl)-methyl]-propyl}-carbamic acid tert-butyl ester (452 mg, 1.83 mmol) in dioxane (5 mL) was treated with trifluoroacetic anhydride (0.349 ml, 2.47 mmol) and heated at 100° C. in a microwave reactor (Smith Creator, S00219) for 7 minutes. Solvent evaporated under reduced pressure and the crude was subjected to flash chromatography eluting with a mixture of ethyl acetate and heptane to give {(S)-1-[hydroxy-(5-trifluoromethyl-1,2,4-oxadiazol-3-yl)-methyl]-propyl}-carbamic acid tert-butyl ester as a brown solid (476 mg) (mixture of diastereoisomers).
$^1$H NMR (CDCl$_3$): 5.00 (d, J=4 Hz, 1H), 4.82, 4.65 (bd, J=7 Hz, 1H), 4.00, 3.85 (broad m, 1H), 1.78–1.52 (m, 1H), 1.52–1.32 (m, 1H), 1.44, 1.37 (2×s, 9H), 1.02 (2×t, J=7 Hz &4 Hz, 3H). MS: 348 (M+Na)

A solution of {(S)-1-[hydroxy-(5-trifluoromethyl-1,2,4-oxadiazol-3-yl)-methyl]-propyl}-carbamic acid tert-butyl ester (3.6 g, 0.011 mol) in methylene chloride (15 mL) was treated with trifluoroacetic acid (8.53 mL, 0.111 mol) and stirred at room temperature for 3 hours. Solvent evaporated under reduced pressure to give (S)-2-amino-1-(5-trifluoromethyl-1,2,4-oxadiazol-3-yl)-butan-1-ol; compound with trifluoro-acetic acid as a brown oil (4.42 g) (mixture of diastereoisomers). $^1$H NMR (CDCl$_3$): 8.22 (bs, 2H), 7.04 (bs, 1H), 5.14, 4.90 (d, J=4 Hz & 7 Hz, 1H), 3.40–3.28 (m, 1H), 1.64–1.37 (m, 2H), 0.80 (2×t, J=7 Hz, 3H).

MS: 226 (MH$^+$)

Reference 14

(S)-2-Amino-1-(5-ethyl-1,2,4-oxadiazol-3-yl)-butan-1-ol; compound with trifluoro-acetic acid

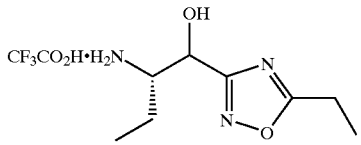

A solution of {(S)-1-[hydroxy-(N-hydroxycarbamimidoyl)-methyl]-propyl}-carbamic acid tert-butyl ester (525 mg, 2.13 mmol) in dioxane (5 mL) was treated with propionic anhydride (0.300 ml, 2.34 mmol) and heated at 150° C. in a microwave reactor (Smith Creator, S00219) for 35 minutes. Solvent evaporated under reduced pressure and the crude was subjected to flash chromatography eluting with a mixture of ethyl acetate and heptane to give {(S)-1-[(5-ethyl-1,2,4-oxadiazol-3-yl)-hydroxy-methyl]-propyl}-carbamic acid tert-butyl ester as a yellow solid (406 mg) (mixture of diastereoisomers). $^1$H NMR (CDCl$_3$): 4.98–4.72 (m, 2H), 4.00, 3.88 (m, 1H), 3.64, 3.45 (bs, 1H), 2.89 (2×q, J=7.6 Hz, 2H), 1.69 (m, 1H), 1.47 (m, 1H), 1.45, 1.39 (2×s, 9H), 1.44–1.36 (m, 3H), 0.98 (2×t, J=9 Hz & 7 Hz, 3H). MS: 308 (M+Na)

A solution of {(S)-1-[(5-ethyl-1,2,4-oxadiazol-3-yl)-hydroxy-methyl]-propyl}-carbamic acid tert-butyl ester (214 mg, 0.751 mmol) in methylene chloride (5 mL) was treated with trifluoroacetic acid (0.578 mL, 7.504 mmol) and stirred at room temperature for 3 hours. Solvent evaporated under reduced pressure to give (S)-2-amino-1-(5-ethyl-1,2,4-oxadiazol-3-yl)-butan-1-ol trifluoroacetate, a mixture of diastereoisomers, (224 mg) as a brown oil.

MS: 186 (MH$^+$). $^1$H NMR (CDCl$_3$): 8.10–7.33 (2×bs, 3H), 5.24, 5.07 (d, J=3.5 Hz & 5.5 Hz, 1H), 3.77, 3.62 (bs, 1H), 2.91 (2×q, J=7 Hz, 2H), 1.78 (m, 1H), 1.76–1.40 (m, 1H), 1.39 (2×t, J=7 Hz, 3H), 1.02 (2×t, J=7.5 Hz, 3H).

Reference 15

{(S)-1-[Hydroxy-(5-thiophen-3-yl-1,2,4-oxadiazol-3-yl)-methyl]-propyl}-carbamic acid tert-butyl ester

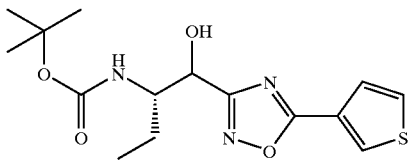

A suspension of {(S)-1-[hydroxy-(N-hydroxycarbamimidoyl)-methyl]-propyl}-carbamic acid tert-butyl ester (2.4 g, 9.7 mmol) in dioxane (15 ml) was treated with thiophene carbonyl chloride (1.45 g, 9.9 mmol) and triethylamine (1.36 ml, 9.8 mmol) and the mixture heated at 150° C. in a microwave (Smith Creator, S00219) for 15 minutes. Solvent evaporated under reduced pressure. The residue was subjected to flash chromatography eluting with a mixture of ethyl acetate and heptane to give {(S)-1-[hydroxy-(5-thiophen-3-yl-1,2,4-oxadiazol-3-yl)-methyl]-propyl}-carbamic acid tert-butyl ester, a mixture of diastereoisomers, (144 mg) as a brown solid. $^1$H NMR (CDCl$_3$): 8.21 (m, 1H), 7.66 (m, 1H), 7.45 (m, 1H), 4.92–4.69 (m, 2H), 5.02–4.80 (m, 2H), 4.10–3.85 (2×m, 1H), 1.80–1.45 (m, 2H), 1.46 & 1.38 (2×s, 9H), 1.01 & 0.99 (2×t, J=7.5 Hz, 3H). MS: 340 (MH$^+$).

Reference 16

(S)-2-Amino-1-(5-thiophen-3-yl-1,2,4-oxadiazol-3-yl)-butan-1-ol

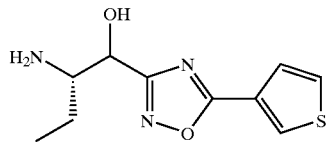

By proceeding in a similar manner to that described for Reference Example 9 above, but using there was prepared (S)-2-amino-1-(5-thiophen-3-yl-1,2,4-oxadiazol-3-yl)-butan-1-ol.

1H NMR (CDCl$_3$): 8.24–8.18 (2×dd, J=1 Hz & 3 Hz, 1H), 7.69–7.62 (2×dd, J=1 Hz & J=5 Hz, 1H), 7.43 (dd, J=3.0 Hz & J=5.0 Hz), 4.88 & 4.70 (2×d, J=4.4 Hz, 1H), 3.27–3.11 (m, 1H), 3.05–2.45 (bs, 3H), 1.74–1.21 (m, 2H), 1.02 & 0.99 (2×t, J=7.5 Hz, 3H). MS: 240 (MH$^+$).

Reference 17

{(S)-1-[(3-Ethyl-1,2,4-oxadiazol-5-yl)-hydroxy-methyl]-propyl}-carbamic acid tert-butyl ester

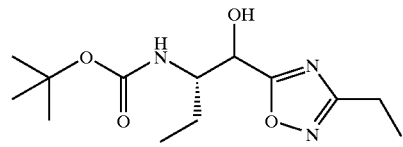

A solution of (S)-3-tert-butoxycarbonylamino-2-hydroxy-pentanoic acid (4.00 g, 17.2 mmol) and N-hydroxy-propionamidine (1.87 g, 21.5 mmol) in dichloromethane (50 mL) was stirred at 0° C. and N-cyclohexylcarbodiimide-N'-methyl polystyrene (1.90 mmol/g, 10 g, 19 mmol) was added in portions. The reaction mixture was stirred under nitrogen for three hours while warming to 15° C. and stirred at room temperature for 48 hours. The reaction mixture was filtered, the resin washed three times with dichloromethane (50 mL), the filtrate evaporated under vacuum to dryness and subjected to flash column chromatography eluting with 10% MeOH in dichloromethane to give a foam (3.51 g). A portion (340 mg) of this material was dissolved in tetrahydrofuran (1.5 mL) and the solution was heated in a microwave reactor (Smith Creator) at 150° C. for three minutes, cooled to room temperature then evaporated under vacuum to dryness. The residue was subjected to flash column chromatography eluting with 5% methanol in dichloromethane to give {(S)-1-[(3-ethyl-1,2,4-oxadiazol-5-yl)-hydroxy-methyl]-propyl}-carbamic acid tert-butyl ester as viscous oil (236 mg). MS: 308 (M+Na$^+$).

Reference 18

(S)-2-Amino-1-(3-ethyl-1,2,4-oxadiazol-5-yl)-butan-1-ol

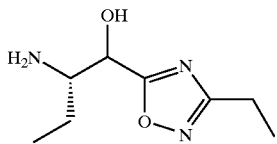

A solution of {(S)-1-[(3-ethyl-1,2,4-oxadiazol-5-yl)-hydroxy-methyl]-propyl}-carbamic acid tert-butyl ester (3.67 g, 12.87 mmol) in dichloromethane (50 mL) was treated with trifluoroacetic acid (10 mL) and the mixture was stirred at room temperature for 1 hour. The reaction mixture was diluted with toluene then evaporated under vacuum to dryness. The residue was dissolved in dichloromethane (75 mL) and the solution was treated with MP-Carbonate (3.3 mmol/g, 6.0 g). This mixture was stirred at room temperature overnight, then filtered, then washed with 10% dichloromethane methanol and evaporated under vacuum to give (S)-2-amino-1-(3-ethyl-1,2,4-oxadiazol-5-yl)-butan-1-ol, a mixture of diastereomers, (2.26 g). $^1$H NMR [(CD3)2SO]: δ 4.61 and 4.54 (d, J=5 Hz, 1H), 2.86 (m, 1H), 2.71 (q, J=8 Hz, 2H), 1.6–1.0 (2×m, 2H), 1.22 (t, J=8 Hz, 3H), 0.88 (m, 3H). MS m/z 186 (M+H).

Example 1

Morpholine-4-carboxylic acid {2-phenylmethanesulfonyl-1-[1-(5-phenyl-[1,3,4]oxadiazole-2-carbonyl)-pentylcarbamoyl]-ethyl}-amide (Compound 1)

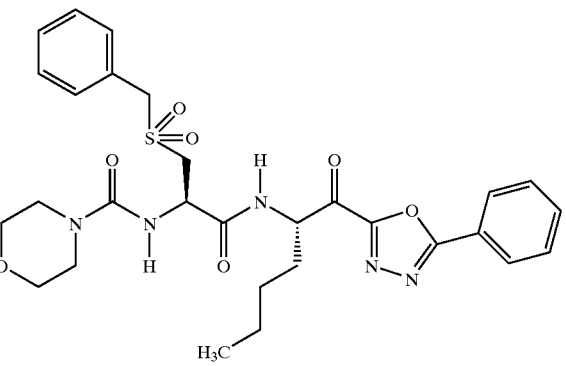

To a stirred mixture of 2-[(morpholine-4-carbonyl)-amino]-3-phenylmethane-sulfonyl-propionic acid (135 mg, 0.37 mmol), 2-amino-1-(5-phenyl-[1,3,4]oxadiazol-2-yl)-1-hexanol TFA salt (135 mg, 0.36 mmol), prepared as in Reference 1, and HOBt (66 mg, 0.43 mmol) in MeCl$_2$ (5 ml), was added EDC (103.6 mg, 0.54 mmol) and N-methylmorpholine (0.4 ml) at room temperature. After stirring for 14 hours, the reaction mixture was extracted with ethyl acetate. The organic layer was washed with saturated NaHCO$_3$, brine, dried with MgSO$_4$ and concentrated. The residue was subjected to silica gel column chromatography to yield morpholine-4-carboxylic acid (1-{1-[hydroxy-(5-phenyl-[1,3,4]oxadiazol-2-yl)-methyl]-pentylcarbamoyl}-2-phenylmethane-sulfonyl-ethyl)-amide (150 mg); MS: 598.6 (M−1), 600.6 (M+1).

Morpholine-4-carboxylic acid (1-{1-[hydroxy-(5-phenyl-[1,3,4]oxadiazol-2-yl)-methyl]-pentylcarbamoyl}-2-phenylmethane-sulfonyl-ethyl)-amide (150 mg, 0.25 mmol), in MeCl$_2$ (5 ml), was treated with Dess-Martin periodinane (183 mg, 0.43 mmol) at room temperature. After stirring for 1 hour, 5 ml of saturated Na$_2$S$_2$O$_3$—NaHCO$_3$ were added. After a further 0.5 hours, the reaction mixture was extracted with ethyl acetate, washed with brine, dried with MgSO$_4$ and concentrated. The residue was purified with silica gel column chromatography to yield morpholine-4-carboxylic acid {2-phenylmethanesulfonyl-1-[1-(5-phenyl-[1,3,4] oxadiazole-2-carbonyl)-pentylcarbamoyl]-ethyl}-amide (84 mg); H$^1$ NMR(DMSO-d): 8.71 (1H, d, J=6.6 Hz, NH), 8.12–8.05 (2H, m), 7.75–7.59 (3H, m), 7.38–7.36 (5H, m), 7.04 (1H, d, J=8.1 Hz, NH), 5.12–5.01 (1H, m), 4.8–4.65 (1H, m), 4.47 (2H, s), 3.58–3.46 (4H, m), 3.35–3.2 (6H, m), 2.05–1.85 (1H, m), 1.8–1.65 (1H, m), 1.5–1.2 (4H, m), 0.87 (3H, t, J=6.9 Hz, CH$_3$); MS: 596.8 9M−1), 598.6 (M+1).

Example 2

Morpholine-4-carboxylic acid {2-(2-difluoromethoxy-phenylmethanesulfonyl)-1-[1-(5-pyridin-3-yl-[1,3,4]oxadiazole-2-carbonyl)-pentylcarbamoyl]-ethyl}-amide (Compound 2)

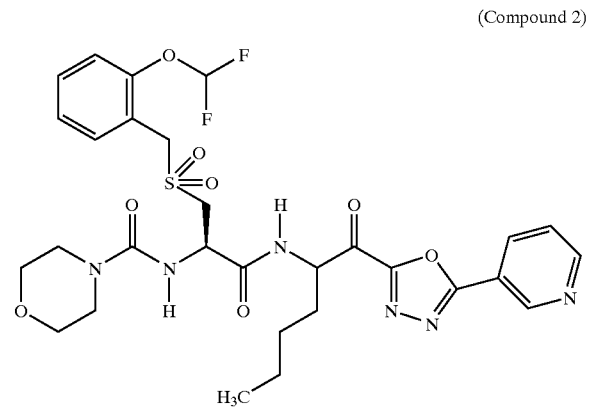

To a stirred mixture of 2-[(morpholine-4-carbonyl)-amino]-3-o-difluoromethoxyphenylmethane-sulfonyl-propionic acid (105.5 mg, 0.25 mmol), 2-amino-1-(5-pyridin-3-yl-[1,3,4]oxadiazol-2-yl)-hexan-1-ol TFA salt (101.6 mg, 0.27 mmol), prepared as in Reference 2, and HOBt (46 mg, 0.3 mmol) in $MeCl_2$ (5 ml), was added EDC (73 mg, 0.38 mmol) and N-methylmorpholine (0.2 ml) at room temperature. After stirring for 14 hours, the reaction mixture was extracted with ethyl acetate. The organic layer was washed with saturated $NaHCO_3$, brine, dried with $MgSO_4$ and concentrated. The residue was subjected to silica gel column chromatography to yield morpholine-4-carboxylic acid (1-{1-[hydroxy-(5-(3-pyridyl)-[1,3,4]oxadiazol-2-yl)-methyl]-pentylcarbamoyl}-2-o-difluoromethoxyphenylmethane-sulfonyl-ethyl)-amide (56 mg); MS: 665.4 (M−1), 667.0 (M+1).

Morpholine-4-carboxylic acid (1-{1-[hydroxy-(5-(3-pyridyl)-[1,3,4]oxadiazol-2-yl)-methyl]-pentylcarbamoyl}-2-o-difluoromethoxyphenylmethane-sulfonyl-ethyl)-amide (56 mg, 0.084 mmol), in $MeCl_2$ (5 ml), was treated with Dess-Martin periodinane (53.4 mg, 0.12 mmol) at room temperature. After stirring for 1 hour, 5 ml of saturated $Na_2S_2O_3$—$NaHCO_3$ were added. After a further 0.5 hours, the reaction mixture was extracted with ethyl acetate, washed with brine, dried with $MgSO_4$ and concentrated. The residue was purified with silica gel column chromatography to yield moripholine-4-carboxylic acid {2-(2-difluoromethoxy-phenylmethanesulfonyl)-1-[1-(5-pyridin-3-yl-[1,3,4]oxadiazole-2-carbonyl)-pentylcarbamoyl]-ethyl}-amide (45 mg); $H^1$ NMR(DMSO-d): 9.247 (1H, d, J=2.2 Hz, NH), 8.86 (1H, dd, J=1.7 Hz, J=4.9 Hz), 8.79 (1H, t, J=5.9 Hz), 8.5–8.45(1H, m), 7.73–7.68(1H, m), 7.5–7.4 (2H, m), 7.3–7.2(2H, m), 7.1(1H, t, J=73.9 Hz), 7.05–6.9 (1H, m), 5.12–5.02(1H, m), 4.78–4.66(1H, m), 4.53(2H, s), 3.55–3.45(5H, m), 3.32–3.26(5H, m), 2.05–1.85(1H, m), 1.8–1.6(1H, m), 1.45–1.2(6H, m), 0.87 (3H, t, J=6.9 Hz, $CH_3$);

MS: 663.4M−1), 665.4(M+1).

Example 3

Morpholine-4-carboxylic acid {2-o-difluoromethoxyphenylmethanesulfonyl-1-[1-(5-(4-pydridyl)-[1,3,4]oxadiazole-2-carbonyl)-pentylcarbamoyl]-ethyl}-amide (Compound 3)

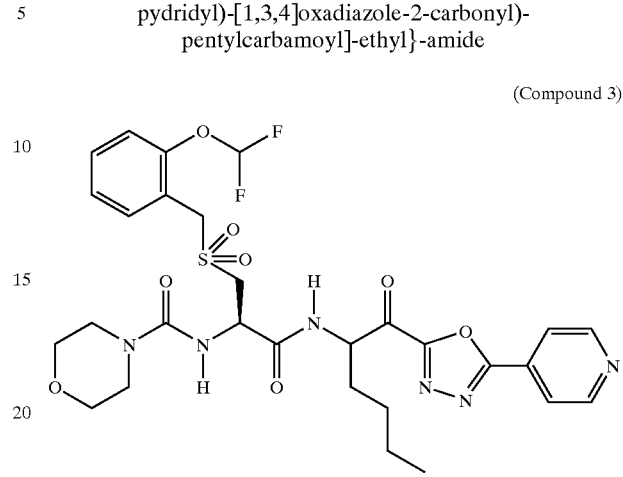

To a stirred mixture of 2-[(morpholine-4-carbonyl)-amino]-3-o-difluoromethoxyphenylmethane-sulfonyl-propionic acid (278 mg, 0.66 mmol), 2-amino-1-(5-(4-pyridyl)-[1,3,4]oxadiazol-2-yl)-1-hexanole TFA salt (248 mg, 0.66 mmol), prepared as above, and HOBt (121 mg, 0.79 mmol) in $MeCl_2$ (5 ml), was added EDC (190 mg, 0.99 mmol) and N-methylmorpholine (0.4 ml) at room temperature. After stirring for 14 hours, the reaction mixture was extracted with ethyl acetate. The organic layer was washed with saturated $NaHCO_3$, brine, dried with $MgSO_4$ and concentrated. The residue was subjected to silica gel column chromatography to yield morpholine-4-carboxylic acid (1-{1-[hydroxy-(5-(4-pyridyl)-[1,3,4]oxadiazol-2-yl)-methyl]-pentylcarbamoyl}-2-o-difluoromethoxyphenylmethane-sulfonyl-ethyl)-amide (430 mg); MS: 665.4 (M−1), 667.2 (M+1). Morpholine-4-carboxylic acid (1-{1-[hydroxy-(5-(4-pyridyl)-[1,3,4]oxadiazol-2-yl)-methyl]-pentylcarbamoyl}-2-o-difluoromethoxyphenylmethane-sulfonyl-ethyl)-amide (400 mg, 0.6 mmol), in $MeCl_2$ (5 ml), was treated with Dess-Martin periodinane (330 mg, 0.78 mmol) at room temperature. After stirring for 1 hour, 5 ml of saturated $Na_2S_2O_3$—$NaHCO_3$ were added. After a further 0.5 hours, the reaction mixture was extracted with ethyl acetate, washed with brine, dried with $MgSO_4$ and concentrated. The residue was purified with silica gel column chromatography to yield morpholine-4-carboxylic acid {2-o-difluoromethoxyphenylmethanesulfonyl-1-[1-(5-(4-pyridyl)-[1,3,4]oxadiazole-2-carbonyl)-pentylcarbamoyl]-ethyl}-amide (148 mg); $H^1$ NMR(DMSO-d): 8.88–8.82 (2H+1H, m), 8.02–7.97 (2H, m), 7.48–7.45 (2H, m), 7.27–7.24 (2H, m), 7.1 (1H, t, J=73.9 Hz), 7.2–6.97 (1H, m), 5.12–5.01 (1H, m), 4.8–4.65 (1H, m), 4.53 (2H, s), 3.58–3.46 (4H, m), 3.35–3.2 (6H, m), 2.05–1.85 (1H, m), 1.8–1.65 (1H, m), 1.5–1.2 (4H, m), 0.87 (3H, t, J=6.9 Hz, $CH_3$); MS: 663.4 (M−1), 665.4 (M+1).

The following compounds were prepared by the methods described and exemplified above:

morpholine-4-carboxylic acid {2-(2-difluoromethoxy-phenylmethanesulfonyl)-1-[1,1-dimethyl-2-oxo-2-(5-pyridin-3-yl-[1,3,4]oxadiazol-2-yl)-ethylcarbamoyl]-ethyl}-amide.

Example 4

Morpholine-4-carboxylic acid [1-[1-(3-cyclopropyl-1,2,4-oxadiazole-5-carbonyl)-propylcarbamoyl]-2-(2-methyl-propane-1-sulfonyl)-ethyl]-amide

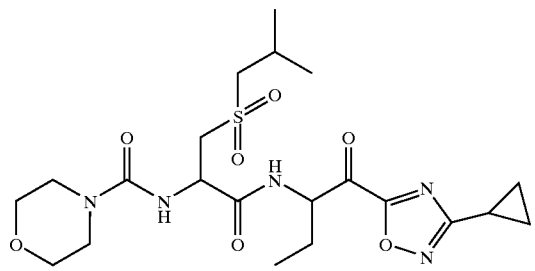

Step 1

A mixture of 3-(2-methylpropane-1-sulfonyl)-2-[(morpholin-4-carbonyl)amino]-propionic acid (163 mg, 0.507 mmol, Reference Example 5), 1-hydroxybenzotriazole hydrate (75 mg, 0.558 mmol), N-cyclohexylcarbodiimide-N'-methyl polystyrene (1.93 mmol/g, 289 mg, 0.558 mmol) and of dichloromethane (5.0 mL) was stirred under nitrogen at room temperature for 10 minutes. A solution of (S)-2-amino-1-(3-cyclopropyl-1,2,4-oxadiazol-5-yl)-butan-1-ol (0.507 mmol, Reference Example 10) in of dichloromethane (2 mL) was added and the reaction mixture stirred at room temperature under nitrogen for four hours. Tris-(2-aminoethyl)amine polystyrene (3.40 mmol/g, 447 mg, 1.521 mmol) and an additional 3.0 mL of dichloromethane were added and the reaction mixture stirred at room temperature under nitrogen overnight. The reaction mixture was filtered and the resin washed with dichloromethane. Evaporated under vacuum to dryness to yield morpholine-4-carboxylic acid (1-{1-[hydroxy-(3-cyclopropyl)-[1,2,4]oxadiazol-2-yl)-methyl]-propylcarbamoyl}-2-methyl-propane-1-sulfonyl-ethyl)-amide (240 mg) as a pale yellow foam. [LC/MS m/z=502 (M+H)].

Step 2

Morpholine-4-carboxylic acid (1-{1-[hydroxy-(3-cyclopropyl)-[1,2,4]oxadiazol-2-yl)-methyl]-propylcarbamoyl}-2-methyl-propane-1-sulfonyl-ethyl)-amide (240 mg) was dissolved in of dichloromethane (7.5 mL) and stirred at 0° C. as 2.5 equivalents of Dess-Martin periodinane (2.63 mL of a 15% solution in DCM) was added. Stirred under nitrogen overnight as the reaction warms to room temperature. Evaporated most of the dichloromethane and dissolved the residue in ethyl acetate. Washed with $NaS_2O_3$ solution, $NaHCO_3$ solution, then brine. The organic phase was dried ($Na_2SO_4$), filtered and evaporated under vacuum to dryness. The residue was subjected to flash chromatography on silica eluting with a gradient from 5% ethyl acetate in dichloromethane to 95% ethyl acetate in dichloromethane to give morpholine-4-carboxylic acid [1-[1-(3-cyclopropyl-1,2,4-oxadiazole-5-carbonyl)-propylcarbamoyl]-2-(2-methyl-propane-1-sulfonyl)-ethyl]-amide, a mixture of diastereomers, (60 mg, 24% overall) as a white solid. $^1$H NMR (CDCl$_3$, 300 MHz): δ [7.87 (d, J=6 Hz), 7.79 (d, J=7 Hz), 1H], [6.10 (d, J=6.5 Hz), 6.06 (d, J=6.2 Hz), 1H], 5.27–5.23 (m, 1H), 4.91–4.85 (m, 1H), 3.72–3.66 (m, 5H), 3.48–3.34 (m, 5H), 3.17–3.05 (m, 2H), 2.42–2.38 (m, 1H), 2.24–2.19 (m, 1H), 2.15–2.07 (m, 1H), 1.90–1.81 (m, 1H), 1.17–1.15 (m, 10H), 1.01 (t, J=7 Hz, 3H). LC/MS m/z=500 (M+H)

Example 5

Morpholine-4-carboxylic acid {2-(2-methyl-propane-1-sulfonyl)-1-[1-(3-thiophen-2-yl-1,2,4-oxadiazole-5-carbonyl)-propylcarbamoyl]-ethyl}-amide

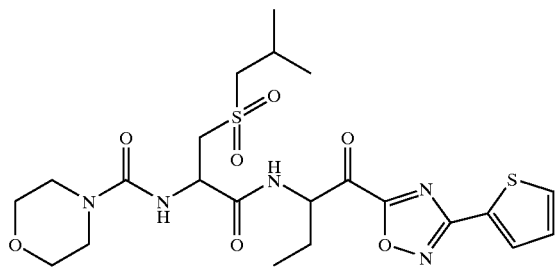

By proceeding in a similar manner to that described in Example 4 above but using (S)-2-amino-1-(3-thiophen-2-yl-[1,2,4]oxadiazol-5-yl)-butan-1-ol (Reference Example 7) instead of (S)-2-amino-1-(3-cyclopropyl-1,2,4-oxadiazol-5-yl)-butan-1-ol in Step 1 there was prepared morpholine-4-carboxylic acid {2-(2-methyl-propane-1-sulfonyl)-1-[1-(3-thiophen-2-yl-1,2,4-oxadiazole-5-carbonyl)-propylcarbamoyl]-ethyl}-amide, a mixture of diastereomers, (110 mg, 40% overall yield) as a white solid. $^1$H NMR (CDCl$_3$, 300 MHz): [7.97 (d, J=6.5 Hz), 7.87 (d, J=6.5 Hz), 1H], 7.91 (d, J=3.8 Hz), 1H, 7.59 (d, J=5 Hz, 1H), 7.22–7.21 (m, 1H), 6.11–6.05 (m, 1H), 5.35–5.32 (m, 1H), 4.93–4.87 (m, 1H), 3.76–3.60 (m, 5H), 3.54–3.35 (m, 5H), 3.18–3.04 (m, 2H), 2.43–2.36 (m, 1H), 2.21–2.15 (m, 1H), 2.00–1.93 (m, 1H), 1.29–1.14 (m, 6H), 1.08 (t, J=7.5 Hz, 3H). LC/MS m/z=542 (M+H)

Example 6

Morpholine-4-carboxylic acid [1-[1-(3-tert-butyl-1,2,4-oxadiazole-5-carbonyl)-propylcarbamoyl]-2-(2-methyl-propane-1-sulfonyl)-ethyl]-amide

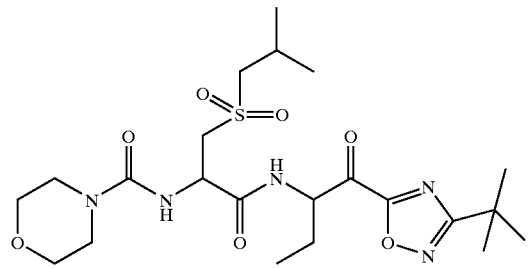

Step 1

N-Cyclohexylcarbodiimide-N'-methylpolystyrene (0.526 g, 1 mmol, loading 1.9 mmol/g) was suspended in dichloromethane (20 mL). 3-(2-methyl-propane-1-sulfonyl)-2-[(morpholine-4-carbonyl)-amino]-propionic acid (0.242 g, 0.6 mmol, reference Example 5) and HOBt (0.114 g, 0.85 mmol) were added and the reaction mixture was stirred for 20 minutes. (2S)-2-Amino-1-(3-tert-butyl-[1,2,4]oxadiazol-5-yl)-butan-1-ol (0.107 g, 0.5 mmol, Reference Example 6) was added and stirring continued for 5 hours. Silicycle Triamine (1.27 g, 5 mmol) was added and the mixture stirred for 15 hours. The reaction mixture was filtered under suction and the filtrate concentrated to give morpholine-4-carboxylic acid [1-{1-[(3-tert-butyl-1,2,4-oxadiazol-5-yl)- hydroxy-methyl]-propylcarbamoyl}-2-(2-methyl-propane-1-sulfonyl)-ethyl]-amide (0.271 g), [LC/MS m/z=518(M+H⁺)].

Step 2

Morpholine-4-carboxylic acid [1-{1-[(3-tert-butyl-1,2,4-oxadiazol-5-yl)-hydroxy-methyl]-propylcarbamoyl}-2-(2-methyl-propane-1-sulfonyl)-ethyl]-amide (0.271 g) was dissolved in dichloromethane (10 mL) and the Dess-Martin periodinane (0.424 g, 1 mmol) was added. The reaction mixture was stirred for two hours and then poured into a mixture of saturated sodium bicarbonate and saturated sodium thiosulfate solution (1/1, 50 mL). The phases were separated and the aqueous phase extracted with dichloromethane. The combined organic phases were washed with sodium bicarbonate solution and brine. The solution was dried with magnesium sulfate and then concentrated under vacuum. The residue was subjected to flash chromatography (gradient from 5% ethyl acetate in heptane to 75% ethyl acetate in heptane) to give morpholine-4-carboxylic acid [1-[1-(3-tert-butyl-1,2,4-oxadiazole-5-carbonyl)-propylcarbamoyl]-2-(2-methyl-propane-1-sulfonyl)-ethyl]-amide, a mixture of diastereomers. ¹H NMR (CDCl₃, 300 MHz): [7.87 (d, J=6.5 Hz) 7.79 (d, J=7 Hz), 1H], [6.11 (d, J=6.5 Hz) 6.06 (d, J=6.5 Hz), 1H], 5.38–5.30 (m, 1H), 4.92–4.13 (m, 1H), 3.78–3.68 (m, 5H), 3.49–3.33 (m, 5H), 3.24–3.04 (m, 2H), 2.47–2.37 (m, 1H), 2.20–2.07 (m, 1H), 1.95–1.85 (m, 1H), 1.45 (s, 9H), 1.17 (d, J=6.5 Hz, 6H), [1.04 (t, J=7.5 Hz) 1.03 (t, J=7.5 Hz), 3H]. [LC/MS m/z=516(M+H⁺)]

Example 7

Morpholine-4-carboxylic acid {2-cyclopropylmethanesulfonyl-1-[1-(5-phenyl-1,2,4-oxadiazole-3-carbonyl)-propylcarbamoyl]-ethyl}-amide

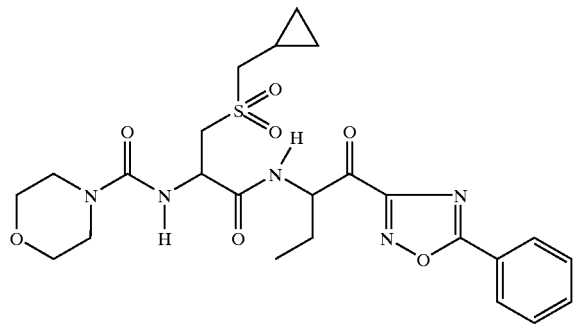

Step 1

A suspension of (R)-3-cyclopropylmethanesulfonyl-2-[(morpholine-4-carbonyl)-amino]-propionic acid (110 mg, 0.344 mmol, Reference Example 4) in methylene chloride (10 mL) was treated with PS-bound N-cyclohexylcarbodiimide (HL 200–400 mesh cross linked with 2% DVB) from Novabiochem (320 mg, 0.618 mmol, 1.93 mmol/g loading) and stirred at room temperature for 10 minutes. HOBt (43 mg, 0.319 mmol) was added followed by (S)-2-amino-1-(5-phenyl-1,2,4-oxadiazol-3-yl)-butan-1-ol (73 mg, 0.313 mmol, Reference Example 12) and the reaction mixture was stirred at room temperature overnight. PS-trisamine from Argonaut Technologies (413 mg, 1.549 mmol, 3.75 mmol/g loading) was added and the reaction was stirred for another 3 hours. The mixture was filtered and the filtrate was evaporated under reduced pressure to give morpholine-4-carboxylic acid (2-cyclopropylmethanesulfonyl-1-{1-[hydroxy-(5-phenyl-1,2,4-oxadiazol-3-yl)-methyl]-propylcarbamoyl}-ethyl)-amide as an orange solid (183 mg). MS: 536 (MH⁺)

Step 2

To a solution of morpholine-4-carboxylic acid (2-cyclopropylmethanesulfonyl-1-{1-[hydroxy-(5-phenyl-1,2,4-oxadiazol-3-yl)-methyl]-propylcarbamoyl}-ethyl)-amide (183 mg, 0.34 mmol) in methylene chloride (10 mL), Dess-Martin Periodinane (200 mg, 0.47 mmol) was added and stirred at room temperature for 2 hours. The reaction mixture was washed with a solution of Na₂S₂O₃ in water (0.26M), saturated bicarbonate, and water, dried over Na₂SO₄ and concentrated under reduced pressure. The residue was subjected to flash chromatography eluting with a mixture of ethyl acetate and heptane to give morpholine-4-carboxylic acid {2-cyclopropylmethanesulfonyl-1-[1-(5-phenyl-1,2,4-oxadiazole-3-carbonyl)-propylcarbamoyl]-ethyl}-amide, a mixture of diastereomers, (45 mg) as an off white solid. ¹H NMR (CDCl₃): 8.22 (d, J=7 Hz, 2H), 7.83, 7.75 (2×d, J=7 Hz, 1H), 7.65 (m, 1H), 7.60–7.51 (m, 2H), 6.10–6.07 (2×d, J=7 Hz, 1H), 5.36 (m, 1H), 5.00–4.86 (m, 1H), 3.79 (m, 1H), 3.74–3.66 (m, 4H), 3.48 (m, 1H), 3.47–3.37 (m, 4H), 3.20–3.07 (m, 2H), 2.24–2.06 (m, 1H), 2.00–1.82 (m, 1H), 1.22 (m, 1H), 1.01 (t, J=7 Hz, 3H), 0.80–0.68 (m, 2H), 0.56–0.38 (m, 2H). MS: 534 (MH⁺).

Example 8

Morpholine-4-carboxylic acid {(R)-2-cyclopropylmethanesulfonyl-1-[(S)-1-(5-trifluoromethyl-1,2,4-oxadiazole-3-carbonyl)-propylcarbamoyl]-ethyl}-amide

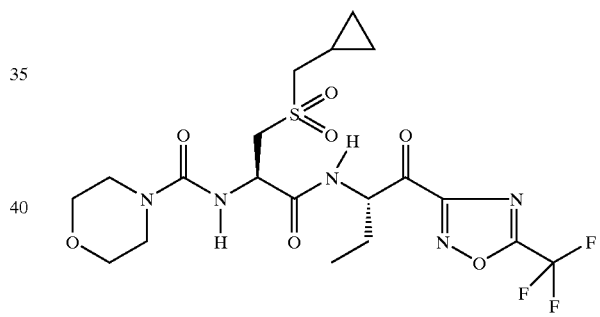

Step 1

A solution of (R)-3-cyclopropylmethanesulfonyl-2-[(morpholine-4-carbonyl)-amino]-propionic acid (266 mg, 0.83 mmol, Reference Example 4) in dimethylformamide (10 mL) was treated successively with (S)-2-amino-1-(5-trifluoromethyl-1,2,4-oxadiazol-3-yl)-butan-1-ol trifluoroacetate (282 mg, 0.83 mmol, Reference Example 13), O-(7-azabenzotriazol-1-yl)-N,N,N',N'-tetramethyluronium hexafluorophosphate (316 mg, 0.83 mmol) and diisopropylethylamine (0.289 mL, 1.66 mmol). Reaction stirred at room temperature overnight. Solvent evaporated under reduced pressure. Residue taken up in ethyl acetate and washed with 1N hydrochloric acid, saturated aqueous bicarbonate solution and water, dried over Na₂SO₄ and solvent evaporated under reduced pressure to give morpholine-4-carboxylic acid ((R)-2-cyclopropylmethanesulfonyl-1-{(S)-1-[hydroxy-(5-trifluoromethyl-1,2,4-oxadiazol-3-yl)-methyl]-propylcarbamoyl}-ethyl)-amide as a brown oil (370 mg). MS: 528 (MH⁺).

Step 2

A solution of morpholine-4-carboxylic acid ((R)-2-cyclopropylmethanesulfonyl-1-{(S)-1-[hydroxy-(5- trifluoromethyl-1,2,4-oxadiazol-3-yl)-methyl]-propylcarbamoyl}-ethyl)-amide (370 mg, 0.70 mmol) in methylene chloride (10 mL) was treated with Dess Martin periodinane (298 mg, 0.70 mmol) and stirred at room temperature for 3 hours. The reaction mixture was washed with an aqueous solution of $Na_2S_2O_3$ (0.26M), saturated aqueous bicarbonate solution and water, dried over $Na_2SO_4$ and the solvent evaporated under reduced pressure. The crude was subjected to flash chromatography eluting with a mixture of ethyl acetate and heptane. It was then further subjected to preparative HPLC (using Gilson 215 liquid handler, and MonoChrom 10 microns C18 column—PN0504—100×212 from MetaChem), eluting with a mixture of acetonitrile and water, going from 10% to 100% acetonitrile in water to give morpholine-4-carboxylic acid {(R)-2-cyclopropylmethanesulfonyl-1-[(S)-1-(5-trifluoromethyl-1,2,4-oxadiazole-3-carbonyl)-propylcarbamoyl]-ethyl}-amide as a white solid (9 mg). $^1$H NMR (CDCl$_3$): 7.87 (d, J=6 Hz, 1H), 5.99 (d, J=6 Hz, 1H), 5.16 (m, 1H), 4.87 (m, 1H), 3.74–3.66 (m, 5H), 3.44–3.36 (m, 5H), 3.14 (d, J=7 Hz, 2H), 2.20–2.02 (m, 1H), 1.98–1.78 (m, 1H), 1.21 (m, 1H), 1.02 (t, J=7 Hz, 3H), 0.82–0.70 (m, 2H), 0.57–0.40 (m, 2H). MS: 526 (MH$^+$)

Example 9

Morpholine-4-carboxylic acid [(1-[(1-(5-ethyl-1,2,4-oxadiazole-3-carbonyl)-propylcarbamoyl]-2-(2-methyl-propane-1-sulfonyl)-ethyl]-amide

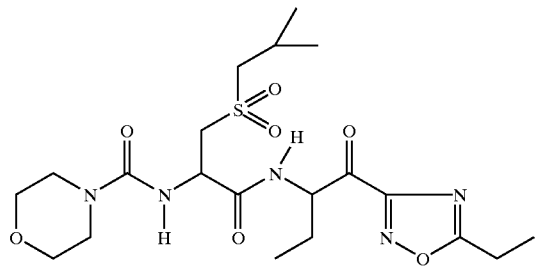

By proceeding in a similar manner to Example 8 above but using (R)-3-(2-methyl-propane-1-sulfonyl)-2-[(morpholine-4-carbonyl)-amino]-propionic acid (Reference Example 5) instead of (R)-3-cyclopropylmethanesulfonyl-2-[(morpholine-4-carbonyl)-amino]-propionic acid and (S)-2-amino-1-(5-ethyl-1,2,4-oxadiazol-3-yl)-butan-1-ol (Reference Example 14) instead of (S)-2-amino-1-(5-trifluoromethyl-1,2,4-oxadiazol-3-yl)-butan-1-ol trifluoroacetate, in Step 1, there was prepared morpholine-4-carboxylic acid [1-[1-(5-ethyl-1,2,4-oxadiazole-3-carbonyl)-propylcarbamoyl]-2-(2-methyl-propane-1-sulfonyl)-ethyl]-amide, a mixture of diastereomers. $^1$H NMR (CDCl$_3$): 7.81, 7.72 (2×d, J=6.5 Hz, 1H), 6.14–6.01 (2×d, J=6.5 Hz, 1H), 5.28 (m, 1H), 4.95–4.81 (m, 1H), 3.75–3.65 (m, 5H), 3.54–3.32 (m, 5H), 3.12(m, 2H), 3.01 (q, J=7.5 Hz, 2H), 2.45–2.30 (m, 1H), 2.17–2.04 (m, 1H), 1.93–1.78 (m, 1H), 1.44 (t, J=7.5 Hz, 3H), 1.13 (d, J=6.5 Hz, 6H), 0.98 (t, J=7.5 Hz, 3H).

MS: 488 (MH$^+$).

Example 10

{(R)-2-(2-Methyl-propane-1-sulfonyl)-1-[(S)-1-(5-thiophen-3-yl-1,2,4-oxadiazole-3-carbonyl)-propylcarbamoyl]-ethyl}-amide

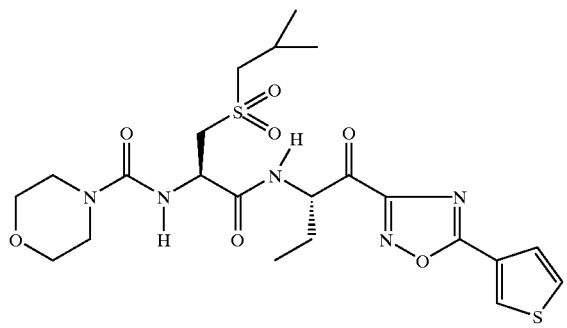

By proceeding in a similar manner to Example 8 above but using (R)-3-(2-methyl-propane-1-sulfonyl)-2-[(morpholine-4-carbonyl)-amino]-propionic acid (Reference Example 5) instead of (R)-3-cyclopropylmethanesulfonyl-2-[(morpholine-4-carbonyl)-amino]-propionic acid and (S)-2-amino-1-(5-thiophen-3-yl-1,2,4-oxadiazol-3-yl)-butan-1-ol (Reference Example 16) instead of (S)-2-amino-1-(5-trifluoromethyl-1,2,4-oxadiazol-3-yl)-butan-1-ol trifluoroacetate, there was prepared morpholine-4-carboxylic acid {(R)-2-(2-methyl-propane-1-sulfonyl)-1-[(S)-1-(5-thiophen-3-yl-1,2,4-oxadiazole-3-carbonyl)-propylcarbamoyl]-ethyl}-amide. $^1$H NMR (CDCl$_3$): 8.33 (dd, J=3 and 1.1 Hz, 1H), 7.83 (d, J=6.5 Hz, 1H), 7.73 (dd, J=5.1 and 1.1 Hz, 1H), 7.48 (dd, J=5.0 and 3.0 Hz, 1H), 6.04 (d, J=6.5 Hz, 1H), 5.33 (m, 1H), 4.86 (m, 1H), 3.78–3.66 (m, 5H), 3.49–3.35 (m, 5H), 3.22–3.05 (m, 2H), 2.46–2.32 (m, 1H), 2.22–2.07 (m, 1H), 1.98–1.82 (m, 1H), 1.14 (d, J=7 Hz, 6H), 1.01 (t, J=7.5 Hz, 3H). MS: 542 (MH$^+$).

Example 11

Morpholine-4-carboxylic acid {(R)-1-[(S)-1-(3-tert-butyl-1,2,4-oxadiazole-5-carbonyl)-propylcarbamoyl]-2-cyclopropylmethanesulfonyl-ethyl}-amide

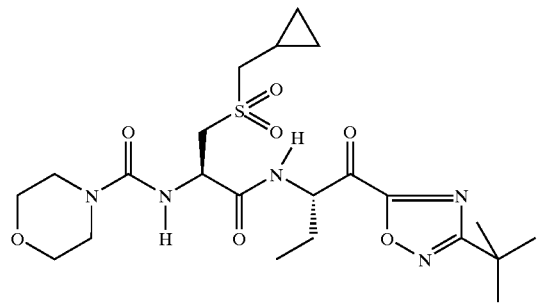

By proceeding in a similar manner to Example 8 above but using (S)-2-amino-1-(3-tert-butyl-1,2,4-oxadiazol-5-yl)-butan-1-ol (Reference Example 6) instead of (S)-2-amino-1-(5-trifluoromethyl-1,2,4-oxadiazol-3-yl)-butan-1-ol trifluoroacetate there was prepared morpholine-4-carboxylic acid {(R)-1-[(S)-1-(3-tert-butyl-1,2,4-oxadiazole-5-carbonyl)-propylcarbamoyl]-2- cyclopropylmethanesulfonyl-ethyl}-amide. ¹H NMR (CDCl₃): 7.80 (d, J=6.5 Hz, 1H), 6.02 (d, J=6.5 Hz, 1H), 5.31 (m, 1H), 4.88 (m, 1H), 3.82–3.66 (m, 5H), 3.50–3.36 (m, 5H), 3.15 (d, J=7 Hz, 2H), 2.20–2.04 (m, 1H), 1.95–1.80 (m, 1H), 1.42 (s, 9H), 1.26–1.15 (m, 1H), 1.00 (t, J=7.5 Hz, 3H), 0.79–0.72 (m, 2H), 0.56–0.41 (m, 2H).

MS : 514 (MH⁺).

Example 12

Morpholine-4-carboxylic acid {(R)-2-(2-methyl-propane-1-sulfonyl)-1-[(S)-1-(5-trifluoromethyl-1,2,4-oxadiazole-3-carbonyl)-propylcarbamoyl]-ethyl}-amide

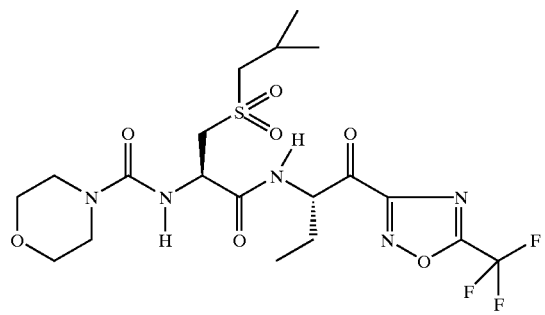

By proceeding in a similar manner to Example 8 above but using (R)-3-(2-methyl-propane-1-sulfonyl)-2-[(morpholine-4-carbonyl)-amino]-propionic acid (Reference Example 5) instead of (R)-3-cyclopropylmethanesulfonyl-2-[(morpholine-4-carbonyl)-amino]-propionic acid there was prepared morpholine-4-carboxylic acid {(R)-2-(2-methyl-propane-1-sulfonyl)-1-[(S)-1-(5-trifluoromethyl-1,2,4-oxadiazole-3-carbonyl)-propylcarbamoyl]-ethyl}-amide. ¹H NMR (CDCl₃): 7.90 (d, J=6 Hz, 1H), 6.00 (d, J=6 Hz, 1H), 5.17(m, 1H), 4.83 (m, 1H), 3.73–3.62 (m, 5H), 3.45–3.36 (m, 5H), 3.13 (m, 2H), 2.45–2.32 (m, 1H), 2.18–2.04 (m, 1H), 1.96–1.80 (m, 1H), 1.14 (d, J=7 Hz, 6H), 1.03 (t, J=7.5 Hz, 3H). MS: 528 (MH⁺).

Example 13

Morpholine-4-carboxylic acid {(R)-1-[(S)-1-(5-tert-butyl-1,2,4-oxadiazole-3-carbonyl)-propylcarbamoyl]-2-phenylmethanesulfonyl-ethyl}-amide

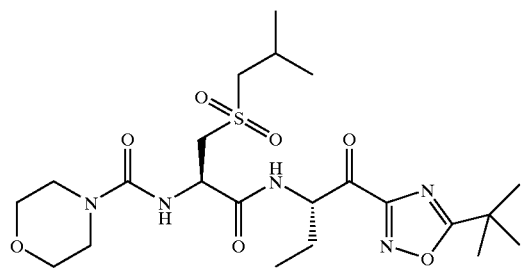

By proceeding in a similar manner to Example 8 above but using (R)-3-(2-methyl-propane-1-sulfonyl)-2-[(morpholine-4-carbonyl)-amino]-propionic acid (Reference Example 5) instead of (R)-3-cyclopropylmethanesulfonyl-2-[(morpholine-4-carbonyl)-amino]-propionic acid and (S)-2-amino-1-(5-tert-butyl-1,2,4-oxadiazol-3-yl)-butan-1-ol (Reference Example 9) instead of (S)-2-amino-1-(5-trifluoromethyl-1,2,4-oxadiazol-3-yl)-butan-1-ol trifluoroacetate there was prepared morpholine-4-carboxylic acid {(R)-1-[(S)-1-(5-tert-butyl-1,2,4-oxadiazole-3-carbonyl)-propylcarbamoyl]-2-phenylmethanesulfonyl-ethyl}-amide. ¹H NMR (CDCl₃): 7.78 (d, J=7 Hz, 1H), 6.04 (d, J=6.5 Hz, 1H), 5.30 (m, 1H), 4.85 (m, 1H), 3.76–3.64 (m, 5H), 3.48–3.34 (m, 5H), 3.13 (m, 2H), 2.47–2.31 (m, 1H), 2.19–2.02 (m, 1H), 1.95–1.80 (m, 1H), 1.48 (s, 9H), 1.14 (d, J=6.5 Hz, 6H), 0.99 (t, J=7.5 Hz, 3H).

MS: 516 (MH⁺).

Example 14

Morpholine-4-carboxylic acid {(R)-1-[(S)-1-(5-tert-butyl-1,2,4-oxadiazole-3-carbonyl)-propylcarbamoyl]-2-phenylmethanesulfonyl-ethyl}-amide

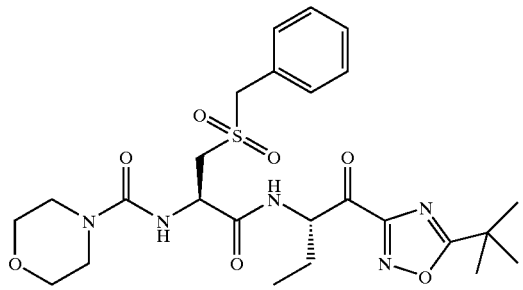

By proceeding in a similar manner to Example 8 above but using (R)-2-[(morpholine-4-carbonyl)-amino]-3-phenylmethanesulfonyl-propionic acid instead of (R)-3-cyclopropylmethanesulfonyl-2-[(morpholine-4-carbonyl)-amino]-propionic acid and (S)-2-amino-1-(5-tert-butyl-1,2,4-oxadiazol-3-yl)-butan-1-ol (Reference Example 9) instead of (S)-2-amino-1-(5-trifluoromethyl-1,2,4-oxadiazol-3-yl)-butan-1-ol trifluoroacetate there was prepared morpholine-4-carboxylic acid {(R)-1-[(S)-1-(5-tert-butyl-1,2,4-oxadiazole-3-carbonyl)-propylcarbamoyl]-2-phenylmethanesulfonyl-ethyl}-amide. ¹H NMR (CDCl₃): 7.67 (d, J=7 Hz, 1H), 7.50–7.34 (m, 5H), 6.01 (d, J=7 Hz, 1H), 5.31 (m, 1H), 4.93 (m, 1H), 4.52 & 4.40 (2×d, J=14 Hz, 2H), 3.76–3.64 (m, 5H), 3.46–3.26 (m, 5H), 2.20–2.06 (m, 1H), 1.94–1.78 (m, 1H), 1.48 (s, 9H), 0.98 (t, J=7.5 Hz, 3H).

MS: 550 (MH⁺).

Example 15

Morpholine-4-carboxylic acid {2-cyclopropylmethanesulfonyl-1-[1-(3-cyclopropyl-1,2,4-oxadiazole-5-carbonyl)-propylcarbamoyl]-ethyl}-amide

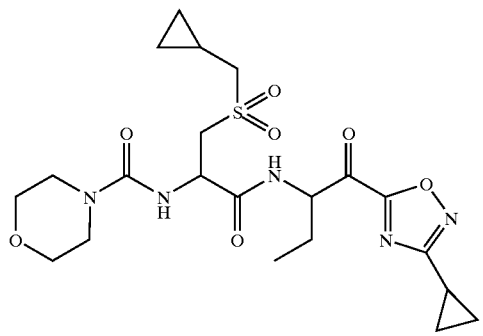

By proceeding in a similar manner to Example 8 above but using (S)-2-amino-1-(3-cyclopropyl-1,2,4-oxadiazol-5-yl)-butan-1-ol (Reference Example 10) instead of (S)-2-amino-1-(5-trifluoromethyl-1,2,4-oxadiazol-3-yl)-butan-1-ol trifluoroacetate there was prepared morpholine-4-carboxylic acid {2-cyclopropylmethanesulfonyl-1-[1-(3-cyclopropyl-1,2,4-oxadiazole-5-carbonyl)-propylcarbamoyl]-ethyl}-amide, a mixture of diastereomers, as a white solid. $^1$H NMR (CDCl$_3$) δ 7.83, 7.74 (d, J=7 Hz, 1H), 6.02 (d, J=7 Hz, 1H), 5.22 (m, 1H), 4.87 (m, 1H), 3.72 (m, 5H), 3.41 (m, 5H), 3.16 (d, 2H), 2.21 (m, 1H), 2.15 (m, 1H), 1.86 (m, 1H), 1.03–1.24 (m, 5H), 0.99 (t, J=7 Hz, 3H), 0.76 (m, 2H), 0.48 (m, 2H). MS (M/Z)=498 (M+H). LC Kromasil KR 100–10 Sil, 250 4.6 mm ID (90% (heptane/THF/ACN//(220/60/14,v/v/v) retention time=24.1 minutes, flow rate 1.5 mL/min.

Example 16

Morpholine-4-carboxylic acid {2-cyclopropylmethanesulfonyl-1-[1-(3-ethyl-1,2,4-oxadiazole-5-carbonyl)-propylcarbamoyl]-ethyl}-amide

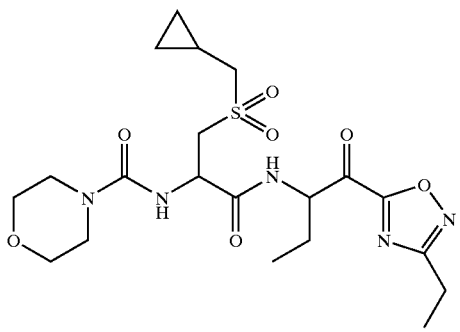

By proceeding in a similar manner to Example 8 above but using (S)-2-amino-1-(3-ethyl-1,2,4-oxadiazol-5-yl)-butan-1-ol trifluoroacetate (Reference Example 14) instead of (S)-2-amino-1-(5-trifluoromethyl-1,2,4-oxadiazol-3-yl)-butan-1-ol trifluoroacetate there was prepared morpholine-4-carboxylic acid {2-cyclopropylmethanesulfonyl-1-[1-(3-ethyl-1,2,4-oxadiazole-5-carbonyl)-propylcarbamoyl]-ethyl}-amide, as a 1:1 mixture of diastereomers. $^1$HNMR (CDCl$_3$) δ 7.85 and 7.75 (2×d, J=6 Hz, 1H), 6.07 (m, 1H), 5.28 (m, 1H), 4.92 (m, 1H), 3.8–3.6 (m, 5H), 3.42 (m, 5H), 3.2–3.1 (m, 2H), 2.88 (q, J=7 Hz, 2H), 2.13 (m, 1H), 1.87 (m, 1H), 1.39 (t, J=7 Hz, 3H), 1.22 (m, 1H), 1.02 (t, J=7 Hz, 3H), 0.75 (m, 2H), 0.48 (m, 2H). MS m/z 486 (M+H)

Example 17

Morpholine-4-carboxylic acid {2-cyclopropylmethanesulfonyl-1-[1-(3-phenyl-1,2,4-oxadiazole-5-carbonyl)-propylcarbamoyl]-ethyl}-amide

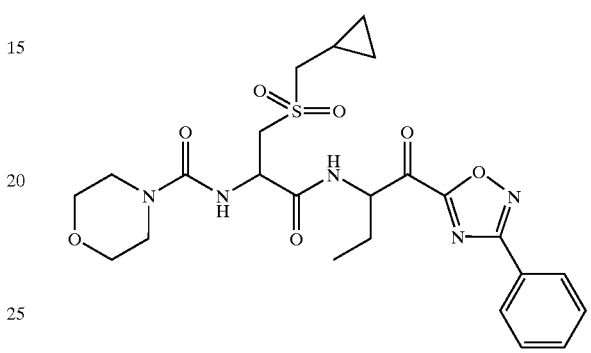

Step 1

To a solution of (R)-3-cyclopropylmethanesulfonyl-2-[(morpholine-4-carbonyl)-amino]-propionic acid (130.5 mg, 0.41 mmol) and di-isopropylethylamine (0.41 mmol, 53.0 mg, 0.0714 mL) in dry dichloromethane (6 mL) was added polystyrene-bound cyclohexyl carbodiimide (2.0 eq., 0.82 mmol, 432 mg) followed by HOBt monohydrate (1.7 eq., 0.70 mmol, 94.2 mg). The mixture was stirred at room temperature for 15 minutes then the (2S)-2-amino-1-(3-phenyl-[1,2,4]oxadiazol-5-yl)-butan-1-ol (0.41 mmol, 95 mg) was added. The mixture was stirred for another 64 hours then silica-bound trisamine (5.0 eq., 2.05 mmol, 569.4 mg) was added. The mixture was stirred for another 2 hours then filtered. The filtrate was concentrated in vacuum and purified over 12 g silica gel, eluted with a mixture of ethyl acetate and heptane (2:1 then 1:0) to afford 182 mg (83%) of the desired alcohol. (LC/MS 100% M+1 536).

Step 2

To a solution of alcohol (170 mg, 0.32 mmol) in 5 mL of dry dichloromethane was added a solution of Dess-Martin reagent (15% wt. Sol., 2 eq., 0.63 mmol, 1.80 g). The mixture was stirred at room temperature for 2 hours then quenched by adding a solution of $Na_2S_2O_3$ (4.0 eq., 1.28 mmol, 202.4 mg) in saturated sodium bicarbonate (30 mL) The aqueous layer was extracted twice with dichloromethane (20 mL). The organic layers were dried (MgSO$_4$) and concentrated in vacuum. The residue was purified over 12 g silica gel, eluting with a mixture of ethyl acetate and heptane (1.5:1 then 2:1) to afford morpholine-4-carboxylic acid {2-cyclopropylmethanesulfonyl-1-[1-(3-phenyl-1,2,4-oxadiazole-5-carbonyl)-propylcarbamoyl]-ethyl}-amide, a 3:1 mixture of diastereomers, (139 mg, 82%).

$^1$H NMR (CDCl$_3$): 8.15 (d, J=7.6 Hz, 2H), 8.0 (d, J=6.6 Hz, 1H, major), 7.9 (d, J=7 Hz, 1H minor), 7.6 (m, 3H), 6.08 (2×d, J=6.5 Hz, 1H), 5.4 (m, 1H), 4.95 (m, 1H), 3.8–3.69 (m, 5H), 3.53–3.35 (m, 5H), 3.15 (m, 2H), 2.2 (m, 1H), 1.95 (m, 1H), 1.2 (m, 1H), 1.06 (t, J=7.5 Hz, 3H), 0.8 (m, 2H), 0.5 (m, 2H). LC/MS shows 35% M+1 534 as well as 65% hydrate M+18 552.

Example 18

Morpholine-4-carboxylic acid {2-(2-methyl-propane-1-sulfonyl)-1-[1-(3-phenyl-1,2,4-oxadiazole-5-carbonyl)-propylcarbamoyl]-ethyl}-amide

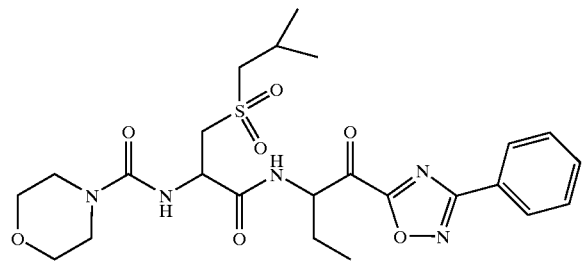

By proceeding in a similar manner to Example 17 above but using (R)-3-(2-methyl-propane-1-sulfonyl)-2-[(morpholine-4-carbonyl)-amino]-propionic acid (Reference Example 5) instead of (R)-3-cyclopropylmethanesulfonyl-2-[(morpholine-4-carbonyl)-amino]-propionic acid, in Step 1, there was prepared morpholine-4-carboxylic acid {2-(2-methyl-propane-1-sulfonyl)-1-[1-(3-phenyl-1,2,4-oxadiazole-5-carbonyl)-propylcarbamoyl]-ethyl}-amide. $^1$H NMR (CDCl$_3$): 8.15 (dd, 2H), 7.95–7.85 (2×d, 1H), 7.45 (m, 3H), 6.14–6.0 (2×d, 1H), 5.35 (m, 1H), 4.90 (m, 1H), 3.70 (m, 5H), 3.40 (m, 5H), 3.2–3.0 (m, 2H), 2.50–2.30 (m, 1H), 2.30–2.10 (m, 1H), 2.05–1.90 (m, 1H), 1.10 (t, 6H), 1.05 (t, 3H). MS: 536 (MH$^+$).

Example 19

Morpholine-4-carboxylic acid [1-[1-(3-ethyl-1,2,4-oxadiazole-5-carbonyl)-propylcarbamoyl]-2-(2-methyl-propane-1-sulfonyl)-ethyl]-amide

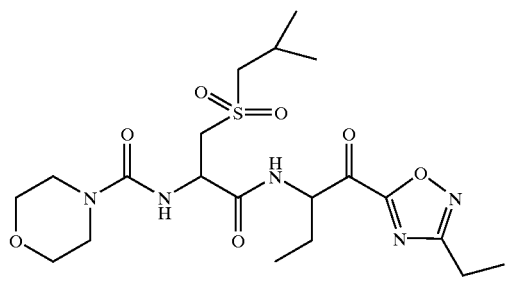

To a suspension of the (R)-3-(2-methyl-propane-1-sulfonyl)-2-[(morpholine-4-carbonyl)-amino]-propionic acid (113 mg, 0.35 mmol, Reference Example 5), (S)-2-amino-1-(3-ethyl-1,2,4-oxadiazol-5-yl)-butan-1-ol (0.35 mmol, 65 mg) and di-isopropylethylamine (1.2 eq., 0.073 mL) in dry dichloromethane (7 mL) was added PyBOP (1.1 eq., 200 mg). The mixture was stirred at room temperature overnight then quenched with NaHCO$_3$ solution. The volatiles were removed in vacuum, and the aqueous mixture was extracted in ethyl acetate. The organic layers were dried (Na$_2$SO$_4$) and then concentrated in vacuum. The residue was purified over silica gel, eluting with ethyl acetate: dichloromethane to afford the desired alcohol. To a solution of the alcohol in dry dichloromethane was added a solution of Dess-Martin reagent (15% wt. Sol., 2 eq.). The mixture was stirred at room temperature for 2 hours then quenched by adding a solution of Na$_2$S$_2$O$_3$ (4.0 eq.) in saturated sodium bicarbonate. The aqueous layer was extracted with dichloromethane. The organic layers were dried (MgSO$_4$) and concentrated in vacuo. The residue was purified over silica gel, eluted with a mixture of ethyl acetate and dichloromethane to afford morpholine-4-carboxylic acid [1-[1-(3-ethyl-1,2,4-oxadiazole-5-carbonyl)-propylcarbamoyl]-2-(2-methyl-propane-1-sulfonyl)-ethyl]-amide (98 mg, 57%).

$^1$H NMR (CDCl$_3$) 4:1 mixture of isomers 7.9 (d, J=6.4 Hz, 1H, major), 7.8 (d, J=6 Hz, 1H, minor), 6.1 (d, J=6.1 Hz, 1H, minor), 6.0 (d, J=6.1 Hz, 1H, major), 5.25 (m, 1H), 4.95 (m, 1H), 3.74–3.67 (m, 5H), 3.4 (m, 5H), 3.2 (m, 2H), 2.2 (m, 1H), 2.9 (q, J=7.5 Hz, 2H), 2.4 (m, 1H), 2.2 (m, 1H), 1.9 (m, 1H), 1.4 (t, J=7.6 Hz, 3H), 1.2 (d, J=6.6 Hz, 6H), 1.0 (t, J=7.4 Hz, 3H). LC/MS shows 52% M+1 588 as well as 37% hydrate M+18 506.

Example 20

Morpholine-4-carboxylic acid {2-phenylmethanesulfonyl-1-[1-(3-phenyl-[1,2,4]oxadiazole-5-carbonyl)-propylcarbamoyl]-ethyl}-amide

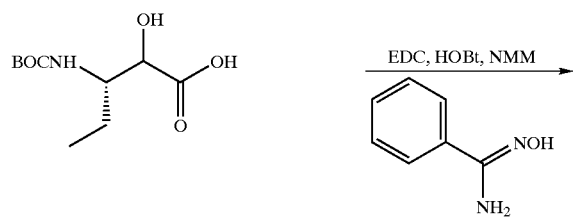 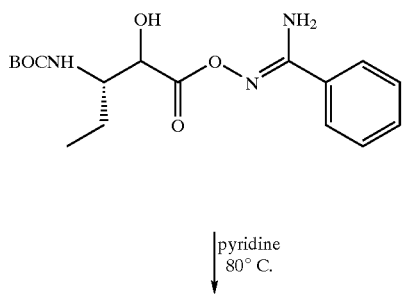

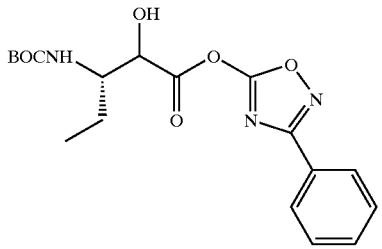

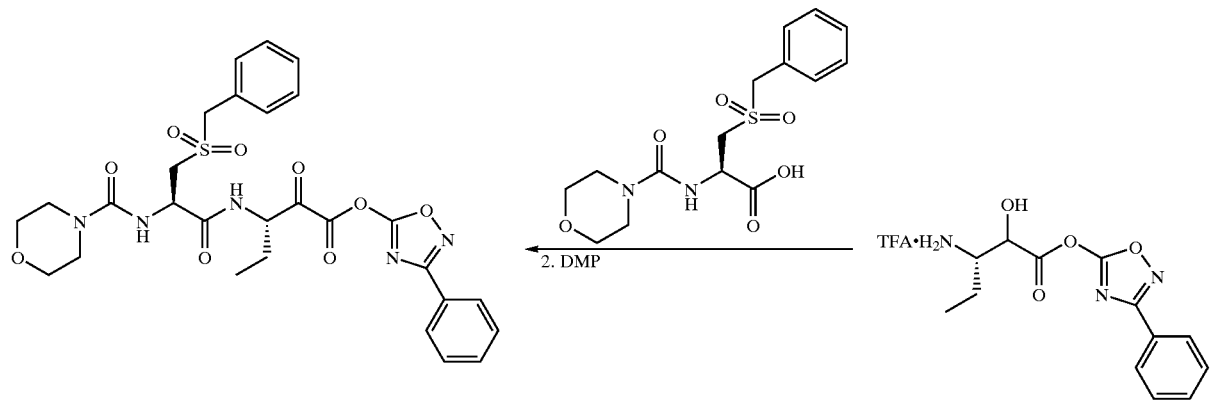

Step 1

3-tert-Butoxycarbonylamino-2-hydroxy-pentanoic acid (500 mg, 2.14 mmol) was combined with EDC (600 mg, 3.14 mmol), HOBt (600 mg, 3.92 mmol), and N-hydroxybenzamidine (292 mg, 2.14 mmol). Dichloromethane (10 mL) was added and then 4-methylmorpholine (1 mL). The mixture was stirred at ambient temperature for 16 hours. After dilution with ethyl acetate (200 mL), the solution was washed with water (30 mL), saturated aqueous NaHCO₃ solution and brine, then dried with MgSO₄ and then evaporated under vacuum.

Step 2

The product from step 1 was dissolved in pyridine (10 mL) and the solution was heated at 80° C. for 15 hours. The pyridine was evaporated under vacuum and the residue was subjected to flash chromatography on silica gel (eluent: ethyl acetate) to give {1-[hydroxy-(3-phenyl-[1,2,4]oxadiazol-5-yl)-methyl]-propyl}-carbamic acid tert-butyl ester (290 mg (0.83 mmol).

Step 3

{1-[Hydroxy-(3-phenyl-[1,2,4]oxadiazol-5-yl)-methyl]-propyl}-carbamic acid tert-butyl ester (145 mg, 0.41 mmol) was dissolved in CH₂Cl₂ (4 mL) and TFA (4 mL) was added. After stirring for 1 hour, the mixture was evaporated to dryness.

Step 4

2-[(Morpholine-4-carbonyl)-amino]-3-phenylmethanesulfonyl-propionic acid (200 mg, 0.56 mmol), EDC (200 mg, 1.05 mmol), HOBt (200 mg, 1.30 mmol) and CH₂Cl₂ (4 mL) were added to the product from step 3 above. 4-Methylmorpholine (0.5 mL) was added and the mixture was stirred at ambient temperature for 2 hours. After dilution with ethyl acetate (150 mL), the solution was washed with water (30 mL), saturated aqueous NaHCO₃ solution and brine, then dried with MgSO₄ and then evaporated under vacuum. The residue was dissolved in dry dichloromethane (10 mL) and Dess-Martin periodinane (500 mg, 1.2 mmol) was added. After stirring at ambient temperature for 1 hour the mixture was diluted with ethyl acetate (150 mL) and the mixture was treated with 0.26M Na₂S₂O₃ solution in saturated aqueous NaHCO₃. The organic phase was washed with saturated aqueous NaHCO₃ and brine, then dried with MgSO₄ and then evaporated. The residue was subjected to flash chromatography on silica gel (hexane/ethyl acetate 1:2 to ethyl acetate) to give morpholine-4-carboxylic acid {2-phenylmethanesulfonyl-1-[1-(3-phenyl-[1,2,4]oxadiazole-5-carbonyl)-propylcarbamoyl]-ethyl}-amide (40 mg, 0.07 mmol). ¹H NMR (DMSO): 8.79 (d, J=6 Hz, 1H), 8.04 (d, J=8 Hz, 2H), 7.65–7.53 (m, 3H), 7.41–7.32 (m, 5H), 7.02 (d, J=8 Hz, 1H), 4.96–4.90 (m, 1H), 4.73–4.66 (m, 1H), 4.45 (s, 2H), 3.57–3.19 (m, 10H), 2.04–1.95 (m, 1H), 1.80–1.71 (m, 1H), 0.95 (t, J=7.6 Hz, 3H). MS: (M⁺+1) 570.

Example 21

Moripholine-4-carboxylic acid {1-[1-(3-ethyl-[1,2,4]oxadiazole-5-carbonyl)-propylcarbamoyl]-2-phenylmethanesulfonyl-ethyl}-amide

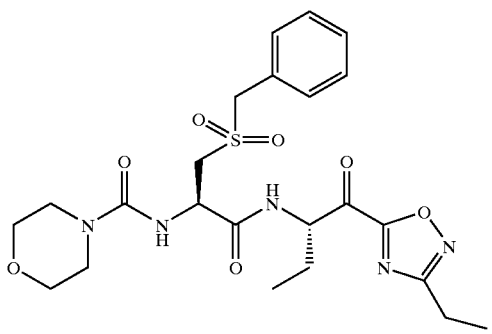

By proceeding in a similar manner to that described in Example 20 above but using N-hydroxy-propionamidine instead of N-hydroxy-benzamidine in step 1, there was prepared morpholine-4-carboxylic acid {1-[1-(3-ethyl-[1,2,4]oxadiazole-5-carbonyl)-propylcarbamoyl]-2-phenylmethanesulfonyl-ethyl}-amide. $^1$H NMR (DMSO): 8.73 (d, J=6.4 Hz, 1H), 7.40–7.33 (m, 5H), 7.01 (d, J=8 Hz, 1H), 4.88–4.82 (m, 1H), 4.71–4.65 (m, 1H), 4.47 (s, 2H), 3.57–3.24 (m, 10H), 2.81 (q, J=7.6 Hz, 2H), 1.99–1.88 (m, 1H), 1.75–1.64 (m, 1H), 1.26 (t, J=7.6 Hz, 3H), 0.92 (t, J=7.6 Hz, 3H). MS: (M++1) 522.

Example 22

Morpholine-4-carboxylic acid {1-[1-(5-ethyl-[1,3,4]oxadiazole-2-carbonyl)-propylcarbamoyl]-2-phenylmethanesulfonyl-ethyl}-amide

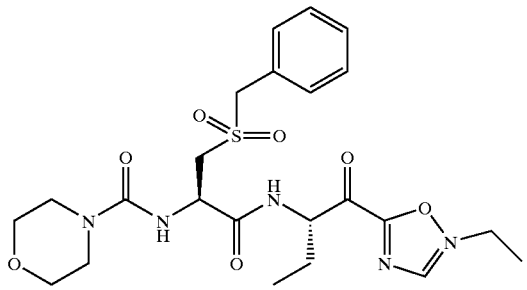

By proceeding in a similar manner to that described in Example 1 there was prepared morpholine-4-carboxylic acid {1-[1-(5-ethyl-[1,3,4]oxadiazole-2-carbonyl)-propylcarbamoyl]-2-phenylmethanesulfonyl-ethyl}-amide. $^1$H NMR (DMSO): 8.64 (d, J=6.8 Hz, 1H), 7.42–7.32 (m, 5H), 7.02 (d, J=8.8 Hz, 1H), 5.04–4.96 (m, 1H), 4.62–4.72 (m, 1H), 4.47 (s, 2H), 3.64–3.24 (m, 10H), 2.96 (q, J=7.6 Hz, 2H), 1.89–1.79 (m, 1H), 1.72–1.60 (m, 1H), 1.38–1.16 (m, 2H), 1.29 (t, J=7.6 Hz, 3H), 0.89 (t, J=7.2 Hz, 3H). MS: (M$^+$+1) 536.

Example 23

Morpholine-4-carboxylic acid {1-[1-(5-tert-butyl-[1,3,4]oxadiazole-2-carbonyl)-propylcarbamoyl]-2-phenylmethanesulfonyl-ethyl}-amide

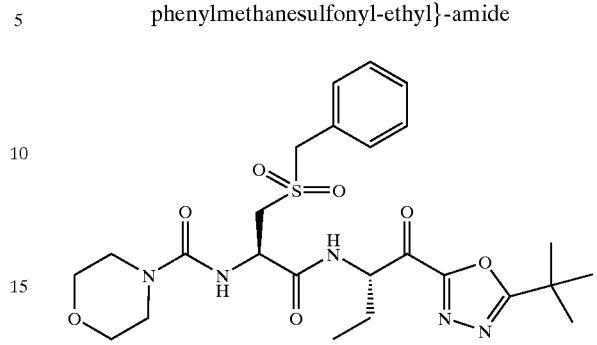

By proceeding in a similar manner to that described in Example 1 there was prepared morpholine-4-carboxylic acid {1-[1-(5-tert-butyl-[1,3,4]oxadiazole-2-carbonyl)-propylcarbamoyl]-2-phenylmethanesulfonyl-ethyl}-amide. $^1$H NMR (DMSO): 8.63 (d, J=5.2 Hz, 1H), 7.26–7.46 (m, 5H), 7.02 (d, J=8.8 Hz, 1H), 4.98–5.08 (m, 1H), 4.62–4.72 (m, 1H), 4.48 (s, 2H), 3.24–3.64 (m, 10H), 1.76–1.92 (m, 1H), 1.58–1.74 (m, 1H), 1.39 (s, 9H), 1.16–1.38 (m, 2H), 0.89 (t, J=7.6 Hz, 3H). MS: (M$^+$+1) 564.

Example 24

Morpholine-4-carboxylic acid {2-(2-difluoromethoxy-phenylmethanesulfonyl)-1-[1,1-dimethyl-2-oxo-2-(5-pyridin-3-yl-[1,3,4]oxadiazol-2-yl)-ethylcarbamoyl]-ethyl}-amide

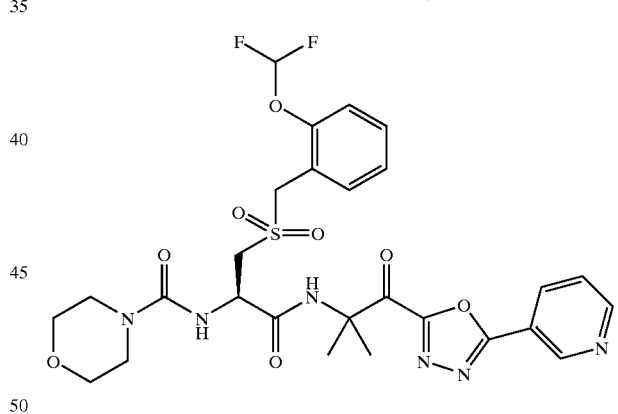

By proceeding in a similar manner to that described in Example 2 there was prepared $^1$H NMR (DMSO-d): 9.33(1H, s, NH), 9.22(1H, dd, J=1.74 Hz), 8.84(1H, dd), 8.43(1H, d, t)7.68(1H, dd, J=1.75 Hz, J=6.7 Hz), 7.42(2H, m), 7.3–7.2(2H, m), 7.07(1H, t, J=74.1 Hz), 6.76(1H, d, J=8.6 Hz, NH), 4.7–4.6(1H, m), 4.45(2H, s), 3.5–3.4(4H, m), 3.38–3.2(2H, m), 3.2–3.1(4H, m), 1.52(6H, s). MS: 635.6(M−1), 637.4(M+1).

Example 25

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM). Human cathepsin S (0.158 pMoles in 25 μL of assay buffer) was added to the dilutions. The assay solutions were mixed for 5–10 seconds on a shaker plate, covered and incubated for 30 minutes at ambient temperature. Z-Val-Val-Arg-AMC (9 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Example 26

Cathepsin B Assay

Solutions of test compounds in varying concentrations were prepared in 10 μL of dimethyl sulfoxide (DMSO) and then diluted into assay buffer (40 μL, comprising: N,N-bis (2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5–10 seconds on a shaker plate, covered and incubated for 30 minutes at ambient temperature. Z-FR-AMC (20 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Example 27

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5–10 seconds on a shaker plate, covered and incubated for 30 minutes at ambient temperature. Z-Phe-Arg-AMC (4 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Example 28

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5–10 seconds on a shaker plate, covered and incubated for 30 minutes at ambient temperature. Z-Phe-Arg-AMC (1 nMoles in 25 μL of assay buffer) was added to the assay solutions and hydrolysis was followed spectrophotometrically at (λ 460 nm) for 5 minutes. Apparent inhibition constants ($K_i$) were calculated from the enzyme progress curves using standard mathematical models.

Compounds of the invention were tested according to the above-described assays for protease inhibition and observed to exhibit selective cathepsin S inhibitory activity. For example, the compounds of the invention were found to inhibit cathepsin S protease activity at concentrations that are least 50 fold less than those concentrations required to produce an equiactive inhibition of cathepsin K protease activity. The apparent inhibition constants ($K_i$) for compounds of the invention, against Cathepsin S, were in the range from about $10^{-10}$M to about $10^{-7}$M.

Example 29

Representative Pharmaceutical Formulations Containing a Compound of Formula I

| ORAL FORMULATION | |
|---|---|
| Compound of Formula I | 10–100 mg |
| Citric Acid Monohydrate | 105 mg |
| Sodium Hydroxide | 18 mg |
| Flavoring | |
| Water | q.s. to 100 mL |
| INTRAVENOUS FORMULATION | |
| Compound of Formula I | 0.1–10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| Compound of Formula I | 1% |
| Microcrystalline Cellulose | 73% |
| Stearic Acid | 25% |
| Colloidal Silica | 1%. |

We claim:
1. A compound of Formula (I):

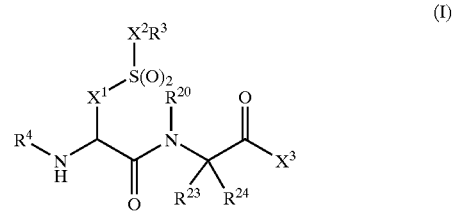

wherein:
$X^1$ and $X^2$ are both methylene or $X^1$ is ethylene and $X^2$ is methylene or a bond;
$R^3$ is —CR$^5$=CHR$^6$, —CR$^5$(CR$^6{}_3$)$_2$, or (C$_{3-12}$) cycloalkyl, wherein $R^5$ and $R^6$ are independently hydrogen or (C$_{1-4}$)alkyl or $R^5$ and $R^6$ together with the atoms to which $R^5$ and $R^6$ are attached form (C$_{3-12}$) cycloalkyl, (C$_{6-12}$)aryl, or (C$_{9-12}$)bicycloaryl and $R^3$ optionally is substituted by 1 to 5 radicals independently selected from a group consisting of (C$_{1-4}$)alkyl, cyano, halo, halo-substituted (C$_{1-4}$)alkyl, nitro, —X$^4$NR$^9$R$^9$, —X$^4$OR$^9$, —X$^4$SR$^9$, —X$^4$C(O)NR$^9$R$^9$, —X$^4$C(O)OR$^9$, —X$^4$S(O)R$^{10}$, —X$^4$S(O)$_2$R$^{10}$ and —X$^4$C(O)R$^{10}$, wherein $X^4$ is a bond or (C$_{1-2}$)alkylene, $R^9$ at each occurrence independently is hydrogen, (C$_{1-3}$)alkyl or halo-substituted (C$_{1-3}$)alkyl and $R^{10}$ is (C$_{1-3}$)alkyl or halo-substituted (C$_{1-3}$)alkyl; and
$R^4$ is morpholine-4-carbonyl, —C(O)X$^5$R$^{11}$ or —S(O)$_2$ X$^5$R$^{11}$, wherein X$^5$ is a bond, —O— or —NR$^{12}$—, wherein R$^{12}$ is hydrogen or (C$_{1-6}$)alkyl, and R$^{11}$ is (i) (C$_{1-6}$)alkyl optionally substituted by —OR$^{13}$, —SR$^{13}$, —S(O)R$^{13}$, —S(O)$_2$R$^{13}$, —C(O)R$^{13}$, —C(O)OR$^{13}$, —C(O)NR$^{13}$R$^{14}$, —NR$^{13}$R$^{14}$, —NR$^{14}$C(O)R$^{13}$, —NR$^{14}$C(O)OR$^{13}$, —NR$^{14}$C(O)NR$^{13}$R$^{14}$ or —NR$^{14}$C(NR$^{14}$)NR$^{13}$R$^{14}$, wherein R$^{13}$ is (C$_{3-12}$)cycloalkyl(C$_{0-3}$)alkyl, (C$_{6-12}$)aryl(C$_{0-3}$)alkyl, (C$_{9-12}$)bicycloaryl(C$_{0-3}$)alkyl or and R$^{14}$ at each occurrence independently is hydrogen or (C$_{1-6}$)alkyl, or (ii) (C$_{3-12}$)cycloalkyl(C$_{0-3}$)alkyl, (C$_{6-12}$)aryl(C$_{0-3}$)alkyl, or (C$_{9-12}$)bicycloaryl(C$_{0-3}$)alkyl or (iii) (C$_{3-6}$)cycloalkyl (C$_{0-3}$)alkyl, or phenyl(C$_{0-3}$)alkyl substituted by —X$^6$OR$^{15}$, —X$^6$SR$^{15}$, —X$^6$S(O)R$^{15}$, —X$^6$S(O)$_2$R$^{15}$, —X$^6$C(O)R$^{15}$, —X$^6$C(O)OR$^{15}$, —X$^6$C(O)NR$^{15}$R$^{16}$, —X$^6$NR$^{15}$R$^{16}$, —X$^6$NR$^{16}$C(O)R$^{15}$, —X$^6$NR$^{16}$C(O)OR$^{15}$, —X$^6$NR$^{16}$C(O)NR$^{15}$R$^{16}$, —X$^6$NR$^{16}$C(O)OR$^{16}$, —X$^6$NR$^{16}$C(NR$^{16}$)NR$^{15}$R$^{16}$, wherein X$^6$ is a bond or methylene, R$^{15}$ is (C$_{3-6}$)cycloalkyl(C$_{0-3}$)alkyl, or phenyl(C$_{0-3}$)alkyl and R$^{16}$ is hydrogen or (C$_{1-6}$)alkyl; and R$^4$ optionally further contains 1 to 5 substituents which when occurring within an alicyclic or aromatic ring system are radicals independently selected from a group consisting of (C$_{1-6}$)alkyl, (C$_{1-6}$)alkylidene, cyano, halo, nitro, halo-substituted (C$_{1-3}$)alkyl, —X$^6$NR$^{17}$R$^{17}$, —X$^6$NR$^{17}$C(O)OR$^{17}$, —X$^6$NR$^{17}$C(O)NR$^{17}$R$^{17}$, —X$^6$NR$^{17}$C(NR$^{17}$)NR$^{17}$R$^{17}$, —X$^6$OR$^{17}$, —X$^6$SR$^{17}$, —X$^6$C(O)OR$^{17}$, —X$^6$C(O)NR$^{17}$R$^{17}$, —X$^6$S(O)$_2$NR$^{17}$R$^{17}$, —X$^6$P(O)(OR$^{18}$)OR$^{17}$, —X$^6$OP(O)(OR$^{18}$)OR$^{17}$, —X$^6$NR$^{17}$C(O)R$^{18}$, —X$^6$S(O)R$^{18}$, —X$^6$S(O)$_2$R$^{18}$ and —X$^6$C(O)R$^{18}$ and when occurring within an aliphatic moiety are radicals independently selected from a group consisting of cyano, halo, nitro, —NR$^{17}$R$^{17}$, —NR$^{17}$C(O)OR$^{17}$, —NR$^{17}$C(O)NR$^{17}$R$^{17}$, —NR$^{17}$C(NR$^{17}$)NR$^{17}$R$^{17}$, —OR$^{17}$, —SR$^{17}$, —C(O)OR$^{17}$, —C(O)NR$^{17}$R$^{17}$, —S(O)$_2$NR$^{17}$R$^{17}$, —P(O)(OR$^{17}$)OR$^{17}$, —OP(O)(OR$^{17}$)OR$^{17}$, —NR$^{17}$C(O)R$^{18}$, —S(O)R$^{18}$, —S(O)$_2$R$^{18}$ and —C(O)R$^{18}$, wherein X$^6$ is a bond or (C$_{1-6}$)alkylene, R$^{17}$ at each occurrence independently is hydrogen, (C$_{1-6}$)alkyl or halo-substituted (C$_{1-3}$)alkyl and R$^{18}$ is (C$_{1-6}$)alkyl or halo-substituted (C$_{1-3}$)alkyl;

R$^{20}$ is selected from the group consisting of hydrogen, (C$_{1-6}$)alkyl, (C$_{3-12}$)cycloalkyl(C$_{0-6}$)alkyl, and (C$_{6-12}$)aryl(C$_{0-6}$)alkyl;

R$^{23}$ is selected from the group consisting of hydrogen, (C$_{1-6}$)alkyl, alkoxy(C$_{1-3}$)alkyl, halo(C$_{1-3}$)alkyl, (C$_{3-12}$)cycloalkyl(C$_{0-6}$)alkyl, and (C$_{6-12}$)aryl(C$_{0-6}$)alkyl; and R$^{23}$ optionally substituted with amino, —NHC(O)R$^{15}$ or —R$^{15}$ wherein R$^{15}$ is as described above; and R$^{24}$ is selected from hydrogen or (C$_{1-6}$)alkyl; or R$^{23}$ and R$^{24}$ taken together with the carbon atom to which both R$^{23}$ and R$^{24}$ are attached form (C$_{3-8}$)cycloalkylene or (C$_{3-8}$)heterocycloalkylene;

X$^3$ is selected from group (a), (b) or (c);

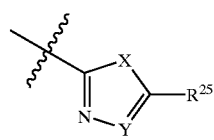
(a)

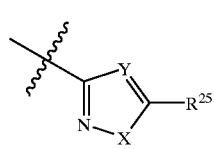
(b)

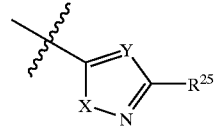
(c)

wherein X is O and Y is N;

R$^{25}$ is selected from hydrogen, (C$_{1-6}$)alkyl, (C$_{3-12}$)cycloalkyl(C$_{0-6}$)alkyl, hetero(C$_{3-12}$)cycloalkyl(C$_{0-6}$)alkyl, (C$_{6-12}$)aryl(C$_{0-6}$)alkyl, hetero(C$_{5-13}$)aryl(C$_{0-6}$)alkyl with one hetero atom, —X$^4$NHR$^{15}$, —X$^4$S(O)$_2$R$^{26}$ or —X$^4$C(O)R$^{17}$NR$^{17}$C(O)R$^{17}$ wherein R$^{15}$, R$^{17}$ and X$^4$ are as described above;

R$^{26}$ is selected from the group consisting of hydrogen, (C$_{1-6}$)alkyl, (C$_{3-12}$)cycloalkyl(C$_{0-6}$)alkyl, hetero(C$_{5-12}$)cycloalkyl(C$_{0-6}$)alkyl, (C$_{6-12}$)aryl(C$_{0-6}$)alkyl, hetero(C$_{5-12}$)aryl(C$_{0-6}$)alkyl, with one hetero atom, (C$_{9-12}$)bicycloaryl(C$_{0-3}$)alkyl and hetero(C$_{8-12}$)-bicycloaryl(C$_{0-3}$)alkyl;

wherein R$^{25}$ optionally further contains 1 to 5 substituents which when occurring within an alicyclic or aromatic ring system are radicals independently selected from a group consisting of (C$_{1-6}$)alkyl, (C$_{1-6}$)alkylidene, cyano, halo, nitro, halo-substituted (C$_{1-3}$)alkyl, —X$^6$NR$^{17}$R$^{17}$, —X$^6$NR$^{17}$C(O)OR$^{17}$, —X$^6$NR$^{17}$C(O)NR$^{17}$R$^{17}$, —X$^6$NR$^{17}$C(NR$^{17}$)NR$^{17}$R$^{17}$, —X$^6$OR$^{17}$, —X$^6$C(O)R$^{17}$, —X$^6$OR$^{15}$, —X$^6$SR$^{17}$, —X$^6$C(O)OR$^{17}$, —X$^6$C(O)NR$^{17}$R$^{17}$, —X$^6$S(O)$_2$NR$^{17}$R$^{17}$, —X$^6$P(O)(OR$^{8}$)OR$^{17}$, —X$^6$OP(O)(OR$^{8}$)OR$^{17}$, —X$^6$NR$^{17}$C(O)R$^{18}$, —X$^6$S(O)R$^{18}$, —X$^6$S(O)$_2$R$^{18}$ and —X$^6$C(O)R$^{18}$ and when occurring within an aliphatic moiety are radicals independently selected from a group consisting of cyano, halo, nitro, —NR$^{17}$R$^{17}$, —NR$^{17}$C(O)OR$^{17}$, —NR$^{17}$C(O)NR$^{17}$R$^{17}$, —NR$^{17}$C(NR$^{17}$)NR$^{17}$R$^{17}$, —OR$^{17}$, —SR$^{17}$, —C(O)OR$^{17}$, —C(O)NR$^{17}$R$^{17}$, —S(O)$_2$NR$^{17}$R$^{17}$, —P(O)(OR$^{17}$)OR$^{17}$, —OP(O)(OR$^{17}$)OR$^{17}$, —NR$^{17}$C(O)R$^{18}$, —S(O)R$^{18}$, —S(O)$_2$R$^{18}$ and —C(O)R$^{18}$, wherein R$^{15}$, R$^{17}$, R$^{18}$ and X$^6$ are as described above; or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative.

2. A compound of claim 1 wherein:

X$^1$ and X$^2$ are both methylene or X$^1$ is ethylene and X$^2$ is a bond;

R$^3$ is —CR$^5$═CHR$^6$, —CR$^5$(CR$^6$$_3$)$_2$, or (C$_{3-12}$)cycloalkyl, wherein R$^5$ and R$^6$ are independently hydrogen or (C$_{1-4}$)alkyl or R$^5$ and R$^6$ together with the atoms to which R$^5$ and R$^6$ are attached form (C$_{3-12}$)cycloalkyl, (C$_{6-12}$)aryl, or (C$_{9-12}$)bicycloaryl;

wherein within R$^3$ any cycloalkyl, aryl, or bicycloaryl group may be substituted with 1 to 5 radicals independently selected from a group consisting of (C$_{1-4}$)alkyl, cyano, halo, halo-substituted (C$_{1-4}$)alkyl, —X$^4$OR$^9$ and —X$^4$C(O)OR$^9$, wherein X$^4$ is a bond or (C$_{1-2}$)alkylene and R$^9$ at each occurrence independently is (C$_{1-3}$)alkyl and halo-substituted (C$_{1-3}$)alkyl;

R$^4$ is morpholine-4-carboxyl, —C(O)X$^5$R$^{11}$ or —S(O)$_2$X$^5$R$^{11}$, wherein X$^5$ is a bond, —O— or —NR$^{12}$—, wherein R$^{12}$ is hydrogen or (C$_{1-6}$)alkyl, and R$^{11}$ is (i) (C$_{1-6}$)alkyl or (ii) (C$_{6-12}$)aryl(C$_{0-3}$)alkyl, or (C$_{9-12}$)bicycloaryl(C$_{0-3}$)alkyl (iii) phenyl(C$_{0-3}$)alkyl substituted by —X⁶OR¹⁵, —X⁶C(O)R¹⁵ or —X⁶NR¹⁶C(O) OR¹⁶, wherein X⁶ is a bond or methylene, R¹⁵ is phenyl(C₀₋₃)alkyl and R¹⁶ is hydrogen or (C₁₋₆)alkyl; wherein within R⁴ any alicyclic or aromatic ring system may be substituted with 1 to 5 radicals independently selected from a group consisting of (C₁₋₆)alkyl, halo, —X⁶NR¹⁷R¹⁷, —X⁶OR¹⁷, —X⁶C(O)OR¹⁷, —X⁶NC(O)R¹⁶ and —X⁶C(O)R¹⁸, wherein R¹⁷ at each occurrence independently is hydrogen, (C₁₋₆)alkyl or halo-substituted (C₁₋₃)alkyl and R¹⁸ is (C₁₋₆)alkyl or halo-substituted (C₁₋₃)alkyl;

R²⁰ is hydrogen or(C₁₋₆)alkyl;

R²³ is (C₁₋₆)alkyl or (C₆₋₁₂)aryl(C₀₋₆)alkyl;

R²⁴ is hydrogen or (C₁₋₆)alkyl;

X³ is

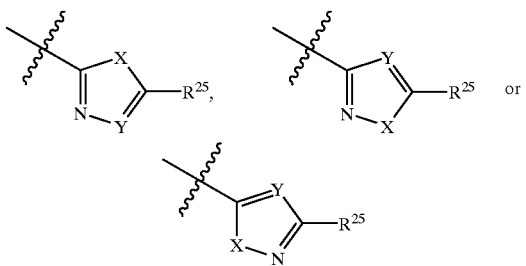

wherein X is O, Y is N and R²⁵ is selected from hydrogen, halo(C₁₋₃)alkyl, (C₁₋₆)alkyl, (C₃₋₁₂)cycloalkyl(C₀₋₆)alkyl, (C₆₋₁₂)aryl(C₀₋₆)alkyl or hetero (C₅₋₁₃)aryl(C₀₋₆)alkyl with one hetero atom, wherein within R²⁵ any alicyclic or aromatic ring system may be substituted with 1 to 5 radicals independently selected from (C₁₋₆)alkyl and halo-substituted (C₁₋₃) alkyl; or a derivative of said compound selected from the group comprising N-oxide derivatives, prodrug derivatives, protected derivatives, isomers, and mixtures of isomers of said compound; or a pharmaceutically acceptable salt or solvate of said compound or said derivative.

3. A compound of claim 2 wherein R³ is selected from the group consisting of phenyl, pyridin-2-yl, pyridin-3-yl, pyridin-4-yl, vinyl, 2-difluoromethoxyphenyl, 1-oxy-pyridin-2-yl, 4-methoxyphenyl, 4-methylphenyl, 2-methylphenyl, 4-chlorophenyl, 3,5-dimethylphenyl, 4-trifluoromethylphenyl, 4-trifluoromethoxyphenyl, 2-bromophenyl, naphthalen-2-yl, 3,4-dichlorophenyl, 3-methylphenyl, 3-trifluoromethylphenyl, 3-trifluoromethoxyphenyl, 2,3,4,5,6-pentafluoro-phenyl, 2-fluorophenyl, 2-chlorophenyl, 2-cyano-phenyl, 2-trifluoromethylphenyl, 4-tert-butyl-phenyl, 3-chlorophenyl, 4-bromophenyl, 2-fluoro-3-chloro-phenyl, 2-fluoro-3-methyl-phenyl, 3-fluorophenyl, 2,5-difluorophenyl, 3-bromophenyl, 2,5-dichlorophenyl, 2,6-difluorophenyl, 3-cyano-phenyl, 4-cyano-phenyl, 2-trifluoromethoxyphenyl, 2,3-difluorophenyl, biphenyl, 2-bromo-5-fluoro-phenyl, 4-fluorophenyl, 3,4-difluorophenyl, 2,4-difluorophenyl, 2,4,6-trifluorophenyl, 2,4,5-trifluorophenyl, 2,3,4-trifluorophenyl, 2-chloro-5-trifluoromethylphenyl, 2,4-bis-trifluoromethylphenyl, 2,5,6-trifluorophenyl, 2-fluoro-3-trifluoromethylphenyl, 2-fluoro-4-trifluoromethylphenyl, 2-fluoro-5-trifluoromethylphenyl, 2,3,5-trifluorophenyl, 2-fluoro-5-trifluoromethylphenyl, 5-fluoro-2-trifluoromethylphenyl, 4-fluoro-3-trifluoromethylphenyl, 2-methoxyphenyl, 3,5-bis-trifluoromethylphenyl, 4-difluoromethoxyphenyl, 3-difluoromethoxyphenyl, 2,6-dichlorophenyl, 4-carboxyphenyl, cyclohexyl, cyclopropyl, isopropyl, thiophen-2-yl, 5-chloro-thiophen-2-yl and 3,5-dimethyl-isoxazol-4-yl; or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative.

4. A compound of claim 3 wherein R⁴ is benzoyl, morpholine-4-carbonyl, acetyl, 2-methoxy-benzoyl, 3-methoxy-benzoyl, naphthalene-2-carbonyl, benzo[1,3]dioxole-5-carbonyl, tert-butoxy-carbonyl, biphenyl-4-carbonyl, 3-acetyl-benzoyl, 4-phenoxy-benzoyl, 3-hydroxy-benzoyl, 4-hydroxy-benzoyl, 3-(tert-butoxycarbonylamino-methyl)-benzoyl, 4-benzoyl-benzoyl, 4-chloro-benzoyl, 3-flouro-4-methoxy-benzoyl, 4-methoxy-benzoyl, 4-triflouromethoxy-benzoyl, 3,4-diflouro-benzoyl, 4-fluoro-benzoyl, 3,4-dimethoxy-benzoyl, 3-methyl-benzoyl, 4-bromo-benzoyl, 4-triflouromethyl-benzoyl, 3-benzoyl-benzoyl, cyclopentane-carbonyl, benzenesulfonyl, naphthalene-2-sulfonyl, formamyl-methyl ester, 4-methyl-pentanoyl, formamyl-isobutyl ester, formamyl-monoallyl ester, formamyl-isopropyl ester, N,N-dimethyl-formamyl, N-isopropyl-formamyl, 3-phenyl-acryloyl, and 3-phenoxy-benzoyl; or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative.

5. A compound of claim 4 wherein R²⁵ is tert-butyl, cyclopropyl, ethyl, phenyl, pyridinyl, or trifluoromethyl; or a derivative of said compound selected from the group consisting of N-oxide derivatives, prodrug derivatives, protected derivatives, isomers, and mixtures of isomers of said compound; or a pharmaceutically acceptable salt or solvate of said compound or said derivative.

6. A compound of claim 2, wherein R³ is —CR⁵=CHR⁶ wherein R⁵ and R⁶ together with the atoms to which R⁵ and R⁶ are attached form (C₆₋₁₂)aryl, optionally substituted by 1 to 5 radicals independently selected from a group consisting of (C₁₋₄)alkyl, cyano, halo, halo-substituted (C₁₋₄)alkyl, —X⁴OR⁹ and —X⁴C(O)OR⁹, wherein X⁴ is a bond or (C₁₋₁₂)alkylene, R⁹ at each occurrence independently is (C₁₋₃)alkyl or halo-substituted (C₁₋₃)alkyl.

7. A compound of claim 6 wherein R³ is phenyl or 2-difluoromethoxyphenyl.

8. A compound of claim 2 wherein R³ is —CR⁵(CR⁶₃)₂ wherein R⁵ is hydrogen and R⁶ is (C₁₋₄)alkyl.

9. A compound of claim 8 wherein R³ is —CH(CH₃)₂.

10. A compound of claim 2 wherein R³ is (C₃₋₁₂) cycloalkyl.

11. A compound of claim 10 wherein R³ is cyclopropyl.

12. A compound of claim 5, wherein X³ is

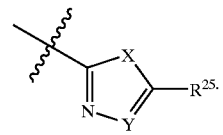

13. A compound of claim 5, wherein $X^3$ is

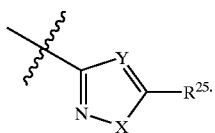

14. A compound of claim 5, wherein X3

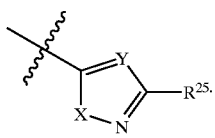

15. The compound of claim 2 wherein $R^4$ is —C(O)$X^5R^{11}$ wherein $X^5$ is a bond.

16. The compound of claim 2 wherein $R^4$ is

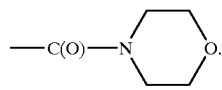

17. The compound of claim 2 wherein $R^{20}$ is hydrogen, $R^{23}$ is $(C_{1-6})$alkyl, $R^{24}$ is hydrogen, $R^{25}$ is tert-butyl, cyclopropyl, ethyl, phenyl, pyridin-3-yl, pyridin-4-yl, thien-3-yl or trifluoromethyl.

18. The compound of claim 1 selected from the group consisting of:
  morpholine-4-carboxylic acid {2-(2-difluoromethoxy-phenylmethanesulfonyl)-1-[1,1-dimethyl-2-oxo-2-(5-pyridin-3-yl-[1,3,4]oxadiazol-2-yl)-ethylcarbamoyl]-ethyl}-amide;
  morpholine-4-carboxylic acid {2-phenylmethanesulfonyl-1-[1-(5-phenyl-[1,3,4]oxadiazole-2-carbonyl)-pentylcarbamoyl]-ethyl}-amide;
  morpholine-4-carboxylic acid {2-(2-difluoromethoxy-phenylmethanesulfonyl)-1-[1-(5-pyridin-3-yl-[1,3,4]oxadiazole-2-carbonyl)-pentylcarbamoyl]-ethyl}-amide;
  morpholine-4-carboxylic acid [1-[1-(3-cyclopropyl-1,2,4-oxadiazole-5-carbonyl)-propylcarbamoyl]-2-(2-methyl-propane-1-sulfonyl)-ethyl]-amide;
  morpholine-4-carboxylic acid {2-(2-methyl-propane-1-sulfonyl)-1-[1-(3-thiophen-2-yl-1,2,4-oxadiazole-5-carbonyl)-propylcarbamoyl]-ethyl}-amide;
  morpholine-4-carboxylic acid [1-[1-(3-tert-butyl-1,2,4-oxadiazole-5-carbonyl)-propylcarbamoyl]-2-(2-methyl-propane-1-sulfonyl)-ethyl]-amide;
  morpholine-4-carboxylic acid {2-cyclopropylmethanesulfonyl-1-[1-(5-phenyl-1,2,4-oxadiazole-3-carbonyl)-propylcarbamoyl]-ethyl}-amide;
  morpholine-4-carboxylic acid {(R)-2-cyclopropylmethanesulfonyl-1-[(S)-1-(5-trifluoromethyl-1,2,4-oxadiazole-3-carbonyl)-propylcarbamoyl]-ethyl}-amide;
  morpholine-4-carboxylic acid [(1-[(1-(5-ethyl-1,2,4-oxadiazole-3-carbonyl)-propylcarbamoyl]-2-(2-methyl-propane-1-sulfonyl)-ethyl]-amide;
  {(R)-2-(2-methyl-propane-1-sulfonyl)-1-[(S)-1-(5-thiophen-3-yl-1,2,4-oxadiazole-3-carbonyl)-propylcarbamoyl]-ethyl}-amide;
  morpholine-4-carboxylic acid {(R)-1-[(S)-1-(3-tert-butyl-1,2,4-oxadiazole-5-carbonyl)-propylcarbamoyl]-2-cyclopropylmethanesulfonyl-ethyl}-amide;
  morpholine-4-carboxylic acid {(R)-2-(2-methyl-propane-1-sulfonyl)-1-[(S)-1-(5-trifluoromethyl-1,2,4-oxadiazole-3-carbonyl)-propylcarbamoyl]-ethyl}-amide;
  morpholine-4-carboxylic acid {(R)-1-[(S)-1-(5-tert-butyl-1,2,4-oxadiazole-3-carbonyl)-propylcarbamoyl]-2-phenylmethanesulfonyl-ethyl}-amide;
  morpholine-4-carboxylic acid {(R)-1-[(S)-1-(5-tert-butyl-1,2,4-oxadiazole-3-carbonyl)-propylcarbamoyl]-2-phenylmethanesulfonyl-ethyl}-amide;
  morpholine-4-carboxylic acid {2-cyclopropylmethanesulfonyl-1-[1-(3-cyclopropyl-1,2,4-oxadiazole-5-carbonyl)-propylcarbamoyl]-ethyl}-amide;
  morpholine-4-carboxylic acid {2-cyclopropylmethanesulfonyl-1-[1-(3-ethyl-1,2,4-oxadiazole-5-carbonyl)-propylcarbamoyl]-ethyl}-amide;
  morpholine-4-carboxylic acid {2-cyclopropylmethanesulfonyl-1-[1-(3-phenyl-1,2,4-oxadiazole-5-carbonyl)-propylcarbamoyl]-ethyl}-amide;
  morpholine-4-carboxylic acid {2-(2-methyl-propane-1-sulfonyl)-1-[1-(3-phenyl-1,2,4-oxadiazole-5-carbonyl)-propylcarbamoyl]-ethyl}-amide;
  morpholine-4-carboxylic acid [1-[1-(3-ethyl-1,2,4-oxadiazole-5-carbonyl)-propylcarbamoyl]-2-(2-methyl-propane-1-sulfonyl)-ethyl]-amide;
  morpholine-4-carboxylic acid {2-phenylmethanesulfonyl-1-[1-(3-phenyl-[1,2,4]oxadiazole-5-carbonyl)-propylcarbamoyl]-ethyl}-amide;
  morpholine-4-carboxylic acid {1-[1-(3-ethyl-[1,2,4]oxadiazole-5-carbonyl)-propylcarbamoyl]-2-phenylmethanesulfonyl-ethyl}-amide;
  morpholine-4-carboxylic acid {1-[1-(5-ethyl-[1,3,4]oxadiazole-2-carbonyl)-propylcarbamoyl]-2-phenylmethanesulfonyl-ethyl}-amide;
  morpholine-4-carboxylic acid {1-[1-(5-tert-butyl-[1,3,4]oxadiazole-2-carbonyl)-propylcarbamoyl]-2-phenylmethanesulfonyl-ethyl}-amide; and
  morpholine-4-carboxylic acid {2-(2-difluoromethoxy-phenylmethanesulfonyl)-1-[1,1-dimethyl-2-oxo-2-(5-pyridin-3-yl-[1,3,4]oxadiazol-2-yl)-ethylcarbamoyl]-ethyl}-amide.

19. A derivative selected from the group consisting of N-oxide derivatives, prodrug derivatives, protected derivatives, isomers, and mixtures of isomers, of a compound of claim 18; or a pharmaceutically acceptable salt or solvate of a compound of claim 18 or said derivative.

20. A pharmaceutical composition comprising a therapeutically effective amount of a compound of claim 1 in combination with a pharmaceutically acceptable excipient.

21. A process for preparing a compound of claim 1 by:

(A) reacting a compound of Formula (II):

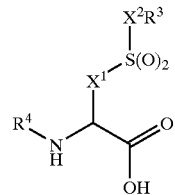
(II)

with a compound of the Formula (III):

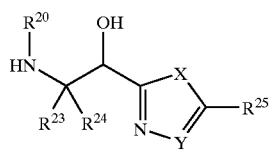
(III)

to afford a β-hydroxy amide (IV):

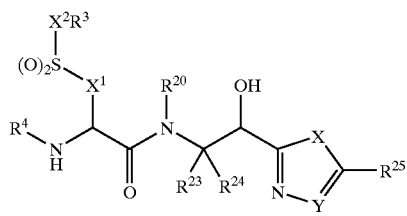
(IV)

and then oxidizing said β-hydroxy amide to afford a compound of claim 1; or (B) reacting a compound of Formula (II) with a compound of the formula (VI):

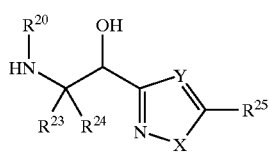
(VI)

to afford a β-hydroxy amide (VIII):

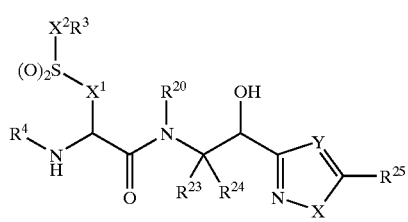
(VIII)

and then oxidizing said β-hydroxy amide to afford a compound of claim 1; or (C) reacting a compound of Formula (II) with a compound of the formula (VII):

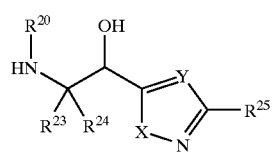
(VII)

to afford a β-hydroxy amide (IX):

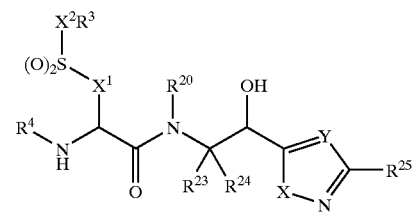
(IX)

and then oxidizing said β-hydroxy amide to afford a compound of claim 1;

wherein X, Y, $X^1$, $X^2$, $R^3$, $R^4$, $R^{20}$, $R^{23}$, $R^{24}$ and $R^{25}$ are the same as in Formula (I) defined in claim 1.

* * * * *